United States Patent
Crooke et al.

(10) Patent No.: US 9,365,848 B2
(45) Date of Patent: Jun. 14, 2016

(54) MODULATION OF APOLIPOPROTEIN C-III EXPRESSION

(71) Applicant: Ionis Pharmaceuticals, Inc., Carlsbad, CA (US)

(72) Inventors: Rosanne M. Crooke, Carlsbad, CA (US); Mark J. Graham, San Clemente, CA (US); Kristina M. Lemonidis, Oceanside, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 21 days.

(21) Appl. No.: 13/961,646

(22) Filed: Aug. 7, 2013

(65) Prior Publication Data

US 2013/0317085 A1 Nov. 28, 2013

Related U.S. Application Data

(63) Continuation of application No. 12/781,479, filed on May 17, 2010, now Pat. No. 8,530,439, which is a continuation of application No. 10/553,722, filed as application No. PCT/US2004/010946 on Apr. 15, 2004, now Pat. No. 7,750,141, which is a continuation-in-part of application No. 10/418,780, filed on Apr. 16, 2003, now Pat. No. 7,598,227.

(51) Int. Cl.
*C12N 15/113* (2010.01)
*A61K 38/00* (2006.01)

(52) U.S. Cl.
CPC ............. *C12N 15/113* (2013.01); *A61K 38/00* (2013.01); *C12N 2310/315* (2013.01); *C12N 2310/321* (2013.01); *C12N 2310/3341* (2013.01); *C12N 2310/341* (2013.01); *C12N 2310/346* (2013.01)

(58) Field of Classification Search
USPC .................... 435/6.1, 91.1, 325; 536/24.5
See application file for complete search history.

(56) References Cited

U.S. PATENT DOCUMENTS

| | | | |
|---|---|---|---|
| 5,801,154 A | 9/1998 | Baracchini et al. | |
| 5,877,009 A | 3/1999 | Zannis et al. | |
| 5,998,148 A | 12/1999 | Bennett et al. | |
| 6,010,849 A | 1/2000 | Edwards et al. | |
| 6,184,212 B1 | 2/2001 | Miraglia et al. | |
| 6,300,132 B1 | 10/2001 | Monia et al. | |
| 6,500,672 B1 | 12/2002 | Sladek et al. | |
| 6,582,908 B2 | 6/2003 | Fodor et al. | |
| 6,852,536 B2 | 2/2005 | Dobie | |
| 7,227,014 B2 * | 6/2007 | Crooke et al. | 536/24.5 |
| 7,598,227 B2 | 10/2009 | Crooke et al. | |
| 7,750,141 B2 | 7/2010 | Crooke et al. | |
| 2001/0053519 A1 | 12/2001 | Fodor et al. | |
| 2003/0228597 A1 | 12/2003 | Cowsert et al. | |
| 2004/0208856 A1 | 10/2004 | Crooke et al. | |

FOREIGN PATENT DOCUMENTS

| | | |
|---|---|---|
| WO | WO 92/10590 | 6/1992 |
| WO | WO 97/20924 | 6/1997 |
| WO | WO 03/011887 | 2/2003 |
| WO | WO 2004/093783 | 11/2004 |

OTHER PUBLICATIONS

Agrawal et al., "Antisense therapeutics: is it as simple as complementary base recognition?" Mol. Med. Today (2000) 6:72-81.
Bayarsaihan et al., Biochem J. (1996) 314:293-296.
Bennett et al., Journal of Immunology (1994) 152:3530-3540.
Braasch et al., "Novel Antisense and Peptide Nucleic Acid Strategies for Controlling Gene Expression" Biochem. (2002) 41(14):4503-4510.
Branch, "A good antisense molecule is hard to find" TIBS (1998) 23:45-50.
Chan et al., "Apolipoprotein B-100 kinetics in visceral obesity: Associations with plasma apolipoprotein C-III concentration" Metabolism Clinical and Experimental (2002) 51(8):1041-1046.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke, "Progress in Antisense Technology" Ann. Rev. Med. (2004) 55:61-95.
Crooke, "Antisense oligonucleotides as therapeutics for hyperlipidaemias" Expert Opinion on Biological Therapy (2005) 5(7):907-917.
Crooke et al., "Basic Principles of Antisense Therapeutics" Antisense Research and Application (1998) Chapter 1:1-50.
Cuchel et al., "Inhibition of Microsomal Triglyceride Transfer Protein in Familial Hypercholesterolemia" New England Journal of Medicine (2007) 356:148-156.
Dammerman et al., "An apolipoprotein CIII haplotype protective against hypertriglyceridemia is specified by promoter and 3' untranslated region polymorphisms" Proc. Natl. Acad. Sci. U. S. A., (1993) 90:4562-4566.
De Silva et al., "Overexpression of human apolipoprotein C-III in transgenic mice results in an accumulation of apolipoprotein B48 remnants that is corrected by excess apolipoprotein E" J. Biol. Chem. (1994) 269:2324-2335.
Deere et al., Antimicrobial Agents and Chemotherapy (2005) 49:249-255.
Duivenvoorden et al., "Apolipoprotein C3 Deficiency Results in Diet-Induced Obesity and Aggravated Insulin Resistance in Mice" Diabetes (2005) 54:664-671.
Final Rejection for U.S. Appl. No. 10/418,780 dated Dec. 29, 2007.
Final Rejection for U.S. Appl. No. 10/418,780 dated Mar. 19, 2008.
Final Rejection for U.S. Appl. No. 10/553,722 dated May 14, 2008.

(Continued)

*Primary Examiner* — Terra C Gibbs
(74) *Attorney, Agent, or Firm* — Grant IP, Inc.

(57) ABSTRACT

Compounds, compositions and methods are provided for modulating the expression of apolipoprotein C-III. The compositions comprise oligonucleotides, targeted to nucleic acid encoding apolipoprotein C-III. Methods of using these compounds for modulation of apolipoprotein C-III expression and for diagnosis and treatment of disease associated with expression of apolipoprotein C-III are provided.

16 Claims, No Drawings

(56) References Cited

OTHER PUBLICATIONS

Funatsu et al., "Reduction in hepatic non-esterified fatty acid concentration after long-term treatment with atorvastatin lowers hepatic triglyceride synthesis and its secretion in sucrose-fed rats" Biochimica et Biophysica Acta (2002) 1580:161-170.
GenBank Accession No. NT_035088, Aug. 2002.
Gewirtz et al., "Facilitating oligonucleotide delivery: Helping antisense deliver on its promise" PNAS USA (1996) 93:3161-3163.
Hertz et al., "Mode of action of peroxisome proliferators as hypolipidemic drugs. Suppression of apolipoprotein C-III" J. Biol. Chem. (1995) 270:13470-13475.
International Search Report and Written Opinion from PCT/US04/10946 dated Feb. 22, 2006.
Ito et al., "Hypertriglyceridemia as a result of human apo CIII gene expression in transgenic mice" Science (1990) 249:790-793.
Jen et al., "Suppression of Gene Expression by Targeted Disruption of Messenger RNA: Available Options and Current Strategies" Stem Cells (2000) 18:307-319.
Jong et al., "Role of ApoCs in Lipoprotein Metabolism—Functional Differences Between ApoC1, ApoC2, and ApoC3" Arterioscler. Thromb. Vasc. Biol. (1999) 19:472-484.
Jover et al., "Cytochrome P450 regulation by hepatocyte nuclear factor 4 in human hepatocytes: a study using adenovirus-mediated antisense targeting" Hepatology (2001) 33(3):668-675.
Karathanasis "Apolipoprotein multigene family: tandem organization of human apolipoprotein AI, CIII, and AIV genes" Proc. Natl. Acad. Sci. U. S. A. (1985) 82:6374-6378.
Kardassis et al., "Direct physical interactions between HNF-4 and Sp1 mediate synergistic transactivation of the apolipoprotein CIII promoter" Biochemistry (2002) 41:1217-1228.
Kardassis et al., "SMAD proteins transactivate the human ApoCIII promoter by interacting physically and functionally with hepatocyte nuclear factor 4" J. Biol. Chem. (2000) 275:41405-41414.
Klein et al., "P284: Apoprotein C-III (ApoCIII) Protein Concentrations and Gene Polymorphisms in Type 1 Diabetes" Aretioscler. Thromb. Vasc. Biol. (2002) 22(5):A-50.
Mayo Clinic Proceedings, Oct. 1, 1998, pp. 1-10. Hyperlipidemia and diabetes mellitus.
Levy-Wilson et al., "Isolation and DNA sequence of full-length cDNA for human preapolipoprotein CIII" DNA (1984) 3:359-364.
Li et al., "Common genetic variation in the promoter of the human apo CIII gene abolishes regulation by insulin and may contribute to hypertriglyceridemia" J. Clin. Invest. (1995) 96:2601-2605.
Maeda et al., "Molecular cloning of a human apoC-III variant: Thr 74—Ala 74 mutation prevents O-glycosylation" J. Lipid Res. (1987) 28:1405-1409.
Maeda et al., "Targeted disruption of the apolipoprotein C-III gene in mice results in hypotriglyceridemia and protection from postprandial hypertriglyceridemia" J. Biol. Chem. (1994) 269:23610-23616.
Lai et al., Yale Journal of Biology and Medicine (2001) 74:205-210.
New England Biolabs 1998/99 Catalog (cover page and pp. 121 and 284).
Nielsen, "Systemic Delivery: The Last Hurdle?" Gene Therapy (2005) 12:956-957.
Office Action for U.S. Appl. No. 10/418,780 dated Jun. 17, 2005.
Office Action for U.S. Appl. No. 10/418,780 dated Aug. 7, 2006.
Office Action for U.S. Appl. No. 10/418,780 dated Mar. 23, 2007.
Office Action for U.S. Appl. No. 10/553,722 dated Feb. 14, 2007.
Office Action for U.S. Appl. No. 10/553,722 dated Oct. 31, 2007.
Ogami et al., "Purification and characterization of a heat stable nuclear factor CIIIB1 involved in the regulation of the human ApoC-III gene" J. Biol. Chem. (1991) 266:9640-9646.
Olivieri et al., "ApoC-III gene polymorphisms and risk of coronary artery disease" J. Lipid Res. (2002) 43:1450-1457.
Olivieri et al., "Apolipoprotein C-III, n-3 Polyunsaturated Fatty Acids, and "Insulin-Resistant" T-455C APOC3 Gene Polymorphism in Heart Disease Patients: Example of Gene-Diet Interaction" Clin. Chem. (2005) 51(2):360-367.
Opalinska et al., "Nucleic-Acid Therapeutics: Basic Principles and Recent Applications" Nature Rev. Drug Discov. (2002) 1:503-514.
Protter et al., "Isolation and sequence analysis of the human apolipoprotein CIII gene and the intergenic region between the apo and apo CIII genes" DNA (1984) 3:449-456.
Raspe et al., "Identification of Rev-erbalpha as a physiological repressor of apoC-III gene transcription" J. Lipid Res. (2002) 43:2172-2179.
Restriction Requirement for U.S. Appl. No. 10/418,780 dated Feb. 10, 2005.
Restriction Requirement for U.S. Appl. No. 10/418,780 dated Nov. 30, 2007.
Reynolds et al., "Rational siRNA design for RNA interference" Nature Biotechnology (2004) 22(3):326-330.
Roglans et al., "Atorvastatin Treatment Induced Peroxisome Proliferator-Activated Receptor Alpha Expression and Decreased Plasma Nonesterified Fatty Acids and Liver Triglyceride in Fructose-Fed Rats" Journal of Pharmacology and Experimental Therapeutics (2002) 302:232-239.
Sanghvi et al., "Heterocyclic Base Modifications in Nucleic Acids and Their Applications in Antisense Oligonucleotides" Antisense Research and Applications (1993) pp. 273-288.
Schoonjans et al., "3-Hydroxy-3-methylglutaryl CoA reductase inhibitors reduce serum triglyceride levels through modulation of apolipoprotein C-III and lipoprotein lipase" FEBS Lett. (1999) 452:160-164.
Senior, "Antisense inhibitor provides new treatment approach for hypercholesterolaemia" DDT (2002) 7(16):840-841.
Shachter "Apolipoproteins C-I and C-III as important modulators of lipoprotein metabolism" Curr. Opin. Lipidol. (2001) 12:297-304.
Sharpe et al., "Human apolipoproteins AI, AII, CII and CIII. cDNA sequences and mRNA abundance" Nucleic Acids Res. (1984) 12:3917-3932.
Supplementary European Search Report for EP 04749914.0 dated Jan. 5, 2009.
Tamm et al., "Antisense therapy in oncology: new hope for an old idea?" The Lancet (2001) 358:489-497.
Ugawa et al., "YM-53601, a novel squalene synthase inhibitor, suppresses lipgenic biosynthesis and lipid secretion in rodents" British Journal of Pharmacology (2003) 139:140-146.
Vu-Dac et al., "Retinoids increase human apo C-III expression at the transcriptional level via the retinoid X receptor. Contribution to the hypertriglyceridemic action of retinoids." J. Clin. Invest. (1998) 102:625-632.
Webster's II New Riverside University Dictionary (1994) The Riverside Publishing Company, pp. 933 & 944.
Dias et al., "Antisense Oligonucleotides: Basic Concepts and Mechanisms" Molecular Cancer Therapeutics (2002) 1: 347-355.
Staels et al., "Fibrates Downregulate Apolipoprotein C-III Expression Independent of Induction of Peroxisomal Acyl Coenzyme A Oxidase" J. clin. Invest. (1995) 95: 705-712.

\* cited by examiner

MODULATION OF APOLIPOPROTEIN C-III EXPRESSION

RELATED APPLICATIONS

This application is a continuation of U.S. application Ser. No. 12/781,479, filed on May 17, 2010, now U.S. Pat. No. 8,530,439, which is a continuation of U.S. application Ser. No. 10/553,722, filed on Jul. 10, 2006, now U.S. Pat. No. 7,750,141, which is a continuation of International PCT Patent Application No. PCT/US2004/010946, filed on Apr. 15, 2004, which is a continuation-in-part of U.S. application Ser. No. 10/418,780, filed on Apr. 16, 2003, now U.S. Pat. No. 7,598,227, each of which is herein incorporated by reference in its entirety.

SEQUENCE LISTING

The present application is being filed along with a Sequence Listing in electronic format. The Sequence Listing is provided as a file entitled BIOL0004USC2SEQ.txt, created on Aug. 2, 2013 which is 92 Kb in size. The information in the electronic format of the sequence listing is incorporated herein by reference in its entirety.

FIELD OF THE INVENTION

The present invention provides compositions and methods for modulating the expression of apolipoprotein C-III. In particular, this invention relates to compounds, particularly oligonucleotide compounds, which, in preferred embodiments, hybridize with nucleic acid molecules encoding apolipoprotein C-III. Such compounds are shown herein to modulate the expression of apolipoprotein C-III.

BACKGROUND OF THE INVENTION

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, which transport dietary lipids from intestine to tissues; very low density lipoproteins (VLDL); intermediate density lipoproteins (IDL); low density lipoproteins (LDL); all of which transport triacylglycerols and cholesterol from the liver to tissues; and high density lipoproteins (HDL), which transport endogenous cholesterol from tissues to the liver.

Lipoprotein particles undergo continuous metabolic processing and have variable properties and compositions. Lipoprotein densities increase without decreasing particle diameter because the density of their outer coatings is less than that of the inner core. The protein components of lipoproteins are known as apolipoproteins. At least nine apolipoproteins are distributed in significant amounts among the various human lipoproteins.

Apolipoprotein C-III is a constituent of HDL and of triglyceride-rich lipoproteins and has a role in hypertriglyceridemia, a risk factor for coronary artery disease. Apolipoprotein C-III slows this clearance of triglyceride-rich lipoproteins by inhibiting lipolysis, both through inhibition of lipoprotein lipase and by interfering with lipoprotein binding to the cell-surface glycosaminoglycan matrix (Shachter, *Curr. Opin. Lipidol.*, 2001, 12, 297-304).

The gene encoding human apolipoprotein C-III (also called APOC3, APOC-III, APO CIII, and APO C-III) was cloned in 1984 by three research groups (Levy-Wilson et al., *DNA*, 1984, 3, 359-364; Protter et al., *DNA*, 1984, 3, 449-456; Sharpe et al., *Nucleic Acids Res.*, 1984, 12, 3917-3932). The coding sequence is interrupted by three introns (Protter et al., *DNA*, 1984, 3, 449-456). The human apolipoprotein C-III gene is located approximately 2.6 kB to the 3' direction of the apolipoprotein A-1 gene and these two genes are convergently transcribed (Karathanasis, *Proc. Natl. Acad. Sci. U.S.A.*, 1985, 82, 6374-6378). Also cloned was a variant of human apolipoprotein C-III with a Thr74 to Ala74 mutation from a patient with unusually high level of serum apolipoprotein C-III. As the Thr74 is O-glycosylated, the Ala74 mutant therefore resulted in increased levels of serum apolipoprotein C-III lacking the carbohydrate moiety (Maeda et al., *J. Lipid Res.*, 1987, 28, 1405-1409).

Five polymorphisms have been identified in the promoter region of the gene: C(−641) to A, G(−630) to A, T(−625) to deletion, C(−482) to T and T(−455) to C. All of these polymorphisms are in linkage disequilibrium with the SstI polymorphism in the 3' untranslated region. The SstI site distinguishes the S1 and S2 alleles and the S2 allele has been associated with elevated plasma triglyceride levels (Dammerman et al., *Proc. Natl. Acad. Sci. U.S.A.*, 1993, 90, 4562-4566). The apolipoprotein C-III promoter is downregulated by insulin and this polymorphic site abolishes the insulin regulation. Thus the potential overexpression of apolipoprotein C-III resulting from the loss of insulin regulation may be a contributing factor to the development of hypertriglyceridemia associated with the S2 allele (Li et al., *J. Clin. Invest.*, 1995, 96, 2601-2605). The T(−455) to C polymorphism has been associated with an increased risk of coronary artery disease (Olivieri et al., *J. Lipid Res.*, 2002, 43, 1450-1457).

In addition to insulin, other regulators of apolipoprotein C-III gene expression have been identified. A response element for the nuclear orphan receptor rev-erb alpha has been located at positions −23/−18 in the apolipoprotein C-III promoter region and rev-erb alpha decreases apolipoprotein C-III promoter activity (Raspe et al., *J. Lipid Res.*, 2002, 43, 2172-2179). The apolipoprotein C-III promoter region −86 to −74 is recognized by two nuclear factors CIIIb and CIIIB2 (Ogami et al., *J. Biol. Chem.*, 1991, 266, 9640-9646). Apolipoprotein C-III expression is also upregulated by retinoids acting via the retinoid X receptor, and alterations in retinoid X receptor abundance affects apolipoprotein C-III transcription (Vu-Dac et al., *J. Clin. Invest.*, 1998, 102, 625-632). Specificity protein 1 (Spl) and hepatocyte nuclear factor-4 (HNF-4) have been shown to work synergistically to transactivate the apolipoprotein C-III promoter via the HNF-4 binding site (Kardassis et al., *Biochemistry*, 2002, 41, 1217-1228). HNF-4 also works in conjunction with SMAD3-SMAD4 to transactivate the apolipoprotein C-III promoter (Kardassis et al., *J. Biol. Chem.*, 2000, 275, 41405-41414).

Transgenic and knockout mice have further defined the role of apolipoprotein C-III in lipolysis. Overexpression of apolipoprotein C-III in transgenic mice leads to hypertriglyceridemia and impaired clearance of VLDL-triglycerides (de Silva et al., *J. Biol. Chem.*, 1994, 269, 2324-2335; Ito et al., *Science*, 1990, 249, 790-793). Knockout mice with a total absence of the apolipoprotein C-III protein exhibited significantly reduced plasma cholesterol and triglyceride levels compared with wild-type mice and were protected from postprandial hypertriglyceridemia (Maeda et al., *J. Biol. Chem.*, 1994, 269, 23610-23616).

Currently, there are no known therapeutic agents that affect the function of apolipoprotein C-III. The hypolipidemic effect of the fibrate class of drugs has been postulated to occur via a mechanism where peroxisome proliferator activated receptor (PPAR) mediates the displacement of HNF-4 from the apolipoprotein C-III promoter, resulting in transcriptional suppression of apolipoprotein C-111 (Hertz et al., *J. Biol. Chem.,* 1995, 270, 13470-13475). The statin class of hypolipidemic drugs also lower triglyceride levels via an unknown mechanism, which results in increases in lipoprotein lipase mRNA and a decrease in plasma levels of apolipoprotein C-III (Schoonjans et al., *FEBS Lett.,* 1999, 452, 160-164). Consequently, there remains a long felt need for additional agents capable of effectively inhibiting apolipoprotein C-III function.

SUMMARY OF THE INVENTION

The present invention provides compositions and methods for modulating apolipoprotein C-III expression. Antisense technology is emerging as an effective means for reducing the expression of specific gene products and is uniquely useful in a number of therapeutic, diagnostic, and research applications for the modulation of apolipoprotein C-III expression.

The present invention is directed to compounds, especially nucleic acid and nucleic acid-like oligomers, which are targeted to a nucleic acid encoding apolipoprotein C-III, and which modulate the expression of apolipoprotein C-III. Pharmaceutical and other compositions comprising the compounds of the invention are also provided.

Further provided are methods of screening for modulators of apolipoprotein C-III and methods of modulating the expression of apolipoprotein C-III in cells, tissues or animals comprising contacting said cells, tissues or animals with one or more of the compounds or compositions of the invention. In these methods, the cells or tissues are contacted in vivo. Alternatively, the cells or tissues are contacted ex vivo.

Methods of treating an animal, particularly a human, suspected of having or being prone to a disease or condition associated with expression of apolipoprotein C-III are also set forth herein. Such methods comprise administering a therapeutically or prophylactically effective amount of one or more of the compounds or compositions of the invention to the person in need of treatment.

Also provided is a method of making a compound of the invention comprising specifically hybridizing in vitro a first nucleobase strand comprising a sequence of at least 8 contiguous nucleobases of the sequence set forth in SEQ ID NO: 4 and/or SEQ ID NO: 18 to a second nucleobase strand comprising a sequence sufficiently complementary to said first strand so as to permit stable hybridization.

The invention further provides a compound of the invention for use in therapy.

The invention further provides use of a compound or composition of the invention in the manufacture of a medicament for the treatment of any and all conditions disclosed herein.

DETAILED DESCRIPTION OF THE INVENTION

A. Overview of the Invention

The present invention employs compounds, preferably oligonucleotides and similar species for use in modulating the function or effect of nucleic acid molecules encoding apolipoprotein C-III. This is accomplished by providing oligonucleotides that specifically hybridize with one or more nucleic acid molecules encoding apolipoprotein C-III.

As used herein, the terms "target nucleic acid" and "nucleic acid molecule encoding apolipoprotein C-III" have been used for convenience to include DNA encoding apolipoprotein C-III, RNA (including pre-mRNA and mRNA or portions thereof) transcribed from such DNA, and also cDNA derived from such RNA.

The hybridization of a compound of this invention with its target nucleic acid is generally referred to as "antisense". Consequently, the mechanism included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of apolipoprotein C-III. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases, which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and are different in different circumstances. In the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases that can hydrogen bond with each other. Thus, "specifically hybridizable" and "complementary" are terms that are used to indicate a sufficient degree of precise pairing or complementarity over a sufficient number of nucleobases such that stable and specific binding occurs between the oligonucleotide and a target nucleic acid.

It is understood in the art that the sequence of the antisense compound of this invention can be, but need not be, 100% complementary to that of the target nucleic acid to be specifically hybridizable. Moreover, an oligonucleotide may hybridize over one or more segments such that intervening or adjacent segments are not involved in the hybridization event (e.g., a loop structure or hairpin structure). In one embodiment, the antisense compounds of the present invention comprise at least 70%, or at least 75%, or at least 80%, or at least 85% sequence complementarity to a target region within the target nucleic acid. In another embodiment, the antisense compounds of this invention comprise 90% sequence complementarity and even more preferably comprise 95% or at least 99% sequence complementarity to the target region within the target nucleic acid sequence to which they are targeted. Preferably, the antisense compounds comprise at least 8 contiguous nucleobases of an antisense compound disclosed herein. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, 1981, 2, 482-489). In some preferred embodiments, homology, sequence identity or complementarity, between the oligomeric and target is between about 50% to about 60%. In some embodiments, homology, sequence identity or complementarity, is between about 60% and about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, or about 99%.

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNAse H, therefore, results in cleavage of the RNA target, thereby greatly enhancing the efficiency of oligonucleotide-mediated inhibition of gene expression. Similar roles have been postulated for other ribonucleases such as those in the RNAse III and ribonuclease L family of enzymes.

While the preferred form of antisense compound is a single-stranded antisense oligonucleotide, in many species the introduction of double-stranded structures, such as double-stranded RNA (dsRNA) molecules, induces potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620).

The primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, the single-stranded RNA oligomers of antisense polarity of the dsRNAs have been reported to be potent inducers of RNAi (Tijsterman et al., *Science*, 2002, 295, 694-697).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

The oligonucleotides of the present invention also include modified oligonucleotides in which a different nucleobase is present at one or more of the nucleotide positions in the oligonucleotide. For example, if the first nucleotide is adenosine, modified oligonucleotides may be produced that contain thymidine, quanosine or cytidine at this position. This may be done at any of the positions of the oligonucleotide. These oligonucleotides are then tested using the methods described herein to determine their ability to inhibit expression of apolipoprotein C-III.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). Exemplary compounds of this invention from a variety of mammalian sources, including human, may be found identified in the Examples and listed in Tables 1 through 21. One having skill in the art armed with the preferred antisense compounds illustrated herein will be able, without undue experimentation, to identify further preferred antisense compounds.

C. Targets of the Invention

"Targeting" an antisense compound to a target nucleic acid molecule encoding apolipoprotein C-III, in the context of this invention, can be a multi-step process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes apolipoprotein C-III.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes, having translation initiation codons with the RNA sequence 5'-GUG, 5'-UUG or 5'-CUG, and 5'-AUA, 5'-ACG and 5'-CUG, have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding apolipoprotein C-III, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Accordingly, the present invention provides antisense compounds that target a portion of nucleobases 1-533 as set forth in SEQ ID NO: 18. In one embodiment, the antisense compounds target at least an 8 nucleobase portion of nucleobases 1-533 as set forth in SEQ ID NO: 18 and Tables 1 and 4. In another embodiment, the antisense compounds target at least an 8 nucleobase portion of nucleobases comprising the 5' UTR as set forth in SEQ ID NO: 18 and Tables 1 and 4. In another embodiment, the antisense compounds target at least an 8 nucleobase portion of nucleobases comprising the 3' UTR as set forth in SEQ ID NO: 18 and Tables 1 and 4. In another embodiment, the antisense compounds target at least an 8 nucleobase portion of nucleobases comprising the coding region as set forth in SEQ ID NO: 18 and Tables 1 and 4. In still other embodiments, the antisense compounds target at least an 8 nucleobase portion of a "preferred target segment" (as defined herein) as set forth in Table 3.

Further, the present invention provides antisense compounds that target a portion of nucleobases 1-3958 as set forth in SEQ ID NO: 4. In one embodiment, the antisense compounds target at least an 8 nucleobase portion of nucleobases 1-3958 as set forth in SEQ ID NO: 4 and Tables 1 and 4. In another embodiment, the antisense compounds target at least an 8 nucleobase portion of nucleobases comprising the 5' UTR as set forth in SEQ ID NO: 4 and Tables 1 and 4. In another embodiment, the antisense compounds target at least an 8 nucleobase portion of nucleobases comprising the 3' UTR as set forth in SEQ ID NO: 4 and Tables 1 and 4. In another embodiment, the antisense compounds target at least an 8 nucleobase portion of nucleobases comprising the coding region as set forth in SEQ ID NO: 4 and Tables 1 and 4. In still other embodiments, the antisense compounds target at least an 8 nucleobase portion of a "preferred target segment" (as defined herein) as set forth in Table 3.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid that are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric compounds are targeted to or not targeted to regions of the target apolipoprotein C-III nucleobase sequence (e.g., such as those disclosed in Examples 15 and 17) comprising nucleobases 1-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, 2001-2050, 2051-2100, 2101-2150, 2151-2200, 2201-2250, 2251-2300, 2301-2350, 2351-2400, 2401-2450, 2451-2500, 2501-2550, 2551-2600, 2601-2650, 2651-2700, 2701-2750, 2751-2800, 2801-2850, 2851-2900, 2901-2950, 2591-3000, 3001-3050, 3051-3100, 3101-3150, 3151-3200, 3201-3250, 3251-3300, 3301-3350, 3351-3400, 3401-3450, 3451-3500, 3501-3550, 3551-3600, 3601-3650, 3651-3700, 3701-3750, 3751-3800, 3801-3850, 3851-3900, 3901-3950, 3951-3958 of SEQ ID NO: 4, or any combination thereof.

Further, the oligomeric compounds are targeted to or not targeted to regions of the target apolipoprotein C-III nucleobase sequence (e.g., such as those disclosed in Examples 15 and 17) comprising nucleobases 1-50, 51-100, 101-150, 151-200, 201-250, 251-300, 301-350, 351-400, 401-450, 451-500, 501-533 of SEQ ID NO: 18, or any combination thereof.

In one embodiment, the oligonucleotide compounds of this invention are 100% complementary to these sequences or to small sequences found within each of the above-listed sequences. Preferably, the antisense compounds comprise at least 8 contiguous nucleobases of an antisense compound disclosed herein. In another embodiment, the oligonucleotide compounds have from at least 3 or 5 mismatches per 20 consecutive nucleobases in individual nucleobase positions to these target regions. Still other compounds of the invention are targeted to overlapping regions of the above-identified portions of the apolipoprotein C-III sequence.

D. Screening and Target Validation

In a further embodiment, the "preferred target segments" identified herein may be employed in a screen for additional compounds that modulate the expression of apolipoprotein C-III. "Modulators" are those compounds that decrease or increase the expression of a nucleic acid molecule encoding apolipoprotein C-III and which comprise at least an 8-nucleobase portion that is complementary to a preferred target segment. The screening method comprises the steps of contacting a preferred target segment of a nucleic acid molecule encoding apolipoprotein C-III with one or more candidate modulators, and selecting for one or more candidate modulators which decrease or increase the expression of a nucleic acid molecule encoding apolipoprotein C-III. Once it is shown that the candidate modulator or modulators are capable of modulating (e.g. either decreasing or increasing) the expression of a nucleic acid molecule encoding apolipoprotein C-III, the modulator may then be employed in further investigative studies of the function of apolipoprotein C-III, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between apolipoprotein C-III and a disease state, phenotype, or condition. These methods include detecting or modulating apolipoprotein C-III comprising contacting a sample, tissue, cell, or organism with the compounds of the present invention, measuring the nucleic acid or protein level of apolipoprotein C-III and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention are utilized for diagnostics, therapeutics, prophylaxis, and as research reagents and kits. In one embodiment, such compounds of the invention are useful in areas of obesity and metabolic-related disorders such as hyperlipidemia. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, are used as tools in differential and/or combinatorial analyses to elucidate expression patterns of a portion or the entire complement of genes expressed within cells and tissues.

As used herein, the term "system" is defined as any organism, cell, cell culture or tissue that expresses, or is made competent to express products of the gene encoding apolipoprotein C-III. These include, but are not limited to, humans, transgenic animals, cells, cell cultures, tissues, xenografts, transplants and combinations thereof.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The compounds of the invention are useful for research and diagnostics, because these compounds hybridize to nucleic acids encoding apolipoprotein C-III. For example, oligonucleotides that are shown to hybridize with such efficiency and under such conditions as disclosed herein as to be effective apolipoprotein C-III inhibitors will also be effective primers or probes under conditions favoring gene amplification or detection, respectively. These primers and probes are useful in methods requiring the specific detection of nucleic acid molecules encoding apolipoprotein C-III and in the amplification of said nucleic acid molecules for detection or for use in further studies of apolipoprotein C-III. Hybridization of the antisense oligonucleotides, particularly the primers and probes, of the invention with a nucleic acid encoding apolipoprotein C-III can be detected by means known in the art. Such means may include conjugation of an enzyme to the oligonucleotide, radiolabelling of the oligonucleotide or any other suitable detection means. Kits using such detection means for detecting the level of apolipoprotein C-III in a sample may also be prepared.

Also provided is a method of making a compound of the invention comprising specifically hybridizing in vitro a first nucleobase strand comprising a sequence of at least 8 contiguous nucleobases of the sequence set forth in SEQ ID NO: 4 and/or SEQ ID NO: 18 to a second nucleobase strand comprising a sequence sufficiently complementary to said first strand so as to permit stable hybridization.

The invention further provides a compound of the invention for use in therapy.

The invention further provides use of a compound or composition of the invention in the manufacture of a medicament for the treatment of any and all conditions disclosed herein.

Among diagnostic uses is the measurement of apolipoprotein C-III in patients to identify those who may benefit from a treatment strategy aimed at reducing levels of apolipoprotein C-III. Such patients suitable for diagnosis include patients with hypertriglyceridemia (e.g., to diagnose tendencies for coronary artery disease), abnormal lipid metabolism, obesity, hyperlipidemia, among other disorders.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of apolipoprotein C-III is treated by administering antisense compounds in accordance with this invention. For example, in one non-limiting embodiment, the methods comprise the step of administering to the animal in need of treatment, a therapeutically effective amount of an apolipoprotein C-III inhibitor. The apolipoprotein C-III inhibitors of the present invention effectively inhibit the activity of the apolipoprotein C-III protein or inhibit the expression of the apolipoprotein C-III protein. For example, such a compound that reduces levels of apolipoprotein C-III is useful to prevent morbidity and mortality for subjects with cardiac-related disorders. For example, as demonstrated in the examples, reduction in apolipoprotein C-III can result in a reduction in the serum levels of cholesterol, triglycerides, and glucose. Thus, apolipoprotein C-III inhibitors are useful in the treatment of hypertriglyceridemia, abnormal lipid metabolism, abnormal cholesterol metabolism, atherosclerosis, hyperlipidemia, diabetes, including Type 2 diabetes, obesity, cardiovascular disease, coronary artery disease, among other disorders relating to abnormal metabolism or otherwise.

In one embodiment, the activity or expression of apolipoprotein C-III in an animal is inhibited by about 10%. Preferably, the activity or expression of apolipoprotein C-III in an animal is inhibited by about 30%. More preferably, the activity or expression of apolipoprotein C-III in an animal is inhibited by 50% or more. Thus, the oligomeric compounds modulate expression of apolipoprotein C-III mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of apolipoprotein C-III may be measured in serum, adipose tissue, liver or any other body fluid, tissue or organ of the animal. Preferably, the cells contained within said fluids, tissues or organs being analyzed contain a nucleic acid molecule encoding apolipoprotein C-III and/or apolipoprotein C-III.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue, which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)— $CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O—, S—, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_m$ $CH_3$, $O(CH_2)_nOCH_3$, $O(CH_2)_nNH_2$, $O(CH_2)_nCH_3$, $O(CH_2)_n$ $ONH_2$, and $O(CH_2)_nON[(CH_2)CH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy(2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification includes 2'-dimethylaminooxyethoxy, i.e., a $O(CH_2)_2ON$ $(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples hereinbelow.

Other preferred modifications include 2'-methoxy(2'-O—CH$_3$), 2'-aminopropoxy(2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—CH$_2$—)$_n$ group bridging the 2' oxygen atom and the 4' carbon atom wherein n is 1 or 2. LNAs and preparation thereof are described in International Patent Publication Nos. WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2': 4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The *Concise Encyclopedia Of Polymer Science And Engineering, pages* 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications, pages* 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenan-thridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999), which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds that are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNAse H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

In one embodiment, desirable chimeric oligonucleotides are 20 nucleotides in length, composed of a central region consisting of ten 2'-deoxynucleotides, flanked on both sides (5' and 3' directions) by five 2'-methoxyethyl (2'-MOE) nucleotides. The internucleoside linkages are phosphorothioate throughout the oligonucleotide and all cytidine residues are 5-methylcytidines.

In another embodiment, certain preferred chimeric oligonucleotides are those disclosed in the Examples herein. Particularly preferred chimeric oligonucleotides are those referred to as ISIS 304757, ISIS 304758, ISIS 304755, ISIS304800, and ISIS 304756.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly
owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in International Patent Application Publication No. WO 93/24510 to Gosselin et al., published Dec. 9, 1993, or in International Patent Publication No. WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes, which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term that, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to affect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315, 298, filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287, 860, which is incorporated herein in its entirety. Also preferred are combinations of penetration enhancers, for example, fatty acids/salts in combination with bile acids/ salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. Published Patent Application No. 2003/0040497 (Feb. 27, 2003) and its parent applications; U.S. Published Patent Application No. 2003/0027780 (Feb. 6, 2003) and its parent applications; and U.S. patent application Ser. No. 10/071,822, filed Feb. 8, 2002, each of which is incorporated herein by reference in their entirety.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents, which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemo-therapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Synthesis of Nucleoside Phosphoramidites

The following compounds, including amidites and their intermediates were prepared as described in U.S. Pat. No. 6,426,220 and International Patent Publication No. WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N-4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amidite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-

(Dimethylaminooxyethoxy) nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy(2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or 5,366,878, herein incorporated by reference.

Alkylphosphonothioate oligonucleotides are prepared as described in International Patent Application Nos. PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group, which has the following important properties. It is stable to the conditions of nucleoside phosphoramidite synthesis and oligonucleotide synthesis. However, after oligonucleotide synthesis the oligonucleotide is treated with methylamine, which not only cleaves the oligonucleotide from the solid support but also removes the acetyl groups from the orthoesters. The resulting 2-ethyl-hydroxyl substituents on the orthoester are less-electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand.,* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting Apolipoprotein C-III In accordance with the present invention, a series of nucleic acid duplexes comprising the antisense compounds of the present invention and their complements are designed to target apolipoprotein C-III. The nucleobase sequence of the antisense strand of the duplex comprises at least a portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 465) and having a two-nucleobase overhang of deoxythymidine (dT) would have the following structure (Antisense SEQ ID NO: 466, Complement SEQ ID NO: 467):

In another embodiment, a duplex comprising an antisense strand having the same sequence CGAGAGGCGGACGG-GACCG (SEQ ID NO: 465) may be prepared with blunt ends (no single stranded overhang) as shown (Antisense SEQ ID NO: 465, Complement SEQ ID NO: 468):

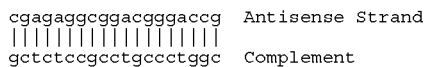

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 µM. Once diluted, 30 µL of each strand is combined with 15 µL of a 5× solution of annealing buffer. The final concentration of said buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM. This solution can be stored frozen (−20° C.) and freeze-thawed up to 5 times.

Once prepared, the duplexed antisense compounds are evaluated for their ability to modulate apolipoprotein C-III expression.

When cells reached 80% confluency, they are treated with duplexed antisense compounds of the invention. For cells grown in 96-well plates, wells are washed once with 200 µL OPTI-MEM-1™ reduced-serum medium (Gibco BRL) and then treated with 130 µL of OPTI-MEM-1™ medium containing 12 µg/mL LIPOFECTIN™ reagent (Gibco BRL) and the desired duplex antisense compound at a final concentration of 200 nM. After 5 hours of treatment, the medium is replaced with fesh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full-length material. The relative amounts of phosphorothioate and phosphodiester linkages obtained in the synthesis were determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ apparatus) or, for individually prepared samples, on a commercial CE apparatus (e.g., Beckman P/ACE™ 5000, ABI 270 apparatus). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

HepG2 Cells:

The human hepatoblastoma cell line HepG2 was obtained from the American Type Culture Collection (Manassas, Va.). HepG2 cells were routinely cultured in Eagle's MEM supplemented with 10% fetal calf serum, non-essential amino acids, and 1 mM sodium pyruvate (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

Hep3B Cells:

The human hepatocellular carcinoma cell line Hep3B was obtained from the American Type Culture Collection (Manassas, Va.). Hep3B cells were routinely cultured in Dulbeccos's MEM high glucose supplemented with 10% fetal calf serum, L-glutamine and pyridoxine hydrochloride (Gibco/Life Technologies, Gaithersburg, Md.). Cells were routinely passaged by trypsinization and dilution when they reached 90% confluence. Cells were seeded into 24-well plates (Falcon-Primaria #3846) at a density of 50,000 cells/well for use in RT-PCR analysis.

For Northern blotting or other analyses, cells may be seeded onto 100 mm or other standard tissue culture plates and treated similarly, using appropriate volumes of medium and oligonucleotide.

Primary Mouse Hepatocytes:

Primary mouse hepatocytes were prepared from CD-1 mice purchased from Charles River Labs (Wilmington, Mass.) and were routinely cultured in DMEM, high glucose (Invitrogen Life Technologies, Carlsbad, Calif.) supplemented with 10% fetal bovine serum (Invitrogen Life Technologies, Carlsbad, Calif.), 100 units per ml penicillin, and 100 micrograms per ml streptomycin (Invitrogen Life Technologies, Carlsbad, Calif.). Cells were cultured to 80% confluence for use in antisense oligonucleotide transfection experiments.

For Northern blotting or other analyses, cells may be seeded onto 100 mm or other standard tissue culture plates and treated similarly, using appropriate volumes of medium and oligonucleotide.

Primary Rat Hepatocytes:

Primary rat hepatocytes were prepared from Sprague-Dawley rats purchased from Charles River Labs (Wilmington, Mass.) and were routinely cultured in DMEM, high glucose (Invitrogen Life Technologies, Carlsbad, Calif.) supplemented with 10% fetal bovine serum (Invitrogen Life Technologies, Carlsbad, Calif.), 100 units per ml penicillin, and 100 micrograms per ml streptomycin (Invitrogen Life Technologies, Carlsbad, Calif.). Cells were cultured to 80% confluence for use in antisense oligonucleotide transfection experiments.

Treatment with Antisense Compounds:

When cells reached 65-75% confluency, they were treated with oligonucleotide. For cells grown in 96-well plates, wells were washed once with 100 μL OPTI-MEM™-1 reduced-serum medium (Invitrogen Life Technologies, Carlsbad, Calif.) and then treated with 130 μL of OPTI-MEM™-1 medium containing 3.75 g/mL LIPOFECTIN™ reagent (Invitrogen Life Technologies, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Apolipoprotein C-III Expression

Antisense modulation of apolipoprotein C-III expression can be assayed in a variety of ways known in the art. For example, apolipoprotein C-III mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of apolipoprotein C-III can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to apolipoprotein C-III can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and In Vivo Studies for the Use of Apolipoprotein C-III Inhibitors Phenotypic Assays Once apolipoprotein C-III inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of apolipoprotein C-III in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with apolipoprotein C-III inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status, which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the apolipoprotein C-III inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study. To account for the psychological effects of receiving treatments, volunteers are randomly given placebo or apolipoprotein C-III inhibitor. Furthermore, to prevent the doctors from being biased in treatments, they are not informed as to whether the medication they are administering is a apolipoprotein C-III inhibitor or a placebo. Using this randomization approach, each volunteer has the same chance of being given either the new treatment or the placebo.

Volunteers receive either the apolipoprotein C-III inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding apolipoprotein C-III or the levels of apolipoprotein C-III protein in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and apolipoprotein C-III inhibitor treatment. In general, the volunteers treated with placebo have little or no response to treatment, whereas the volunteers treated with the apolipoprotein C-III inhibitor show positive trends in their disease state or condition index at the conclusion of the study.

Example 12

RNA Isolation

Poly(A)+ mRNA isolation

Poly(A)+ mRNA was isolated according to Miura et al., (Clin. Chem., 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIA-VAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIA-VAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN® Bio-Robot™9604 apparatus (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Apolipoprotein C-III mRNA Levels

Quantitation of apolipoprotein C-III mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5×PCR buffer minus $MgCl_2$, 6.6 mM $MgCl_2$, 375 M each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ reagent (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ reagent are taught in Jones, L. J., et al., (*Analytical Biochemistry*, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 reader (PE Applied Biosystems) with excitation at 485 nm and emission at 530 nm.

Probes and primers to human apolipoprotein C-III were designed to hybridize to a human apolipoprotein C-III sequence, using published sequence information (nucleotides 6238608 to 6242565 of the sequence with GenBank accession number NT_035088.1, incorporated herein as SEQ ID NO: 4). For human apolipoprotein C-III the PCR primers were:
forward primer: TCAGCTTCATGCAGGGTTACAT (SEQ ID NO: 5)
reverse primer: ACGCTGCTCAGTGCATCCT (SEQ ID NO: 6) and the PCR probe was: FAM-AAGCACGCCAC-CAAGACCGCC-TAMRA
(SEQ ID NO: 7) where FAM is the fluorescent dye and TAMRA is the quencher dye. For human GAPDH the PCR primers were:
forward primer: GAAGGTGAAGGTCGGAGTC(SEQ ID NO: 8)
reverse primer: GAAGATGGTGATGGGATTTC GGGTCTCGCTCCTGGAAGAT (SEQ ID NO: 9) and the PCR probe was: 5' JOE-CAAGCTTCCCGTTCTCAGCC-TAMRA 3' (SEQ ID NO: 10) where JOE is the fluorescent reporter dye and TAMRA is the quencher dye.

Probes and primers to mouse apolipoprotein C-III were designed to hybridize to a mouse apolipoprotein C-III sequence, using published sequence information (GenBank accession number L04150.1, incorporated herein as SEQ ID NO: 11). For mouse apolipoprotein C-III the PCR primers were:
forward primer: TGCAGGGCTACATGGAACAA (SEQ ID NO: 12)
reverse primer: CGGACTCCTGCACGCTACTT (SEQ ID NO: 13) and the PCR probe was: FAM-CTCCAAGACG-GTCCAGGATGCGC-TAMRA
(SEQ ID NO: 14) where FAM is the fluorescent reporter dye and TAMRA is the quencher dye. For mouse GAPDH the PCR primers were:
forward primer: GGCAAATTCAACGGCACAGT (SEQ ID NO: 15)
reverse primer: GGGTCTCGCTCCTGGAAGAT (SEQ ID NO: 16) and the PCR probe was: 5' JOE-AAGGCCGAGAATGGGAAGCT-TGTCATC-TAMRA 3' (SEQ ID NO: 17) where JOE is the fluorescent reporter dye and TAMRA is the quencher dye.

Example 14

Northern Blot Analysis of Apolipoprotein C-III mRNA Levels

Eighteen hours after antisense treatment, cell monolayers were washed twice with cold PBS and lysed in 1 mL RNA-ZOL™ reagent (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human apolipoprotein C-III, a human apolipoprotein C-III specific probe was prepared by PCR using the forward primer TCAGCTTCATGCAGGGTTACAT (SEQ ID NO: 5) and the reverse primer ACGCTGCTCAGTG-CATCCT (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse apolipoprotein C-III, a mouse apolipoprotein C-III specific probe was prepared by PCR using the forward primer TGCAGGGCTACATGGAACAA (SEQ ID NO: 12) and the reverse primer CGGACTCCTGCACGC-TACTT (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ apparatus and IMAGEQUANT™ Software V3.3 (Molecular Dynamics, Sunnyvale, Calif.). Data was normalized to GAPDH levels in untreated controls.

Example 15

Antisense Inhibition of Human Apolipoprotein C-III Expression by Chimeric Phosphorothioate Oligonucleotides Having 2'-MOE Wings and a Deoxy Gap In accordance with the present invention, a series of antisense compounds was designed to target different regions of the human apolipoprotein C-III RNA, using published sequences (nucleotides 6238608 to 6242565 of GenBank accession number NT_035088.1, representing a genomic sequence, incorporated herein as SEQ ID NO: 4, and GenBank accession number NM_000040.1, incorporated herein as SEQ ID NO: 18). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-(2-methoxyethyl) nucleotides, also known as (2'-MOE)nucleotides. The internucleoside (backbone) linkages are phosphorothioate (P=S) throughout the oligonucleotide. All cytidine residues are 5-methylcytidines. The compounds were analyzed for their effect on human apolipoprotein C-III mRNA levels by quantitative real-time PCR as described in other examples herein. Data are averages from three experiments in which HepG2 cells were treated with the antisense oligonucleotides of the present invention. The positive control for each datapoint is identified in the table by sequence ID number. If present, "N.D." indicates "no data".

TABLE 1

Inhibition of human apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 167824 | 5'UTR | 4 | 414 | ctggagcagctgcctctagg | 79 | 19 | 1 |
| 167835 | Coding | 4 | 1292 | ccctgcatgaagctgagaag | 60 | 20 | 1 |
| 167837 | Coding | 18 | 141 | gtgcttcatgtaaccctgca | 88 | 21 | 1 |
| 167846 | Coding | 4 | 1369 | tggcctgctgggccacctgg | 66 | 22 | 1 |
| 167848 | Coding | 4 | 3278 | tgctccagtagtcttcagg | 81 | 23 | 1 |
| 167851 | Coding | 4 | 3326 | tgacctcagggtccaaatcc | 41 | 24 | 1 |
| 304739 | 5'UTR | 4 | 401 | ctctagggatgaactgagca | 62 | 25 | 1 |
| 304740 | 5'UTR | 4 | 408 | cagctgcctctagggatgaa | 44 | 26 | 1 |
| 304741 | 5'UTR | 18 | 17 | ttcctggagcagctgcctct | 57 | 27 | 1 |
| 304742 | 5'UTR | 18 | 24 | acctctgttcctggagcagc | 78 | 28 | 1 |
| 304743 | Start Codon | 18 | 29 | atggcacctctgttcctgga | 78 | 29 | 1 |
| 304744 | Start Codon | 4 | 1065 | gggctgcatggcacctctgt | 73 | 30 | 1 |
| 304745 | Coding | 4 | 1086 | ggcaacaacaaggagtaccc | 90 | 31 | 1 |
| 304746 | Coding | 4 | 1090 | ggagggcaacaacaaggagt | 80 | 32 | 1 |
| 304747 | Coding | 18 | 87 | agctcgggcagaggccagga | 49 | 33 | 1 |
| 304748 | Coding | 18 | 92 | tctgaagctcgggcagaggc | 72 | 34 | 1 |
| 304749 | Coding | 18 | 97 | cggcctctgaagctcgggca | 11 | 35 | 1 |
| 304750 | Coding | 4 | 1267 | catcctcggcctctgaagct | 49 | 36 | 1 |
| 304751 | Coding | 4 | 1273 | gggaggcatcctcggcctct | 65 | 37 | 1 |
| 304752 | Coding | 4 | 1278 | gagaagggaggcatcctcgg | 82 | 38 | 1 |
| 304753 | Coding | 4 | 1281 | gctgagaagggaggcatcct | 75 | 39 | 1 |
| 304754 | Coding | 4 | 1289 | tgcatgaagctgagaaggga | 74 | 40 | 1 |
| 304755 | Coding | 18 | 143 | gcgtgcttcatgtaaccctg | 95 | 41 | 1 |
| 304756 | Coding | 4 | 1313 | ttggtggcgtgcttcatgta | 92 | 42 | 1 |
| 304757 | Coding | 4 | 1328 | gcatccttggcggtcttggt | 98 | 43 | 1 |
| 304758 | Coding | 4 | 1334 | ctcagtgcatccttggcggt | 97 | 44 | 1 |
| 304759 | Coding | 4 | 1336 | tgctcagtgcatccttggcg | 93 | 45 | 1 |
| 304760 | Coding | 4 | 1347 | ctcctgcacgctgctcagtg | 65 | 46 | 1 |
| 304761 | Coding | 4 | 1349 | gactcctgcacgctgctcag | 77 | 47 | 1 |
| 304762 | Coding | 4 | 1358 | gccacctgggactcctgcac | 89 | 48 | 1 |
| 304763 | Coding | 18 | 210 | gccctggcctgctgggcca | 71 | 49 | 1 |

TABLE 1 -continued

Inhibition of human apolipoprotein C-III mRNA levels by chimeric
phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 304764 | Coding | 18 | 211 | agccctggcctgctgggcc | 62 | 50 | 1 |
| 304765 | Coding | 4 | 3253 | gaagccatcggtcacccagc | 71 | 51 | 1 |
| 304766 | Coding | 4 | 3255 | ctgaagccatcggtcaccca | 85 | 52 | 1 |
| 304767 | Coding | 4 | 3265 | tttcagggaactgaagccat | 73 | 53 | 1 |
| 304768 | Coding | 4 | 3273 | cagtagtctttcagggaact | 40 | 54 | 1 |
| 304769 | Coding | 4 | 3283 | aacggtgctccagtagtctt | 66 | 55 | 1 |
| 304770 | Coding | 4 | 3287 | ccttaacggtgctccagtag | 88 | 56 | 1 |
| 304771 | Coding | 4 | 3295 | gaacttgtccttaacggtgc | 59 | 57 | 1 |
| 304772 | Coding | 4 | 3301 | ctcagagaacttgtccttaa | 88 | 58 | 1 |
| 304773 | Coding | 4 | 3305 | agaactcagagaacttgtcc | 75 | 59 | 1 |
| 304774 | Coding | 4 | 3310 | atcccagaactcagagaact | 0 | 60 | 1 |
| 304775 | Coding | 4 | 3320 | cagggtccaaatcccagaac | 70 | 61 | 1 |
| 304776 | Coding | 4 | 3332 | ttggtctgacctcagggtcc | 90 | 62 | 1 |
| 304777 | Coding | 4 | 3333 | gttggtctgacctcagggtc | 84 | 63 | 1 |
| 304778 | Coding | 4 | 3339 | gctgaagttggtctgacctc | 81 | 64 | 1 |
| 304779 | Coding | 4 | 3347 | cagccacggctgaagttggt | 75 | 65 | 1 |
| 304780 | Stop Codon | 4 | 3351 | caggcagccacggctgaagt | 83 | 66 | 1 |
| 304781 | Stop Codon | 4 | 3361 | attgaggtctcaggcagcca | 79 | 67 | 1 |
| 304782 | 3'UTR | 4 | 3385 | tggataggcaggtggacttg | 64 | 68 | 1 |
| 304783 | 3'UTR | 18 | 369 | ctcgcaggatggataggcag | 76 | 69 | 1 |
| 304784 | 3'UTR | 18 | 374 | aggagctcgcaggatggata | 58 | 70 | 1 |
| 304785 | 3'UTR | 18 | 380 | gacccaaggagctcgcagga | 73 | 71 | 1 |
| 304786 | 3'UTR | 18 | 385 | tgcagacccaaggagctcg | 92 | 72 | 1 |
| 304787 | 3'UTR | 4 | 3417 | tggagattgcaggacccaag | 88 | 73 | 1 |
| 304788 | 3'UTR | 4 | 3422 | agccctggagattgcaggac | 69 | 74 | 1 |
| 304789 | 3'UTR | 4 | 3425 | ggcagccctggagattgcag | 76 | 75 | 1 |
| 304790 | 3'UTR | 4 | 3445 | cctttaagcaacctacagg | 65 | 76 | 1 |
| 304791 | 3'UTR | 4 | 3450 | ctgtccctttaagcaacct | 53 | 77 | 1 |
| 304792 | 3'UTR | 4 | 3456 | agaatactgtccctttaag | 72 | 78 | 1 |
| 304793 | 3'UTR | 4 | 3461 | cactgagaatactgtccctt | 67 | 79 | 1 |
| 304794 | 3'UTR | 4 | 3469 | taggagagcactgagaatac | 59 | 80 | 1 |
| 304795 | 3'UTR | 4 | 3472 | gggtaggagagcactgagaa | 74 | 81 | 1 |
| 304796 | 3'UTR | 4 | 3509 | aggccagcatgcctggaggg | 63 | 82 | 1 |
| 304797 | 3'UTR | 4 | 3514 | ttgggaggccagcatgcctg | 55 | 83 | 1 |
| 304798 | 3'UTR | 4 | 3521 | agctttattgggaggccagc | 90 | 84 | 1 |
| 304799 | 3'UTR | 4 | 3526 | tgtccagctttattgggagg | 85 | 85 | 1 |
| 304800 | 3'UTR | 4 | 3528 | cttgtccagctttattggga | 94 | 86 | 1 |

TABLE 1 -continued

Inhibition of human apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 304801 | 3'UTR | 4 | 3533 | agcttcttgtccagctttat | 74 | 87 | 1 |
| 304802 | 3'UTR | 4 | 3539 | catagcagcttcttgtccag | 73 | 88 | 1 |
| 304803 | exon:intron junction | 4 | 416 | acctggagcagctgcctcta | 87 | 89 | 1 |
| 304804 | exon:intron junction | 4 | 424 | agggcattacctggagcagc | 68 | 90 | 1 |
| 304805 | intron:exon junction | 4 | 1053 | acctctgttcctgcaaggaa | 74 | 91 | 1 |
| 304806 | exon:intron junction | 4 | 1121 | aagtgcttacgggcagaggc | 78 | 92 | 1 |
| 304807 | exon:intron junction | 4 | 1380 | gcgggtgtacctggcctgct | 52 | 93 | 1 |
| 304808 | intron | 4 | 2337 | aaccctgttgtgaactgcac | 59 | 94 | 1 |
| 304809 | intron | 4 | 2405 | agtgagcaataccgcctgag | 80 | 95 | 1 |
| 304810 | intron | 4 | 2542 | cgggcttgaattaggtcagg | 56 | 96 | 1 |

As shown in Table 1, SEQ ID NOs 19, 20, 21, 22, 23, 25, 27, 28, 29, 30, 31, 32, 33, 34, 36, 37, 38, 39, 40, 41, 42, 43, 44, 45, 46, 47, 48, 49, 50, 51, 52, 53, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 and 96 demonstrated at least 45% inhibition of human apolipoprotein C-III expression in this assay and are therefore preferred. More preferred are SEQ ID NOs 75, 86 and 85. The target regions to which these preferred sequences are complementary are herein referred to as "preferred target segments" and are therefore preferred for targeting by compounds of the present invention. These preferred target segments are shown in Table 3. The sequences represent the reverse complement of the preferred antisense compounds shown in Table 1. "Target site" indicates the first (5'-most) nucleotide number on the particular target nucleic acid to which the oligonucleotide binds. Also shown in Table 3 is the species in which each of the preferred target segments was found.

Example 16

Antisense Inhibition of Mouse Apolipoprotein C-III Expression by Chimeric Phosphorothioate Oligonucleotides Having 2'-MOE Wings and a Deoxy Gap In accordance with the present invention, a second series of antisense compounds was designed to target different regions of the mouse apolipoprotein C-III RNA, using published sequences (GenBank accession number L04150.1, incorporated herein as SEQ ID NO: 11). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting often 2'-deoxynucleotides, which is flanked on both sides (5' and 3' directions) by five-nucleotide "wings". The wings are composed of 2'-O-(2-methoxyethyl)nucleotides, also known as (2'-MOE)nucleotides. The internucleoside (backbone) linkages are phosphorothioate (P=S) throughout the oligonucleotide. All cytidine residues are 5-methylcytidines. The compounds were analyzed for their effect on mouse apolipoprotein C-III mRNA levels by quantitative real-time PCR as described in other examples herein. Data are averages from three experiments in which mouse primary hepatocyte cells were treated with the antisense oligonucleotides of the present invention. If present, "N.D." indicates "no data".

TABLE 2

Inhibition of mouse apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 167858 | 5'UTR | 11 | 1 | tagggataaaactgagcagg | 47 | 97 |
| 167859 | 5'UTR | 11 | 21 | ctggagtagctagctgcttc | 30 | 98 |
| 167860 | start codon | 11 | 41 | gctgcatggcacctacgtac | 80 | 99 |
| 167861 | coding | 11 | 62 | ccacagtgaggagcgtccgg | 86 | 100 |

TABLE 2 -continued

Inhibition of mouse apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 167862 | coding | 11 | 88 | ggcagatgccaggagagcca | 55 | 101 |
| 167863 | coding | 11 | 104 | ctacctcttcagctcgggca | 56 | 102 |
| 167864 | coding | 11 | 121 | cagcagcaaggatccctcta | 83 | 103 |
| 167865 | coding | 11 | 131 | gcacagagcccagcagcaag | 49 | 104 |
| 167867 | coding | 11 | 215 | ccctggccaccgcagctata | 67 | 105 |
| 167868 | coding | 11 | 239 | atctgaagtgattgtccatc | 11 | 106 |
| 167869 | coding | 11 | 254 | agtagcctttcaggaatctg | 57 | 107 |
| 167870 | coding | 11 | 274 | cttgtcagtaaacttgctcc | 89 | 108 |
| 167871 | coding | 11 | 286 | gaagccggtgaacttgtcag | 55 | 109 |
| 167872 | coding | 11 | 294 | gaatcccagaagccggtgaa | 29 | 110 |
| 167873 | coding | 11 | 299 | ggttagaatcccagaagccg | 55 | 111 |
| 167874 | coding | 11 | 319 | tggagttggttggtcctcag | 79 | 112 |
| 167875 | stop codon | 11 | 334 | tcacgactcaatagctggag | 77 | 113 |
| 167877 | 3'UTR | 11 | 421 | cccttaaagcaaccttcagg | 71 | 114 |
| 167878 | 3'UTR | 11 | 441 | agacatgagaacatactttc | 81 | 115 |
| 167879 | 3'UTR | 11 | 471 | catgtttaggtgagatctag | 87 | 116 |
| 167880 | 3'UTR | 11 | 496 | tcttatccagctttattagg | 98 | 117 |

As shown in Table 2, SEQ ID NOs 97, 99, 100, 101, 102, 103, 104, 105, 107, 108, 109, 111, 112, 113, 114, 115, 116 and 117 demonstrated at least 45% inhibition of mouse apolipoprotein C-III expression in this experiment and are therefore preferred. More preferred are SEQ ID NOs 117, 116, and 100. The target regions to which these preferred sequences are complementary are herein referred to as "preferred target segments" and are therefore preferred for targeting by compounds of the present invention. These preferred target segments are shown in Table 3. The sequences represent the reverse complement of the preferred antisense compounds shown in Table 2. These sequences are shown to contain thymine (T) but one of skill in the art will appreciate that thymine (T) is generally replaced by uracil (U) in RNA sequences. "Target site" indicates the first (5'-most) nucleotide number on the particular target nucleic acid to which the oligonucleotide binds. Also shown in Table 3 is the species in which each of the preferred target segments was found.

TABLE 3

Sequence and position of preferred target segments identified in apolipoprotein C-III.

| SITE ID | TARGET SEQ ID NO | TARGET SITE | SEQUENCE | REV COMP OF SEQ ID | ACTIVE IN | SEQ ID NO |
|---|---|---|---|---|---|---|
| 82975 | 4 | 414 | cctagaggcagctgctccag | 19 | H. sapiens | 118 |
| 82980 | 4 | 1292 | cttctcagcttcatgcaggg | 20 | H. sapiens | 119 |
| 82981 | 18 | 141 | tgcagggttacatgaagcac | 21 | H. sapiens | 120 |
| 82985 | 4 | 1369 | ccaggtggcccagcaggcca | 22 | H. sapiens | 121 |
| 82987 | 4 | 3278 | cctgaaagactactggagca | 23 | H. sapiens | 122 |
| 220510 | 4 | 401 | tgctcagttcatccctagag | 25 | H. sapiens | 123 |
| 220512 | 18 | 17 | agaggcagctgctccaggaa | 27 | H. sapiens | 124 |
| 220513 | 18 | 24 | gctgctccaggaacagaggt | 28 | H. sapiens | 125 |
| 220514 | 18 | 29 | tccaggaacagaggtgccat | 29 | H. sapiens | 126 |

TABLE 3-continued

Sequence and position of preferred target segments identified in apolipoprotein C-III.

| SITE ID | TARGET SEQ ID NO | TARGET SITE | SEQUENCE | REV COMP OF SEQ ID | ACTIVE IN | SEQ ID NO |
|---------|------------------|-------------|----------|--------------------|-----------|-----------|
| 220515 | 4 | 1065 | acagaggtgccatgcagccc | 30 | H. sapiens | 127 |
| 220516 | 4 | 1086 | gggtactccttgttgttgcc | 31 | H. sapiens | 128 |
| 220517 | 4 | 1090 | actccttgttgttgccctcc | 32 | H. sapiens | 129 |
| 220518 | 18 | 87 | tcctggcctctgcccgagct | 33 | H. sapiens | 130 |
| 220519 | 18 | 92 | gcctctgcccgagcttcaga | 34 | H. sapiens | 131 |
| 220521 | 4 | 1267 | agcttcagaggccgaggatg | 36 | H. sapiens | 132 |
| 220522 | 4 | 1273 | agaggccgaggatgcctccc | 37 | H. sapiens | 133 |
| 220523 | 4 | 1278 | ccgaggatgcctcccttctc | 38 | H. sapiens | 134 |
| 220524 | 4 | 1281 | aggatgcctcccttctcagc | 39 | H. sapiens | 135 |
| 220525 | 4 | 1289 | tcccttctcagcttcatgca | 40 | H. sapiens | 136 |
| 220526 | 18 | 143 | cagggttacatgaagcacgc | 41 | H. sapiens | 137 |
| 220527 | 4 | 1313 | tacatgaagcacgccaccaa | 42 | H. sapiens | 138 |
| 220528 | 4 | 1328 | accaagaccgccaaggatgc | 43 | H. sapiens | 139 |
| 220529 | 4 | 1334 | accgccaaggatgcactgag | 44 | H. sapiens | 140 |
| 220530 | 4 | 1336 | cgccaaggatgcactgagca | 45 | H. sapiens | 141 |
| 220531 | 4 | 1347 | cactgagcagcgtgcaggag | 46 | H. sapiens | 142 |
| 220532 | 4 | 1349 | ctgagcagcgtgcaggagtc | 47 | H. sapiens | 143 |
| 220533 | 4 | 1358 | gtgcaggagtcccaggtggc | 48 | H. sapiens | 144 |
| 220534 | 18 | 210 | tggcccagcaggccaggggc | 49 | H. sapiens | 145 |
| 220535 | 18 | 211 | ggcccagcaggccaggggct | 50 | H. sapiens | 146 |
| 220536 | 4 | 3253 | gctgggtgaccgatggcttc | 51 | H. sapiens | 147 |
| 220537 | 4 | 3255 | tgggtgaccgatggcttcag | 52 | H. sapiens | 148 |
| 220538 | 4 | 3265 | atggcttcagttccctgaaa | 53 | H. sapiens | 149 |
| 220540 | 4 | 3283 | aagactactggagcaccgtt | 55 | H. sapiens | 150 |
| 220541 | 4 | 3287 | ctactggagcaccgttaagg | 56 | H. sapiens | 151 |
| 220542 | 4 | 3295 | gcaccgttaaggacaagttc | 57 | H. sapiens | 152 |
| 220543 | 4 | 3301 | ttaaggacaagttctctgag | 58 | H. sapiens | 153 |
| 220544 | 4 | 3305 | ggacaagttctctgagttct | 59 | H. sapiens | 154 |
| 220546 | 4 | 3320 | gttctgggatttggaccctg | 61 | H. sapiens | 155 |
| 220547 | 4 | 3332 | ggaccctgaggtcagaccaa | 62 | H. sapiens | 156 |
| 220548 | 4 | 3333 | gaccctgaggtcagaccaac | 63 | H. sapiens | 157 |
| 220549 | 4 | 3339 | gaggtcagaccaacttcagc | 64 | H. sapiens | 158 |
| 220550 | 4 | 3347 | accaacttcagccgtggctg | 65 | H. sapiens | 159 |
| 220551 | 4 | 3351 | acttcagccgtggctgcctg | 66 | H. sapiens | 160 |
| 220552 | 4 | 3361 | tggctgcctgagacctcaat | 67 | H. sapiens | 161 |
| 220553 | 4 | 3385 | caagtccacctgcctatcca | 68 | H. sapiens | 162 |

TABLE 3 -continued

Sequence and position of preferred target segments identified in apolipoprotein C-III.

| SITE ID | TARGET SEQ ID NO | TARGET SITE | SEQUENCE | REV COMP OF SEQ ID | ACTIVE IN | SEQ ID NO |
|---|---|---|---|---|---|---|
| 220554 | 18 | 369 | ctgcctatccatcctgcgag | 69 | H. sapiens | 163 |
| 220555 | 18 | 374 | tatccatcctgcgagctcct | 70 | H. sapiens | 164 |
| 220556 | 18 | 380 | tcctgcgagctccttgggtc | 71 | H. sapiens | 165 |
| 220557 | 18 | 385 | cgagctccttgggtcctgca | 72 | H. sapiens | 166 |
| 220558 | 4 | 3417 | cttgggtcctgcaatctcca | 73 | H. sapiens | 167 |
| 220559 | 4 | 3422 | gtcctgcaatctccagggct | 74 | H. sapiens | 168 |
| 220560 | 4 | 3425 | ctgcaatctccagggctgcc | 75 | H. sapiens | 169 |
| 220561 | 4 | 3445 | cctgtaggttgcttaaaagg | 76 | H. sapiens | 170 |
| 220562 | 4 | 3450 | aggttgcttaaaagggacag | 77 | H. sapiens | 171 |
| 220563 | 4 | 3456 | cttaaaagggacagtattct | 78 | H. sapiens | 172 |
| 220564 | 4 | 3461 | aaggacagtattctcagtg | 79 | H. sapiens | 173 |
| 220565 | 4 | 3469 | gtattctcagtgctctccta | 80 | H. sapiens | 174 |
| 220566 | 4 | 3472 | ttctcagtgctctcctaccc | 81 | H. sapiens | 175 |
| 220567 | 4 | 3509 | ccctccaggcatgctggcct | 82 | H. sapiens | 176 |
| 220568 | 4 | 3514 | caggcatgctggcctcccaa | 83 | H. sapiens | 177 |
| 220569 | 4 | 3521 | gctggcctcccaataaagct | 84 | H. sapiens | 178 |
| 220570 | 4 | 3526 | cctcccaataaagctggaca | 85 | H. sapiens | 179 |
| 220571 | 4 | 3528 | tcccaataaagctggacaag | 86 | H. sapiens | 180 |
| 220572 | 4 | 3533 | ataaagctggacaagaagct | 87 | H. sapiens | 181 |
| 220573 | 4 | 3539 | ctggacaagaagctgctatg | 88 | H. sapiens | 182 |
| 220574 | 4 | 416 | tagaggcagctgctccaggt | 89 | H. sapiens | 183 |
| 220575 | 4 | 424 | gctgctccaggtaatgccct | 90 | H. sapiens | 184 |
| 220576 | 4 | 1053 | ttccttgcaggaacagaggt | 91 | H. sapiens | 185 |
| 220577 | 4 | 1121 | gcctctgcccgtaagcactt | 92 | H. sapiens | 186 |
| 220578 | 4 | 1380 | agcaggccaggtacaccgc | 93 | H. sapiens | 187 |
| 220579 | 4 | 2337 | gtgcagttcacaacagggtt | 94 | H. sapiens | 188 |
| 220580 | 4 | 2405 | ctcaggcggtattgctcact | 95 | H. sapiens | 189 |
| 220581 | 4 | 2542 | cctgacctaattcaagcccg | 96 | H. sapiens | 190 |
| 82997 | 11 | 1 | cctgctcagttttatcccta | 97 | M. musculus | 191 |
| 82999 | 11 | 41 | gtacgtaggtgccatgcagc | 99 | M. musculus | 192 |
| 83000 | 11 | 62 | ccggacgctcctcactgtgg | 100 | M. musculus | 193 |
| 83001 | 11 | 88 | tggctctcctggcatctgcc | 101 | M. musculus | 194 |
| 83002 | 11 | 104 | tgcccgagctgaagaggtag | 102 | M. musculus | 195 |
| 83003 | 11 | 121 | tagagggatccttgctgctg | 103 | M. musculus | 196 |
| 83004 | 11 | 131 | cttgctgctgggctctgtgc | 104 | M. musculus | 197 |
| 83006 | 11 | 215 | tatagctgcggtggccaggg | 105 | M. musculus | 198 |
| 83008 | 11 | 254 | cagattcctgaaaggctact | 107 | M. musculus | 199 |

TABLE 3 -continued

Sequence and position of preferred target segments identified in apolipoprotein C-III.

| SITE ID | TARGET SEQ ID NO | TARGET SITE | SEQUENCE | REV COMP OF SEQ ID | ACTIVE IN | SEQ ID NO |
|---|---|---|---|---|---|---|
| 83009 | 11 | 274 | ggagcaagtttactgacaag | 108 | M. musculus | 200 |
| 83010 | 11 | 286 | ctgacaagttcaccggcttc | 109 | M. musculus | 201 |
| 83012 | 11 | 299 | cggcttctgggattctaacc | 111 | M. musculus | 202 |
| 83013 | 11 | 319 | ctgaggaccaaccaactcca | 112 | M. musculus | 203 |
| 83014 | 11 | 334 | ctccagctattgagtcgtga | 113 | M. musculus | 204 |
| 83016 | 11 | 421 | cctgaaggttgctttaaggg | 114 | M. musculus | 205 |
| 83017 | 11 | 441 | gaaagtatgttctcatgtct | 115 | M. musculus | 206 |
| 83018 | 11 | 471 | ctagatctcacctaaacatg | 116 | M. musculus | 207 |
| 83019 | 11 | 496 | cctaataaagctggataaga | 117 | M. musculus | 208 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of apolipoprotein C-III.

According to the present invention, antisense compounds include antisense oligomeric compounds, antisense oligonucleotides, ribozymes, external guide sequence (EGS) oligonucleotides, alternate splicers, primers, probes, and other short oligomeric compounds that hybridize to at least a portion of the target nucleic acid.

Example 17

Antisense Inhibition of Human Apolipoprotein C-III Expression by Chimeric Phosphorothioate Oligonucleotides Having 2'-MOE Wings and a Deoxy Gap—Additional Antisense Compounds In accordance with the present invention, an additional series of antisense compounds was designed to target different regions of the human apolipoprotein C-III RNA, using published sequences (nucleotides 6238608 to 6242565 of the sequence with GenBank accession number NT_035088.1, representing a genomic sequence, incorporated herein as SEQ ID NO: 4, and GenBank accession number NM_000040.1, incorporated herein as SEQ ID NO: 18). The compounds are shown in Table 4. "Target site" indicates the first (5'-most) nucleotide number on the particular target sequence to which the compound binds. All compounds in Table 4 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-(2-methoxyethyl)nucleotides, also known as (2'-MOE)nucleotides. The internucleoside (backbone) linkages are phosphorothioate (P=S) throughout the oligonucleotide. All cytidine residues are 5-methylcytidines. The compounds were analyzed for their effect on human apolipoprotein C-III mRNA levels by quantitative real-time PCR as described in other examples herein. Data are averages from three experiments in which HepG2 cells were treated with the antisense oligonucleotides of the present invention. If present, "N.D." indicates "no data".

TABLE 4

Inhibition of human apolipoprotein C-III mRNA levels by chimeric phosphorothioate oligonucleotides having 2'-MOE wings and a deoxy gap

| ISIS # | TARGET SEQ ID NO | TARGET SITE | SEQUENCE | % INHIB | SEQ ID NO |
|---|---|---|---|---|---|
| 167826 | 4 | 1063 | gctgcatggcacctctgttc | 0 | 209 |
| 167828 | 4 | 1110 | ggcagaggccaggagcgcca | 0 | 210 |
| 167830 | 18 | 91 | ctgaagctcgggcagaggcc | 9 | 211 |
| 167832 | 18 | 101 | tcctcggcctctgaagctcg | 0 | 212 |
| 167840 | 4 | 1315 | tcttggtggcgtgcttcatg | 0 | 213 |
| 167842 | 4 | 1335 | gctcagtgcatccttggcgg | 38 | 214 |

TABLE 4 -continued

Inhibition of human apolipoprotein C-III mRNA levels by chimeric phosphorothioate oligonucleotides having 2'-MOE wings and a deoxy gap

| ISIS # | TARGET SEQ ID NO | TARGET SITE | SEQUENCE | % INHIB | SEQ ID NO |
|---|---|---|---|---|---|
| 167844 | 4 | 1345 | cctgcacgctgctcagtgca | 28 | 215 |
| 167847 | 4 | 3256 | actgaagccatcggtcaccc | 0 | 216 |
| 167850 | 4 | 3306 | cagaactcagagaacttgtc | 0 | 217 |
| 167852 | 4 | 3336 | gaagttggtctgacctcagg | 0 | 218 |
| 167853 | 4 | 3420 | ccctggagattgcaggaccc | 0 | 219 |
| 167854 | 4 | 3426 | gggcagccctggagattgca | 22 | 220 |
| 167855 | 4 | 3446 | ccctttttaagcaacctacag | 27 | 221 |

Example 18

Antisense Inhibition of Human Apolipoprotein C-III Expression by Chimeric Phosphorothioate Oligonucleotides Having 2'-MOE Wings and a Deoxy Gap: Dose-Response Study in HepG2 Cells In accordance with the present invention, a subset of the antisense oligonucleotides from Examples 15 and 17 was further investigated in a dose-response study. Treatment doses of ISIS 167842 (SEQ ID NO: 214), ISIS 167844 (SEQ ID NO: 215), ISIS 167846 (SEQ ID NO: 22), ISIS 167837 (SEQ ID NO: 21), ISIS 304789 (SEQ ID NO: 75), ISIS 304799 (SEQ ID NO: 85), and ISIS 304800 (SEQ ID: 86) were 50, 150 and 300 nM. The compounds were analyzed for their effect on human apolipoprotein C-III mRNA levels in HepG2 cells by quantitative real-time PCR as described in other examples herein. Data are averages from two experiments and are shown in Table 5.

TABLE 5

Inhibition of human apolipoprotein C-III mRNA levels by chimeric phosphorothioate oligonucleotides having 2'-MOE wings and a deoxy gap

| | | Dose of oligonucleotide | | |
|---|---|---|---|---|
| | | 50 nM | 150 nM | 300 nM |
| ISIS # | SEQ ID NO | Percent Inhibition | | |
| 167842 | 214 | 88 | 77 | 92 |
| 167844 | 215 | 86 | 86 | 84 |
| 167846 | 22 | 79 | 80 | 79 |
| 167837 | 21 | 83 | 86 | 84 |
| 304789 | 75 | 81 | 91 | 92 |
| 304799 | 85 | 82 | 93 | 88 |
| 304800 | 86 | 80 | 86 | 91 |

These data demonstrate that the expression of apolipoprotein C-III is inhibited in a dose-dependent manner upon treatment of cells with antisense compounds targeting apolipoprotein C-III. These compounds were further analyzed in Hep3B cells for their ability to reduce mRNA levels in Hep3B cells and it was determined that ISIS 167842 and 167837 inhibited apolipoprotein C-III expression in a dose dependent manner in this cell line as well.

Example 19

Antisense Inhibition Mouse Apolipoprotein C-III Expression by Chimeric Phosphorothioate Oligonucleotides Having 2'-MOE Wings and a Deoxy Gap-Dose-Response Study in Primary Mouse Hepatocytes In accordance with the present invention, a subset of the antisense oligonucleotides in Example 16 was further investigated in dose-response studies. Treatment doses with ISIS 167861 (SEQ ID NO: 100), ISIS 167870 (SEQ ID NO: 108), ISIS 167879 (SEQ ID NO: 116), and ISIS 167880 (SEQ ID NO: 117) were 40, 120 and 240 nM. The compounds were analyzed for their effect on mouse apolipoprotein C-III mRNA levels in primary hepatocyte cells by quantitative real-time PCR as described in other examples herein. Data are averages from two experiments and are shown in Table 6.

TABLE 6

Inhibition of mouse apolipoprotein C-III mRNA levels by chimeric phosphorothioate oligonucleotides having 2'-MOE wings and a deoxy gap - dose-response study

| | | Dose of oligonucleotide | | |
|---|---|---|---|---|
| | | 40 nM | 120 nM | 240 nM |
| ISIS # | SEQ ID NO | Percent Inhibition | | |
| 167861 | 100 | 48 | 49 | 61 |
| 167870 | 108 | 16 | 16 | 46 |
| 167879 | 116 | 25 | 54 | 81 |
| 167880 | 117 | 76 | 81 | 93 |

These data demonstrate that the expression of mouse apolipoprotein C-III can be inhibited in a dose-dependent manner by treatment with antisense compounds.

Example 20

Western Blot Analysis of Apolipoprotein C-III Protein Levels

Western blot analysis (immunoblot analysis) is carried out using standard methods. Cells are harvested 16-20 h after oligonucleotide treatment, washed once with PBS, suspended in Laemmli buffer (100l/well), boiled for 5 minutes and loaded on a 16% SDS-PAGE gel. Gels are run for 1.5 hours at 150 V, and transferred to membrane for western blotting. Appropriate primary antibody directed to apolipoprotein C-III is used, with a radiolabelled or fluorescently labeled secondary antibody directed against the primary antibody species. Bands are visualized using a PHOSPHORIM-AGER™ instrument (Molecular Dynamics, Sunnyvale Calif.).

Example 21

Effects of Antisense Inhibition of Apolipoprotein C-111 (ISIS 167880) on Serum Cholesterol and Triglyceride Levels C57BL/6 mice, a strain reported to be susceptible to hyperlipidemia-induced atherosclerotic plaque formation were used in the following studies to evaluate apolipoprotein C-III antisense oligonucleotides as potential agents to lower cholesterol and triglyceride levels.

Male C57BL/6 mice (n=8) receiving a high fat diet (60% kcal fat) were evaluated over the course of 6 weeks for the effects of ISIS 167880 (SEQ ID NO: 117) on serum cholesterol and triglyceride levels. Control animals received saline treatment. Mice were dosed intraperitoneally every three days (twice a week), after fasting overnight, with 50 mg/kg ISIS 167880 or saline for six weeks.

Male C57BL/6 mice fed a normal rodent diet were fasted overnight then dosed intraperitoneally every three days with saline (control), 50 mg/kg ISIS 167880 (SEQ ID NO: 117) or 50 mg/kg ISIS 167879 (SEQ ID NO: 116) for two weeks.

At study termination, forty eight hours after the final injections, the animals were sacrificed and evaluated for serum cholesterol and triglyceride levels and compared to the saline control. Measurements of serum cholesterol and triglyceride levels were obtained through routine clinical analysis.

High fat fed mice treated with ISIS 167880 showed a reduction in both serum cholesterol (196 mg/dL for control animals and 137 mg/dL for ISIS 167880) and triglycerides (151 mg/dL for control animals and 58 mg/dL for ISIS 167880) by study end.

No effect was seen on serum cholesterol levels for lean mice treated with ISIS 167880 (91 mg/dL for control animals and 91 mg/dL for ISIS 167880), however triglycerides were lowered (91 mg/dL for control animals and 59 mg/dL for ISIS 167880) by study end.

Lean mice treated with ISIS 167879 showed an increase in serum cholesterol (91 mg/dL for control animals and 116 mg/dL for ISIS 167879) but a reduction in triglycerides (91 mg/dL for control animals and 65 mg/dL for ISIS 167879) by study end.

These results indicate that, in mice fed a high fat diet, ISIS 167880 reduces cholesterol and triglyceride to levels that are comparable to lean littermates while having no deleterious effects on the lean animals. (See Table 7 for summary of in vivo data.)

Example 22

Effects of Antisense Inhibition of Apolipoprotein C-111 (ISIS 167880) on Serum AST and ALT Levels C57BL/6 mice were used in the following studies to evaluate the liver toxicity of apolipoprotein C-III antisense oligonucleotides.

Male C57BL/6 mice (n=8) receiving a high fat diet (60% kcal fat) were evaluated over the course of 6 weeks for the effects of ISIS 167880 (SEQ ID NO: 117) on liver enzyme (AST and ALT) levels. Control animals received saline treatment. Mice were dosed intraperitoneally every three days (twice a week), after fasting overnight, with 50 mg/kg ISIS 167880 or saline for six weeks.

Male C57BL/6 mice fed a normal rodent diet were fasted overnight then dosed intraperitoneally every three days with saline (control), 50 mg/kg ISIS 167880 (SEQ ID NO: 117) or 50 mg/kg ISIS 167879 (SEQ ID NO: 116) for two weeks.

At study termination and forty-eight hours after the final injections, animals were sacrificed and evaluated for serum AST and ALT levels, which were measured by routine clinical methods. Increased levels of the liver enzymes ALT and AST can indicate toxicity and liver damage.

High fat fed mice treated with ISIS 167880 showed an increase in AST levels over the duration of the study compared to saline controls (157 IU/L for ISIS 167880, compared to 92 IU/L for saline control).

ALT levels in high fat fed mice were increased by treatments with ISIS 167880 over the duration of the study compared to saline controls (64 IU/L for ISIS 167880, compared to 40 IU/L for saline control).

Lean mice treated with ISIS 167880 showed no significant increase in AST and ALT levels over the duration of the study compared to saline controls (AST levels of 51 IU/L for control compared to 58 IU/L for ISIS 167880; ALT levels of 26 IU/L for control compared to 27 IU/L for ISIS 167880).

Lean mice treated with ISIS 167879 showed no change in AST levels and a decrease in ALT levels over the duration of the study compared to saline controls (AST levels of 51 IU/L for control compared to 51 IU/L for ISIS 167879; ALT levels of 26 IU/L for control compared to 21 IU/L for ISIS 167879).

These results suggest a minor liver toxicity effect from ISIS 167880 in mice fed a high fat diet but no liver toxicity from ISIS 167880 or 167879 in mice fed a normal rodent diet. (See Table 7 for summary of in vivo data.)

Example 23

Effects of Antisense Inhibition of Apolipoprotein C-111 (ISIS 167880) on Serum Glucose Levels Male C57BL/6 mice (n=8) receiving a high fat diet (60% kcal fat) were evaluated over the course of 6 weeks for the effects of ISIS 167880 (SEQ ID NO: 117) on serum glucose levels. Control animals received saline treatment. Mice were dosed intraperitoneally every three days (twice a week), after fasting overnight, with 50 mg/kg ISIS 167880 or saline for six weeks.

Male C57BL/6 mice fed a normal rodent diet were fasted overnight then dosed intraperitoneally every three days with saline (control), 50 mg/kg ISIS 167880 (SEQ ID NO: 117) or 50 mg/kg ISIS 167879 (SEQ ID NO: 116) for two weeks.

At study termination and forty-eight hours after the final injections, animals were sacrificed and evaluated for serum glucose levels, which was measured by routine clinical methods.

In the high fat fed mice, ISIS 167880 reduced serum glucose levels to 183 mg/dL, compared to the saline control of 213 mg/dL. In lean mice, ISIS 167880 had no significant effect on serum glucose levels with measurements of 203 mg/dL, compared to the saline control of 204 mg/dL; while ISIS 167879 only slightly increased serum glucose levels to 216 mg/dL.

These results indicate that, in mice fed a high fat diet, ISIS 167880 is able to reduce serum glucose to levels comparable to lean littermates, while having no deleterious effects on the lean animals. (See Table 7 for summary of in vivo data.)

Example 24

Effects of Antisense Inhibition of Apolipoprotein C-111 (ISIS 167880) on Apolipoprotein C-III mRNA Levels in C57BL/6 Mice Male C57BL/6 mice received a high fat diet (60% kcal fat) fasted overnight, and dosed intraperitoneally every three days with saline or 50 mg/kg ISIS 167880 (SEQ ID NO: 117) for six weeks.

Male C57BL/6 mice fed a normal rodent diet were fasted overnight then dosed intraperitoneally every three days with saline (control) or 50 mg/kg ISIS 167880 (SEQ ID NO: 117) or 50 mg/kg ISIS 167879 (SEQ ID NO: 116) for two weeks.

At study termination, forty-eight hours after the final injections, animals were sacrificed and evaluated for apolipoprotein C-III mRNA levels in liver. The high fat fed mice dosed with ISIS 167880 had apolipoprotein C-III mRNA levels 8% that of the saline treated mice. The lean mice showed decreased apolipoprotein C-III mRNA after treatment with either ISIS 167880 or ISIS 167879. The lean mice dosed with ISIS 167880 had apolipoprotein C-III mRNA levels 21% that of the saline treated mice and those dosed with ISIS 167879 had apolipoprotein C-III mRNA levels 27% that of the saline treated mice.

These results indicate that in both high fat fed mice and lean mice, antisense oligonucleotides directed against apolipoprotein C-III are able to decrease apolipoprotein C-III mRNA levels in vivo to a similar extent. (See Table 7 for summary of in vivo data.)

TABLE 7

Effects of ISIS 167880 or 167879 treatment on cholesterol, triglyceride, glucose, liver enzyme, and apolipoprotein C-III mRNA in liver, in lean and high fat fed C57BL/6 mice.

| | Biological Marker Measured units | ISIS # | Diet, Experiment duration | |
|---|---|---|---|---|
| | | | High Fat, 6 week | Lean, 2 week |
| | Cholesterol mg/dL | control | 196 | 91 |
| | | 167880 | 137 | 91 |
| | | 167879 | N.D. | 116 |
| | Triglycerides mg/dL | control | 151 | 91 |
| | | 167880 | 58 | 59 |
| | | 167879 | N.D. | 65 |
| | Glucose mg/dL | control | 213 | 204 |
| | | 167880 | 183 | 203 |
| | | 167879 | N.D. | 216 |
| Liver Enzymes | AST IU/L | control | 92 | 51 |
| | | 167880 | 157 | 58 |
| | | 167879 | N.D. | 51 |
| | ALT IU/L | control | 40 | 26 |
| | | 167880 | 64 | 27 |
| | | 167879 | N.D. | 21 |
| | Apolipoprotein C-III mRNA % of control | 167880 | 8% | 21% |
| | | 167879 | N.D. | 27% |

In summary, these results indicate that, in mice fed a high fat diet, ISIS 167880 is able to reduce serum glucose, cholesterol and triglyceride to levels comparable to lean littermates, while having no deleterious effects on the lean animals. Furthermore, antisense oligonucleotides directed against apolipoprotein C-III are able to decrease apolipoprotein C-III mRNA levels in vivo to a similar extent in both high fat fed mice and lean mice. These results suggest a minor liver toxicity effect from ISIS 167880 in mice fed a high fat diet but no liver toxicity from ISIS 167880 or 167879 in mice fed a normal rodent diet.

Example 25

Antisense Inhibition of Apolipoprotein C-III mRNA In Vivo

C57BL/6 mice, a strain reported to be susceptible to hyperlipidemia-induced atherosclerotic plaque formation, were used in the following studies to evaluate apolipoprotein C-III antisense oligonucleotides as potential agents to lower cholesterol and triglyceride levels. Accordingly, in a further embodiment, C57BL/6 mice on a high-fat diet were treated with antisense oligonucleotides targeted to apolipoprotein C-III.

Male C57BL/6 mice (n=8; 7 to 8 weeks of age) receiving a high fat diet (60% kcal fat) were evaluated for apolipoprotein C-III mRNA expression in liver after 6 weeks of treatment with antisense oligonucleotides targeted to apolipoprotein C-III. Mice received twice weekly intraperitoneal injections at a dose of 25 mg/kg of ISIS 167880 (SEQ ID NO: 117), ISIS 167875 (SEQ ID NO: 113), ISIS 167878 (SEQ ID NO: 115) or ISIS 167879 (SEQ ID NO: 116). Control animals received saline treatment twice weekly for a period of 6 weeks.

At study termination, forty-eight hours after the final injections, the animals were sacrificed and evaluated for apolipoprotein C-III mRNA expression in liver. RNA was isolated from liver and mRNA was quantitated as described herein. Apolipoprotein C-III mRNA levels from each treatment group (n=8) were averaged. Relative to saline-treated animals, treatment with ISIS 167875, ISIS 167878, ISIS 167879 and ISIS 167880 resulted in a 24%, 56%, 50% and 77% reduction in apolipoprotein C-III mRNA levels, respectively, demonstrating that these compounds significantly reduced apolipoprotein C-III mRNA expression in liver.

Example 26

Effects of Antisense Inhibition of Apolipoprotein C-III on Serum Cholesterol, Triglyceride, Glucose and Serum Transaminases In a further embodiment, the mice treated with saline or a 25 mg/kg dose of ISIS 167880 (SEQ ID NO: 117), ISIS 167875 (SEQ ID NO: 113), ISIS 167878 (SEQ ID NO: 115) or ISIS 167879 (SEQ ID NO: 116) as described in Example 25 were evaluated for serum cholesterol and triglyceride levels following 6 weeks of treatment.

At study termination, forty-eight hours after the dose of saline or antisense compound, the animals were sacrificed and evaluated for serum cholesterol, triglyceride and glucose levels by routine analysis using an Olympus Clinical Analyzer (Olympus America Inc., Melville, N.Y.). The serum transaminases ALT and AST, increases in which can indicate hepatotoxicity, were also measured using an Olympus Clinical Analyzer (Olympus America Inc., Melville, N.Y.). The levels of serum cholesterol, triglycerides and glucose are presented in Table 8 as the average result from each treatment group (n=8), in mg/dL. ALT and AST, also shown in Table 8, are also shown as the average result from each treatment group (n=8), in international units/L (IU/L).

TABLE 8

Effects of antisense inhibition of apolipoprotein C-III on serum cholesterol, triglyceride, glucose and transaminases

| Serum marker | Treatment | | | | |
|---|---|---|---|---|---|
| | Saline | ISIS 167875 | ISIS 167878 | ISIS 167879 | ISIS 167880 |
| Total Cholesterol mg/dL | 172 | 197 | 180 | 132 | 155 |
| HDL Cholesterol mg/dL | 149 | 162 | 157 | 117 | 137 |
| LDL Cholesterol mg/dL | 25 | 37 | 28 | 24 | 21 |
| Serum Triglyerides mg/dL | 126 | 99 | 75 | 60 | 52 |
| ALT IU/L | 24 | 555 | 32 | 45 | 66 |
| AST IU/L | 56 | 489 | 76 | 117 | 132 |
| Glucose mg/dL | 273 | 234 | 251 | 189 | 255 |

A significant reduction in serum triglyceride levels was observed following treatment with ISIS 167875, ISIS 167878, ISIS 167879 and ISIS 167880, which reduced triglyercide levels 22%, 40%, 52% and 58%, respectively. This reduction in serum triglycerides correlated with the reduction in apolipoprotein C-III liver mRNA expression. Moreover, reductions in target and serum triglycerides following treatment with ISIS 167878, ISIS 167879 and ISIS 167880 were not accompanied by hepatoxicity, as indicated by the lack of significant increases in ALT and AST levels. Glucose levels were significantly lowered following treatment with ISIS 167879.

Example 27

Effects of Antisense Inhibition of Apolipoprotein C-III on Body Weight and Organ Weight In a further embodiment, the animals treated with saline or a 25 mg/kg dose of ISIS 167880 (SEQ ID NO: 117), ISIS 167875 (SEQ ID NO: 113), ISIS 167878 (SEQ ID NO: 115) or ISIS 167879 (SEQ ID NO: 116) as described in Example 25 were evaluated for changes in body weight, fat pad, liver and spleen weights. At study termination, forty-eight hours following the final dose of saline or antisense compound, the animals were sacrificed and body and organ weights were measured. The data shown in Table 9 represent average weights from all animals in each treatment group (n=8). Body weight is presented in grams (g), while spleen, liver and fat pad weights are presented in milligrams (mg).

TABLE 9

Effects of antisense inhibition of apolipoprotein C-III on body and organ weights

| | Treatment | | | | |
|---|---|---|---|---|---|
| | Saline | ISIS 167875 | ISIS 167878 | ISIS 167879 | ISIS 167880 |
| Body weight (g) | 33 | 30 | 32 | 28 | 30 |
| Liver weight (mg) | 126 | 190 | 141 | 133 | 146 |
| Fat pad weight (mg) | 182 | 125 | 125 | 61 | 62 |
| Spleen weight (mg) | 8 | 12 | 12 | 12 | 14 |

As is evident in Table 9, treatment with antisense compounds targeted to mouse apolipoprotein C-III resulted in significant reductions in fat pad weight. ISIS 167875 and ISIS 167878 both led to a 31% reduction in fat pad weight, while ISIS 167879 and ISIS 167880 both resulted in a 66% lowering of fat pad weight. Body weights were not significantly changed and spleen weights were slightly increased following antisense compound treatment. With the exception livers from animals treated with ISIS 167875, liver weights were not significantly changed.

Example 28

Effects of Antisense Inhibition of Apolipoprotein C-III on Liver Triglyceride Levels Hepatic steatosis refers to the accumulation of lipids in the liver, or "fatty liver", which is frequently caused by alcohol consumption, diabetes and hyperlipidemia and can progress to end-stage liver damage. Given the deleterious consequences of a fatty liver condition, it is of use to identify compounds that prevent or ameliorate hepatic steatosis. Hepatic steatosis is evaluated both by measurement of tissue triglyceride content and by histologic examination of liver tissue.

In a further embodiment, liver tissue triglyceride content was assessed in the animals treated with saline or a 25 mg/kg dose of ISIS 167880 (SEQ ID NO: 117), ISIS 167875 (SEQ ID NO: 113), ISIS 167878 (SEQ ID NO: 115) or ISIS 167879 (SEQ ID NO: 116) as described in Example 25. Liver tissue triglyceride content was measured using the Triglyceride GPO assay (Roche Diagnostics, Indianapolis, Ind.). Histological analysis was conducted by routine procedures, whereby liver tissue was fixed in neutral-buffered formalin, embedded in paraffin, sectioned and subsequently stained with hematoxylin and eosin, to visualize nuclei and cytoplasm, respectively. Alternatively, liver tissue was procured then immediately frozen, sectioned, and subsequently stained with oil red O stain to visualize lipid deposits and counterstained with eosin to mark cytoplasm. The prepared samples were evaluated by light microscopy.

Relative to saline treated mice, liver tissue triglyceride levels were significantly lowered, by 25%, 35%, 40% and 64% following treatment with ISIS 167875, ISIS 167878, ISIS 167879 and ISIS 167880, respectively. Histological analysis of stained liver sections similarly revealed a reduction in liver tissue triglycerides. Thus, as demonstrated by measurement of tissue triglycerides and histological analyses of liver tissue sections, treatment with antisense compounds targeted to apolipoprotein C-III reduced liver triglyceride content. As such, antisense compounds targeted to apolipoprotein C-III are candidate therapeutic agents for the prevention or amelioration of hepatic steatosis.

Example 29

Antisense Inhibition of Apolipoprotein C-III in Cynomolgus Monkey Primary Hepatocytes In a further embodiment, antisense compounds targeted to human apolipoprotein C-III were tested for their effects on apolipoprotein C-III expression in primary Cynomolgus monkey hepatocytes. Pre-plated primary Cynomolgus monkey hepatocytes were purchased from InVitro Technologies (Baltimore, Md.). Cells were cultured in high-glucose DMEM (Invitrogen Life Technologies, Carlsbad, Calif.) supplemented with 10% fetal bovine serum (Invitrogen Life Technologies, Carlsbad, Calif.), 100 units/mL and 100 μg/mL streptomycin (Invitrogen Life Technologies, Carlsbad, Calif.).

Cells at a density of 80,000 cells per well in a 24-well plate were treated with 10, 50, 150 and 300 nM of ISIS 304789 (SEQ ID NO: 75), ISIS 304799 (SEQ ID NO: 85) or ISIS 304800 (SEQ ID NO: 86). ISIS 113529 (CTCTTACTGT-GCTGTGGACA, SEQ ID NO: 222) served as a control oligonucleotide. ISIS 113529 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-O-(2-methoxyethyl) nucleotides, also known as (2'-MOE)nucleotides. The internucleoside (backbone) linkages are phosphorothioate (P=S) throughout the oligonucleotide. All cytidine residues are 5-methylcytidines.

Following 24 hours of treatment with antisense oligonucleotides, apolipoprotein C-III mRNA was measured by real-time PCR as described by other examples herein, using the primers and probe designed to the human apolipoprotein C-III sequence (SEQ ID NOs 5, 6 and 7) to measure Cynomolgous monkey apolipoprotein C-III mRNA. Primers and probe designed to human GAPDH (SEQ ID NOs 8, 9 and 10) were used to measure Cynomolgous monkey GAPDH mRNA expression, for the purpose of normalizing gene target quantities obtained by real-time PCR. Untreated cells served as the control to which data were normalized. Data are the average of three experiments and are presented in Table 10.

TABLE 10

Antisense inhibition of apolipoprotein C-III in Cynomolgus monkey primary hepatocytes

| | | Dose of Oligonucleotide | | | |
| --- | --- | --- | --- | --- | --- |
| ISIS # | SEQ ID NO | 10 nM | 50 nM | 150 nM | 300 nM |
| | | % Inhibition | | | |
| 304789 | 75 | 0 | 7 | 1 | 55 |
| 304799 | 85 | 34 | 60 | 66 | 48 |
| 304800 | 86 | 9 | 53 | 59 | 57 |
| 113529 | 222 | N.D. | N.D. | 0 | 0 |

Example 30

Cynomolgus Monkey Apolipoprotein C-III Sequence

In a further embodiment, a portion of the Cynomolgus monkey apolipoprotein C-III gene was sequenced. Positions 8 to 476 of the human apolipoprotein C-III mRNA sequence (incorporated in its entirety herein as SEQ ID NO: 18) contain the target segment to which ISIS 304789 hybridizes. The corresponding region of Cynomolgus monkey apolipoprotein C-III mRNA was sequenced. RNA was isolated and purified from primary Cynomolgus monkey hepatocytes (InVitro Technologies, Gaithersburg, Md.) and was subjected to a reverse transcriptase reaction (kit from Invitrogen Life Technologies, Carlsbad, Calif.). The resultant cDNA was the substrate for 40 rounds of PCR amplification, using 5' and 3' primers designed to positions 8 and 476, respectively, of the human apolipoprotein C-III mRNA (Amplitaq PCR kit, Invitrogen Life Technologies, Carlsbad, Calif.). Following gel purification of the resultant 468 bp fragment, the forward and reverse sequencing reactions of each product were performed by Retrogen (San Diego, Calif.). This Cynomolgus monkey sequence is incorporated herein as SEQ ID NO: 223 and is 92% identical to positions 8 to 476 of the human apolipoprotein C-III mRNA.

Example 31

Chimeric Phosphorothioate Oligonucleotide Having 2'-MOE Wings and a Deoxy Gap, Targeted to Cynomolgus Monkey Apolipoprotein C-III In a further embodiment, the sequence of Cynomolgus monkey apolipoprotein C-III incorporated herein as SEQ ID NO: 223 was used to design an antisense oligonucleotide having 100% complementarity to Cynomolgus apolipoprotein C-III mRNA. ISIS 340340 (GGCAGCCCTGGAGGCT-GCAG; incorporated herein as SEQ ID NO: 224) targets nucleotide 397 of SEQ ID NO: 223, within a region corresponding to the 3' UTR of the human apolipoprotein C-III to which ISIS 304789 hybridizes. ISIS 340340 is a chimeric oligonucleotide ("gapmer") 20 nucleotide in length composed of a central "gap" region consisting of 2'deoxynucleotides, which is flanked on both sides (5' and 3' directions) by 5 nucleotide "wings". The wings are composed of 2'methoxyethyl (2'-MOE) nucleotides. Internucleoside (backbone) linkages are phosphorothioate (P=S) throughout the nucleotide. All cytidine residues are 5-methyl cytidines.

Example 32

Antisense Inhibition of Rat Apolipoprotein C-III Expression by Chimeric Phosphorothioate Oligonucleotides Having 2'-MOE Wings and a Deoxy Gap In a further embodiment, for the purpose of designing antisense oligonucleotides to both coding and untranslated regions of rat apolipoprotein C-III mRNA, a segment of rat apolipoprotein C-III mRNA was sequenced to provide 3' UTR sequence, as the published rat apolipoprotein C-III mRNA sequence is restricted to the coding region. RNA was isolated and purified from primary rat hepatocytes (InVitro Technologies, Gaithersburg, Md.) and was subjected to a reverse transcriptase reaction (kit from Invitrogen Life Technologies, Carlsbad, Calif.). The resultant cDNA was the substrate for 40 rounds of PCR amplification (Amplitaq PCR kit, Invitrogen Life Technologies, Carlsbad, Calif.), using forward and reverse primers that anneal to the 5'-most and 3'-most ends, respectively, of mouse apolipoprotein C-III mRNA. Following gel purification of the resultant 427 bp fragment, the forward and reverse sequencing reactions of each product were performed by Retrogen (San Diego, Calif.). This rat sequence is incorporated herein as SEQ ID NO: 225 and includes an additional 121 bp in the 3' direction from the stop codon of apolipoprotein C-III, with respect to the published sequence (GenBank accession number NM_012501.1, incorporated herein as SEQ ID NO: 226).

A series of antisense compounds was designed to target different regions of the rat apolipoprotein C-III mRNA, using SEQ ID NO: 225. The compounds are shown in Table 11. "Target site" indicates the first (5'-most) nucleotide number on the particular target sequence to which the compound binds. All compounds in Table 11 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-(2-methoxyethyl)nucleotides, also known as (2'-MOE)nucleotides. The internucleoside (backbone) linkages are phosphorothioate (P=S) throughout the oligonucleotide. All cytidine residues are 5-methylcytidines.

The compounds were analyzed for their effect on rat apolipoprotein C-III mRNA levels by quantitative real-time PCR as described in other examples herein. Probes and primers to rat apolipoprotein C-III were designed to hybridize to a rat apolipoprotein C-III sequence, using published sequence information (GenBank accession number NM_012501.1, incorporated herein as SEQ ID NO: 226). For rat apolipoprotein C-III the PCR primers were:
forward primer: GAGGGAGAGGGATCCTTGCT (SEQ ID NO: 227)
reverse primer: GGACCGTCTTGGAGGCTTG (SEQ ID NO: 228)
and the PCR probe was: FAM-CTGGGCTCTATG-CAGGGCTACATGGA-TAMRA, SEQ ID NO: 229) where FAM is the fluorescent dye and TAMRA is the quencher dye.
For rat GAPDH the PCR primers were:
forward primer: TGTTCTAGAGACAGCCGCATCTT (SEQ ID NO: 230)
reverse primer: CACCGACCTTCACCATCTTGT (SEQ ID NO: 231)
and the PCR probe was JOE-TTGTGCAGTGCCAGC-CTCGTCTCA-TAMRA (SEQ ID NO: 232) where JOE is the fluorescent reporter dye and TAMRA is the quencher dye.

Data are from an experiment in which primary rat hepatocytes were treated with 150 nM of the antisense oligonucleotides of the invention. Results, shown in Table 11, are expressed as percent inhibition relative to untreated control cells. If present, "N.D." indicates "no data".

TABLE 11

Antisense inhibition of rat apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 340982 | Coding | 225 | 213 | TGAACTTATCAGTGAACTTG | 0 | 233 |
| 340987 | Coding | 225 | 238 | TCAGGGCCAGACTCCCAGAG | 7 | 234 |
| 340988 | Coding | 225 | 258 | TTGGTGTTGTTAGTTGGTCC | 0 | 235 |
| 340991 | Coding | 225 | 258 | TTGGTGTTGTTAGTTGGTCC | 0 | 236 |
| 353932 | Coding | 225 | 10 | AGAGCCACGAGGGCCACGAT | 0 | 237 |
| 353933 | Coding | 225 | 20 | AGAGGCCAGGAGAGCCACGA | 15 | 238 |
| 353934 | Coding | 225 | 30 | CAGCTCGGGCAGAGGCCAGG | 2 | 239 |
| 353935 | Coding | 225 | 40 | TCTCCCTCATCAGCTCGGGC | 0 | 240 |
| 353936 | Coding | 225 | 59 | GCCCAGCAGCAAGGATCCCT | 73 | 241 |
| 353937 | Coding | 225 | 69 | CCTGCATAGAGCCCAGCAGC | 0 | 242 |
| 353938 | Coding | 225 | 79 | TCCATGTAGCCCTGCATAGA | 90 | 243 |
| 353940 | Coding | 225 | 99 | GGACCGTCTTGGAGGCTTGT | 76 | 244 |
| 353941 | Coding | 225 | 109 | AGTGCATCCTGGACCGTCTT | 61 | 245 |
| 353942 | Coding | 225 | 119 | CATGCTGCTTAGTGCATCCT | 0 | 246 |
| 353943 | Coding | 225 | 129 | CAGACTCCTGCATGCTGCTT | 57 | 247 |
| 353944 | Coding | 225 | 139 | ACAGCTATATCAGACTCCTG | 0 | 248 |
| 353945 | Coding | 225 | 148 | CTGGCCACCACAGCTATATC | 0 | 249 |
| 353946 | Coding | 225 | 169 | AAGCGATTGTCCATCCAGCC | 0 | 250 |
| 353949 | Coding | 225 | 195 | TGCTCCAGTAGCCTTTCAGG | 0 | 251 |
| 353950 | Coding | 225 | 200 | GAACTTGCTCCAGTAGCCTT | 35 | 252 |
| 353951 | Coding | 225 | 204 | CAGTGAACTTGCTCCAGTAG | 0 | 253 |
| 353952 | Coding | 225 | 209 | CTTATCAGTGAACTTGCTCC | 0 | 254 |
| 353953 | Coding | 225 | 217 | CCAGTGAACTTATCAGTGAA | 0 | 255 |

TABLE 11 -continued

Antisense inhibition of rat apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 353954 | Coding | 225 | 221 | GAGGCCAGTGAACTTATCAG | 0 | 256 |
| 353955 | Coding | 225 | 224 | CCAGAGGCCAGTGAACTTAT | 31 | 257 |
| 353956 | Coding | 225 | 229 | GACTCCCAGAGGCCAGTGAA | 0 | 258 |
| 353957 | Coding | 225 | 234 | GGCCAGACTCCCAGAGGCCA | 0 | 259 |
| 353958 | Coding | 225 | 247 | AGTTGGTCCTCAGGGCCAGA | 0 | 260 |
| 353959 | Coding | 225 | 250 | GTTAGTTGGTCCTCAGGGCC | 0 | 261 |
| 353960 | Coding | 225 | 254 | TGTTGTTAGTTGGTCCTCAG | 0 | 262 |
| 353961 | Coding | 225 | 262 | AGAGTTGGTGTTGTTAGTTG | 0 | 263 |
| 353962 | Coding | 225 | 267 | GCTCAAGAGTTGGTGTTGTT | 0 | 264 |
| 353963 | Coding | 225 | 271 | CACGGCTCAAGAGTTGGTGT | 0 | 265 |
| 353964 | Stop Codon | 225 | 275 | GTCTCACGGCTCAAGAGTTG | 0 | 266 |
| 353966 | Stop Codon | 225 | 285 | GAACATGGAGGTCTCACGGC | 55 | 267 |
| 353967 | Stop Codon | 225 | 289 | TCTGGAACATGGAGGTCTCA | 0 | 268 |
| 353968 | 3'UTR | 225 | 293 | CACATCTGGAACATGGAGGT | 0 | 269 |
| 353969 | 3'UTR | 225 | 297 | CAGACACATCTGGAACATGG | 0 | 270 |
| 353970 | 3'UTR | 225 | 301 | TGGCCAGACACATCTGGAAC | 49 | 271 |
| 353972 | 3'UTR | 225 | 309 | AGGATAGATGGCCAGACACA | 47 | 272 |
| 353973 | 3'UTR | 225 | 313 | CAGCAGGATAGATGGCCAGA | 0 | 273 |
| 353974 | 3'UTR | 225 | 317 | GAGGCAGCAGGATAGATGGC | 38 | 274 |
| 353975 | 3'UTR | 225 | 321 | TTCGGAGGCAGCAGGATAGA | 0 | 275 |
| 353976 | 3'UTR | 225 | 325 | AACCTTCGGAGGCAGCAGGA | 19 | 276 |
| 353977 | 3'UTR | 225 | 329 | GAGCAACCTTCGGAGGCAGC | 88 | 277 |
| 353978 | 3'UTR | 225 | 333 | CTTAGAGCAACCTTCGGAGG | 77 | 278 |
| 353979 | 3'UTR | 225 | 337 | TCCCCTTAGAGCAACCTTCG | 0 | 279 |
| 353980 | 3'UTR | 225 | 341 | ACTTTCCCCTTAGAGCAACC | 45 | 280 |
| 353981 | 3'UTR | 225 | 345 | ATATACTTTCCCCTTAGAGC | 28 | 281 |
| 353982 | 3'UTR | 225 | 349 | GAGAATATACTTTCCCCTTA | 96 | 282 |
| 353983 | 3'UTR | 225 | 353 | GCATGAGAATATACTTTCCC | 69 | 283 |
| 353984 | 3'UTR | 225 | 357 | AAAGGCATGAGAATATACTT | 47 | 284 |
| 353985 | 3'UTR | 225 | 361 | GGATAAAGGCATGAGAATAT | 0 | 285 |
| 353986 | 3'UTR | 225 | 365 | GGAGGGATAAAGGCATGAGA | 0 | 286 |
| 353987 | 3'UTR | 225 | 386 | GCATGTTTAGGTGAGGTCTG | 100 | 287 |
| 353988 | 3'UTR | 225 | 390 | GACAGCATGTTTAGGTGAGG | 0 | 288 |
| 353990 | 3'UTR | 225 | 398 | TTATTTGGGACAGCATGTTT | 0 | 289 |
| 353991 | 3'UTR | 225 | 402 | GCTTTTATTTGGGACAGCAT | 0 | 290 |
| 353992 | 3'UTR | 225 | 407 | TCCCAGCTTTTATTTGGGAC | 22 | 291 |

In a further embodiment, an additional series of oligonucleotides was designed to target different regions of the rat apolipoprotein C-III RNA, using sequences described herein (SEQ ID NO: 225 and the sequence with Genbank accession number NM_012501.1, incorporated herein as SEQ ID NO: 226). The oligonucleotides are shown in Table 12. "Target site" indicates the first (5'-most) nucleotide number on the particular target sequence to which the oligonucleotide binds. All compounds in Table 12 are chimeric oligonucleotides ("gapmers") 20 nucleotides in length, composed of a central "gap" region consisting of eight 2'-deoxynucleotides, which is flanked on both sides (5' and 3' directions) by 3-nucleotide "wings." The wings are composed of 2'-O-(2-methoxyethyl) nucleotides, also known as (2'-MOE)nucleotides. The internucleoside (backbone) linkages are phosphorothioate (P=S) throughout the oligonucleotide. All cytidine residues are 5-methylcytidines.

TABLE 12

Chimeric phosphorothioate oligonucleotides having 2'-MOE wings and a deoxy gap targeted to rat apolipoprotein C-III mRNA

| ISIS # | REGION | TARGET SEQ ID NO | TARGET SITE | SEQUENCE | SEQ ID NO |
| --- | --- | --- | --- | --- | --- |
| 340937 | Coding | 226 | 8 | CACGATGAGGAGCATTCGGG | 292 |
| 340938 | Coding | 226 | 13 | AGGGCCACGATGAGGAGCAT | 293 |
| 340939 | Coding | 225 | 6 | CCACGAGGGCCACGATGAGG | 294 |
| 340940 | Coding | 225 | 11 | GAGAGCCACGAGGGCCACGA | 295 |
| 340941 | Coding | 225 | 16 | GCCAGGAGAGCCACGAGGGC | 296 |
| 340942 | Coding | 225 | 21 | CAGAGGCCAGGAGAGCCACG | 297 |
| 340943 | Coding | 225 | 26 | TCGGGCAGAGGCCAGGAGAG | 298 |
| 340944 | Coding | 225 | 31 | TCAGCTCGGGCAGAGGCCAG | 299 |
| 340945 | Coding | 225 | 36 | CCTCATCAGCTCGGGCAGAG | 300 |
| 340946 | Coding | 225 | 41 | CTCTCCCTCATCAGCTCGGG | 301 |
| 340947 | Coding | 225 | 46 | GATCCCTCTCCCTCATCAGC | 302 |
| 340948 | Coding | 225 | 51 | GCAAGGATCCCTCTCCCTCA | 303 |
| 340949 | Coding | 225 | 56 | CAGCAGCAAGGATCCCTCTC | 304 |
| 340950 | Coding | 225 | 61 | GAGCCCAGCAGCAAGGATCC | 305 |
| 340951 | Coding | 225 | 66 | GCATAGAGCCCAGCAGCAAG | 306 |
| 340952 | Coding | 225 | 71 | GCCCTGCATAGAGCCCAGCA | 307 |
| 340953 | Coding | 225 | 76 | ATGTAGCCCTGCATAGAGCC | 308 |
| 340954 | Coding | 225 | 81 | GTTCCATGTAGCCCTGCATA | 309 |
| 340955 | Coding | 225 | 86 | GGCTTGTTCCATGTAGCCCT | 310 |
| 340956 | Coding | 225 | 91 | TTGGAGGCTTGTTCCATGTA | 311 |
| 340957 | Coding | 225 | 96 | CCGTCTTGGAGGCTTGTTCC | 312 |
| 340958 | Coding | 225 | 101 | CTGGACCGTCTTGGAGGCTT | 313 |
| 340959 | Coding | 225 | 106 | GCATCCTGGACCGTCTTGGA | 314 |
| 340960 | Coding | 225 | 111 | TTAGTGCATCCTGGACCGTC | 315 |
| 340961 | Coding | 225 | 116 | GCTGCTTAGTGCATCCTGGA | 316 |
| 340962 | Coding | 225 | 121 | TGCATGCTGCTTAGTGCATC | 317 |
| 340963 | Coding | 225 | 126 | ACTCCTGCATGCTGCTTAGT | 318 |
| 340964 | Coding | 225 | 131 | ATCAGACTCCTGCATGCTGC | 319 |
| 340965 | Coding | 225 | 136 | GCTATATCAGACTCCTGCAT | 320 |
| 340966 | Coding | 225 | 141 | CCACAGCTATATCAGACTCC | 321 |
| 340967 | Coding | 225 | 146 | GGCCACCACAGCTATATCAG | 322 |

TABLE 12 -continued

Chimeric phosphorothioate oligonucleotides having 2'-MOE wings and a deoxy gap targeted to rat apolipoprotein C-III mRNA

| ISIS # | REGION | TARGET SEQ ID NO | TARGET SITE | SEQUENCE | SEQ ID NO |
|---|---|---|---|---|---|
| 340968 | Coding | 226 | 163 | CTGCTGGCCACCACAGCTAT | 323 |
| 340969 | Coding | 226 | 168 | AGCCCCTGCTGGCCACCACA | 324 |
| 340970 | Coding | 226 | 173 | CATCCAGCCCCTGCTGGCCA | 325 |
| 340971 | Coding | 226 | 178 | TTGTCCATCCAGCCCCTGCT | 326 |
| 340972 | Coding | 226 | 179 | ATTGTCCATCCAGCCCCTGC | 327 |
| 340973 | Coding | 225 | 168 | AGCGATTGTCCATCCAGCCC | 328 |
| 340974 | Coding | 225 | 173 | TTTGAAGCGATTGTCCATCC | 329 |
| 340975 | Coding | 225 | 178 | AGGGATTTGAAGCGATTGTC | 330 |
| 340976 | Coding | 225 | 183 | CTTTCAGGGATTTGAAGCGA | 331 |
| 340977 | Coding | 225 | 188 | GTAGCCTTTCAGGGATTTGA | 332 |
| 340978 | Coding | 225 | 193 | CTCCAGTAGCCTTTCAGGGA | 333 |
| 340979 | Coding | 225 | 198 | ACTTGCTCCAGTAGCCTTTC | 334 |
| 340980 | Coding | 225 | 203 | AGTGAACTTGCTCCAGTAGC | 335 |
| 340981 | Coding | 225 | 208 | TTATCAGTGAACTTGCTCCA | 336 |
| 340983 | Coding | 225 | 218 | GCCAGTGAACTTATCAGTGA | 337 |
| 340984 | Coding | 225 | 223 | CAGAGGCCAGTGAACTTATC | 338 |
| 340985 | Coding | 225 | 228 | ACTCCCAGAGGCCAGTGAAC | 339 |
| 340986 | Coding | 225 | 233 | GCCAGACTCCCAGAGGCCAG | 340 |
| 340989 | Coding | 225 | 248 | TAGTTGGTCCTCAGGGCCAG | 341 |
| 340990 | Coding | 225 | 253 | GTTGTTAGTTGGTCCTCAGG | 342 |
| 340992 | Coding | 225 | 263 | AAGAGTTGGTGTTGTTAGTT | 343 |
| 340993 | Coding | 225 | 268 | GGCTCAAGAGTTGGTGTTGT | 344 |
| 340994 | Stop Codon | 225 | 272 | TCACGGCTCAAGAGTTGGTG | 345 |
| 353939 | Coding | 225 | 89 | GGAGGCTTGTTCCATGTAGC | 346 |
| 353947 | Coding | 225 | 180 | TCAGGGATTTGAAGCGATTG | 347 |
| 353948 | Coding | 225 | 190 | CAGTAGCCTTTCAGGGATTT | 348 |
| 353965 | Stop Codon | 225 | 281 | ATGGAGGTCTCACGGCTCAA | 349 |
| 353971 | 3' UTR | 225 | 305 | TAGATGGCCAGACACATCTG | 350 |
| 353989 | 3' UTR | 225 | 394 | TTGGGACAGCATGTTTAGGT | 351 |

Example 33

Antisense Inhibition of Rat Apolipoprotein C-III by Chimeric Phosphorothioate Oligonucleotides Having 2'-MOE Wings and a Deoxy Gap: Dose Response Study in Primary Rat Hepatocytes In a further embodiment, four oligonucleotides were selected for additional dose response studies. Primary rat hepatocytes were treated with 10, 50, 150, and 300 nM of ISIS 167878 (SEQ ID NO: 115), ISIS 167880 (SEQ ID NO: 117), ISIS 340982 (SEQ ID NO: 233), or the scrambled control oligo ISIS 113529 (SEQ ID NO: 222) and mRNA levels were measured 24 hours after oligonucleotide treatment as described in other examples herein. Untreated cells served as the control to which the data were normalized.

Results of these studies are shown in Table 13. Data are averages from three experiments and are expressed as percent inhibition, relative to untreated controls. Where present, "N.D." indicates "no data".

TABLE 13

Antisense inhibition of apolipoprotein C-III mRNA expression in primary rat hepatocytes 24 hours after oligonucleotide treatment

| | | Dose of oligonucleotide | | | |
|---|---|---|---|---|---|
| ISIS # | SEQ ID NO | 10 nM | 50 nM | 150 nM | 300 nM |
| | | | % Inhibition | | |
| 167878 | 115 | 0 | 0 | 0 | 4 |
| 167880 | 117 | 21 | 19 | 20 | 33 |
| 340982 | 233 | 15 | 70 | 83 | 91 |
| 113529 | 222 | N.D. | N.D. | N.D. | 9 |

As shown in Table 13, ISIS 340982 was effective at reducing apolipoprotein C-III mRNA levels in a dose-dependent manner.

Example 34

Antisense Inhibition of Rat Apolipoprotein C-III by Chimeric Phosphorothioate Oligonucleotides Having 2'-MOE Wings and a Deoxy Gap: Additional Dose Response Study in Primary Rat Hepatocytes In a further embodiment, an additional group of antisense oligonucleotides targeted to rat apolipoprotein C-III was selected for dose response studies. Primary rat hepatocytes were treated with 10, 50, 150 and 300 nM of ISIS 353977 (SEQ ID NO: 277), ISIS 353978 (SEQ ID NO: 278), ISIS 353982 (SEQ ID NO: 282), ISIS 353983 (SEQ ID NO: 283), or ISIS 353987 (SEQ ID NO: 287) for a period of 24 hours. Target expression levels were quantitated by real-time PCR as described herein. Untreated cells served as the control to which data were normalized. The results, shown in Table 14, are the average of three experiments and are presented as percent inhibition of apolipoprotein C-III mRNA, relative to untreated control cells.

TABLE 14

Dose-dependent inhibition of apolipoprotein C-III mRNA expression in primary rat hepatocytes 24 hours after oligonucleotide treatment

| | | Dose of oligonucleotide | | | |
|---|---|---|---|---|---|
| ISIS # | SEQ ID NO | 10 nM | 50 nM | 150 nM | 300 nM |
| | | | % Inhibition | | |
| 353977 | 277 | 26 | 10 | 3 | 2 |
| 353978 | 278 | 46 | 23 | 8 | 5 |
| 353982 | 282 | 35 | 21 | 10 | 2 |
| 353983 | 283 | 46 | 23 | 12 | 2 |
| 353987 | 287 | 38 | 25 | 12 | 4 |

These data demonstrate that ISIS 353977, ISIS 353978, ISIS 353982, ISIS 353983, and ISIS 353987 effectively reduce apolipoprotein C-III mRNA in a dose-dependent manner.

Example 35

Antisense Inhibition of Rat Apolipoprotein C-III In Vivo: mRNA Levels

In a further embodiment, the effects of antisense inhibition of apolipoprotein C-III in rats were evaluated. Male Sprague-Dawley rats 6 weeks of age (Charles River Labs, Wilmington, Mass.) were fed a normal rodent diet. Animals received intra-peritoneal injections of ISIS 340982 (SEQ ID NO: 233) twice weekly for two weeks. One group of animals (n=4) received 75 mg/kg ISIS 340982 and one group of animals (n=4) received 100 mg/kg ISIS 340982. Saline-treated animals (n=4) served as a control group.

At the end of the treatment period, animals were sacrificed and RNA was isolated from liver. Apolipoprotein C-III mRNA was measured as described by other examples herein. Results from each treatment group were averaged and the mRNA levels in livers from ISIS 340982-treated mice were normalized to the mRNA levels in livers from saline-treated mice. Treatment with 75 mg/kg or 100 mg/kg ISIS 340982 resulted in a 69% reduction and an 84% reduction in liver apolipoprotein C-III mRNA, respectively, demonstrating that ISIS 340982 effectively inhibited target mRNA expression in vivo.

Example 36

Effects of Antisense Inhibition of Rat Apolipoprotein C-III In Vivo: Body, Liver and Spleen Weights In a further embodiment, the rats treated with ISIS 340782 (SEQ ID NO: 233) as described in Example 35 were assessed for changes in body, liver and spleen weights. Body weights were recorded at the initiation of the study (Week 0). Following the two-week treatment with twice-weekly injections of saline or ISIS 340782 at 75 or 100 mg/kg, animals were sacrificed, forty-eight hours after the fourth and final injections, the animals were sacrificed. Body, liver and spleen weights were recorded at study termination.

TABLE 15

Body, liver and spleen weights in rats treated with antisense oligonucleotide targeted to apolipoprotein C-III

| | | | Treatment with ISIS 340892 | | | |
|---|---|---|---|---|---|---|
| | Saline | | 75 mg/kg | | 100 mg/kg | |
| Measurement | Week 0 | Week 2 | Week 0 | Week 2 | Week 0 | Week 2 |
| Body weight (g) | 529 | 536 | 485 | 448 | 478 | 425 |
| Liver weight (g) | N.D. | 19 | N.D. | 14 | N.D. | 16 |
| Spleen weight (mg) | N.D. | 1.1 | N.D. | 1.6 | N.D. | 1.6 |

These data demonstrate that antisense inhibition of apolipoprotein C-III mRNA was not associated with significant changes in body, liver or spleen weight.

Example 37

Effects of Antisense Inhibition of Rat Apolipoprotein C-III In Vivo: Blood Lipids and Glucose Levels In a further embodiment, the rats treated as described in Example 35 were evaluated for changes in blood total cholesterol, triglycerides, HDL-cholesterol, LDL-cholesterol, free fatty acids and glucose. Blood samples were collected just prior to the treatments (Week 0) and following the two week treatment with twice weekly injections of saline or ISIS 340982 (SEQ ID NO: 233) at 75 or 100 mg/kg. Total cholesterol, HDL-cholesterol, LDL-cholesterol, triglyceride, free fatty acid and glucose levels were measured by routine clinical methods using an Olympus Clinical Analyzer (Olympus America Inc., Melville, N.Y.). Data from the four animals in each treatment group were averaged. The results are presented in Table 16.

TABLE 16

Effects of antisense inhibition of rat apolipoprotein C-III on blood lipids and glucose

| Biological Marker Measured | Treatment | | | | | |
|---|---|---|---|---|---|---|
| | Saline | | 75 mg/kg ISIS 340982 | | 100 mg/kg ISIS 340982 | |
| | Week 0 | Week 2 | Week 0 | Week 2 | Week 0 | Week 2 |
| Triglycerides Mg/dL | 162 | 162 | 111 | 24 | 139 | 17 |
| Total Cholesterol Mg/dL | 112 | 102 | 106 | 40 | 107 | 31 |
| HDL-Cholesterol Mg/dL | 66 | 63 | 83 | 23 | 96 | 17 |
| LDL-Cholesterol Mg/dL | 29 | 32 | 35 | 13 | 37 | 10 |
| Free Fatty Acids mEq/L | 0.48 | 0.46 | 0.72 | 0.70 | 0.57 | 0.53 |
| Glucose Mg/dL | 153 | 151 | 147 | 127 | 164 | 166 |

From the data presented in Table 16 it is evident that ISIS 340982 treatment, at both doses administered, to significantly reduced circulating triglycerides, total cholesterol, HDL-cholesterol and LDL-cholesterol in rats. Furthermore, these animals exhibited reduced expression of apolipoprotein C-III mRNA in liver following treatment with ISIS 340982.

Example 38

Effects of Antisense Inhibition of Rat Apolipoprotein C-III In Vivo: Serum Transaminases In a further embodiment, the rats treated as described in Example 35 were evaluated for liver toxicity following antisense oligonucleotide treatment. Following the two week treatment with twice weekly injections of 75 mg/kg and 100 mg/kg ISIS 340982 (SEQ ID NO: 233), animals were sacrificed and blood was collected and processed for routine clinical analysis. The serum transaminases ALT and AST, increases in which can indicate hepatotoxicity, were also measured using an Olympus Clinical Analyzer (Olympus America Inc., Melville, N.Y.). ALT and AST levels, shown in Table 17, are shown as the average result from the 4 animals in each treatment group, in international units/L (IU/L).

TABLE 17

Effects of treatment with ISIS 340982 on serum transaminase levels in rats

| Serum Transaminase | Treatment | | |
|---|---|---|---|
| | Saline | 75 mg/kg ISIS 340982 | 100 mg/kg ISIS 340982 |
| ALT IU/L | 70 | 49 | 59 |
| AST IU/L | 93 | 127 | 147 |

ALT or AST levels twice that of the saline control are considered indicative of hepatotoxicity. These data demonstrate that ISIS 340982 treatment of rats, either at a dose of 75 mg/kg or 100 mg/kg, did not result in significant hepatotoxicity.

Example 39

Antisense Inhibition of Hamster Apolipoprotein C-III Expression by Chimeric Phosphorothioate Oligonucleotides Having 2'-MOE Wings and a Deoxy Gap In a further embodiment, for the purpose of designing antisense oligonucleotides to different regions of hamster apolipoprotein C-III mRNA, a segment of *Mesocricetus auratus* hamster apolipoprotein C-III mRNA was sequenced to provide a segment of coding region and 3' UTR sequence, as no published sequence of hamster apolipoprotein C-III mRNA was available. RNA was isolated and purified from primary hamster hepatocytes and was subjected to a reverse transcriptase reaction (kit from Invitrogen Life Technologies, Carlsbad, Calif.). The resultant cDNA was the substrate for 40 rounds of PCR amplification (Amplitaq PCR kit, Invitrogen Life Technologies, Carlsbad, Calif.) using forward and reverse primers complementary to the 5' and 3' ends, respectively, of the mouse apolipoprotein C-III mRNA sequence. Following gel purification of the resultant 435 bp fragment, the forward and reverse sequencing reactions of each product were performed by Retrogen (San Diego, Calif.). This hamster sequence is incorporated herein as SEQ ID NO: 352.

A series of oligonucleotides was designed to target regions of the hamster apolipoprotein C-III mRNA (SEQ ID NO: 352). The oligonucleotides are shown in Table 18. "Target site" indicates the first (5'-most) nucleotide number on the particular target sequence to which the oligonucleotide binds. All compounds in Table 18 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-O-(2-methoxyethyl) nucleotides, also known as (2'-MOE)nucleotides. The internucleoside (backbone) linkages are phosphorothioate (P=S) throughout the oligonucleotide. All cytidine residues are 5-methylcytidines.

The compounds were analyzed for their effect on hamster apolipoprotein C-III levels in primary hamster hepatocytes by quantitative real-time PCR as described in other examples herein. Probes and primers to hamster apolipoprotein C-III were designed to hybridize to a hamster apolipoprotein C-III sequence, using the hamster mRNA sequence described herein (SEQ ID NO: 352). For hamster apolipoprotein CIII the PCR primers were:
forward primer: CGCTAACCAGCATGCAAAAG (SEQ ID NO: 353)
reverse primer: CACCGTCCATCCAGTCCC(SEQ ID NO: 354) and the PCR probe was: FAM-CTGAGGTGGCTGT-GCGGGCC-TAMRA
(SEQ ID NO: 355) where FAM is the fluorescent dye and TAMRA is the quencher dye.
For hamster GAPDH the PCR primers were:
forward primer: CCAGCCTCGCTCCGG (SEQ ID NO: 356)
reverse primer: CCAATACGGCCAAATCCG (SEQ ID NO: 357)
and the PCR probe was JOE-ACGCAATGGTGAAGGTCG-GCG-TAMRA (SEQ ID NO: 358) where JOE is the fluorescent reporter dye and TAMRA is the quencher dye.

Data are from an experiment in which primary hamster hepatocytes were treated with 150 nM of the oligonucleotides of the present invention. The data, shown in Table 18, are normalized to untreated control cells. If present, "N.D." indicates "no data."

TABLE 18

Antisense inhibition of hamster apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 352929 | Coding | 352 | 5 | TGCCAAGAGGGCAACAATAG | 17 | 359 |
| 352930 | Coding | 352 | 10 | AGGAGTGCCAAGAGGGCAAC | 62 | 360 |
| 352931 | Coding | 352 | 16 | GATGCCAGGAGTGCCAAGAG | 50 | 361 |
| 352932 | Coding | 352 | 20 | GGCAGATGCCAGGAGTGCCA | 51 | 362 |
| 352933 | Coding | 352 | 39 | CTCTACCTCATTAGCTTCGG | 0 | 363 |
| 352934 | Coding | 352 | 41 | CCCTCTACCTCATTAGCTTC | 47 | 364 |
| 352935 | Coding | 352 | 44 | GACCCCTCTACCTCATTAGC | 0 | 365 |
| 352936 | Coding | 352 | 49 | GCAAGGACCCCTCTACCTCA | 15 | 366 |
| 352937 | Coding | 352 | 54 | CAGCAGCAAGGACCCCTCTA | 45 | 367 |
| 352938 | Coding | 352 | 59 | GAGCCCAGCAGCAAGGACCC | 0 | 368 |
| 352939 | Coding | 352 | 65 | TGCACAGAGCCCAGCAGCAA | 84 | 369 |
| 352940 | Coding | 352 | 70 | AGCCCTGCACAGAGCCCAGC | 0 | 370 |
| 352941 | Coding | 352 | 75 | CATGTAGCCCTGCACAGAGC | 0 | 371 |
| 352942 | Coding | 352 | 80 | TGTTCCATGTAGCCCTGCAC | 49 | 372 |
| 352943 | Coding | 352 | 85 | TGGCCTGTTCCATGTAGCCC | 55 | 373 |
| 352945 | Coding | 352 | 95 | ACCTTCTTGGTGGCCTGTTC | 62 | 374 |
| 352946 | Coding | 352 | 106 | GCGCATCCTGGACCTTCTTG | 0 | 375 |
| 352948 | Coding | 352 | 115 | TGCTGGTTAGCGCATCCTGG | 0 | 376 |
| 352949 | Coding | 352 | 120 | TTGCATGCTGGTTAGCGCAT | 3 | 377 |
| 352950 | Coding | 352 | 125 | GACTTTTGCATGCTGGTTAG | 59 | 378 |
| 352951 | Coding | 352 | 130 | CCTCAGACTTTTGCATGCTG | 72 | 379 |
| 352952 | Coding | 352 | 135 | AGCCACCTCAGACTTTTGCA | 75 | 380 |
| 352953 | Coding | 352 | 140 | CGCACAGCCACCTCAGACTT | 64 | 381 |
| 352955 | Coding | 352 | 153 | CCAGTCCCTGGCCCGCACAG | 66 | 382 |
| 352956 | Coding | 352 | 159 | GTCCATCCAGTCCCTGGCCC | 73 | 383 |
| 352957 | Coding | 352 | 161 | CCGTCCATCCAGTCCCTGGC | 0 | 384 |
| 352958 | Coding | 352 | 165 | GCCACCGTCCATCCAGTCCC | 0 | 385 |
| 352959 | Coding | 352 | 170 | GTGAAGCCACCGTCCATCCA | 12 | 386 |
| 352960 | Coding | 352 | 174 | GGAGGTGAAGCCACCGTCCA | 0 | 387 |
| 352961 | Coding | 352 | 193 | TGCTCCAGTAGCTTTTCAGG | 59 | 388 |
| 352962 | Coding | 352 | 200 | GTAAATGTGCTCCAGTAGCT | 66 | 389 |
| 352963 | Coding | 352 | 205 | TGTCAGTAAATGTGCTCCAG | 78 | 390 |
| 352965 | Coding | 352 | 214 | TGGAGACCGTGTCAGTAAAT | 38 | 391 |
| 352966 | Coding | 352 | 217 | GGCTGGAGACCGTGTCAGTA | 66 | 392 |
| 352967 | Coding | 352 | 221 | CAGAGGCTGGAGACCGTGTC | 13 | 393 |
| 352968 | Coding | 352 | 225 | ATCCCAGAGGCTGGAGACCG | 0 | 394 |
| 352969 | Coding | 352 | 230 | GAAGAATCCCAGAGGCTGGA | 54 | 395 |

TABLE 18 -continued

Antisense inhibition of hamster apolipoprotein C-III mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|--------|--------|------------------|-------------|----------|---------|-----------|
| 352970 | Coding | 352 | 269 | TCTCAAGGCTCAGTAGCTGG | 0 | 396 |
| 352971 | Coding | 352 | 275 | TAGAGGTCTCAAGGCTCAGT | 70 | 397 |
| 352972 | Stop Codon | 352 | 280 | GAACGTAGAGGTCTCAAGGC | 61 | 398 |
| 352973 | Stop Codon | 352 | 286 | CATTTGGAACGTAGAGGTCT | 64 | 399 |
| 352974 | 3' UTR | 352 | 292 | CAAGCACATTTGGAACGTAG | 0 | 400 |
| 352975 | 3' UTR | 352 | 300 | TGGACACACAAGCACATTTG | 0 | 401 |
| 352976 | 3' UTR | 352 | 305 | CAGGATGGACACACAAGCAC | 43 | 402 |
| 352977 | 3' UTR | 352 | 311 | GGCCAGCAGGATGGACACAC | 81 | 403 |
| 352978 | 3' UTR | 352 | 318 | GCCCAGAGGCCAGCAGGATG | 60 | 404 |
| 352979 | 3' UTR | 352 | 348 | CCTTTCAAACAACCTTCAGG | 56 | 405 |
| 352980 | 3' UTR | 352 | 402 | GGACAGCATGTTTAGGTGAC | 67 | 406 |

In a further embodiment, an additional series of oligonucleotides was designed to target different regions of the hamster apolipoprotein C-III RNA described herein (SEQ ID NO: 352). The oligonucleotides are shown in Table 19. "Target site" indicates the first (5'-most) nucleotide number on the particular target sequence to which the oligonucleotide binds. All compounds in Table 19 are chimeric oligonucleotides ("gapmers") 20 nucleotides in length, composed of a central "gap" region consisting of eight 2'-deoxynucleotides, which is flanked on both sides (5' and 3' directions) by 3-nucleotide "wings." The wings are composed of 2'-O-(2-methoxyethyl) nucleotides, also known as (2'-MOE)nucleotides. The internucleoside (backbone) linkages are phosphorothioate (P=S) throughout the oligonucleotide. All cytidine residues are 5-methylcytidines.

TABLE 19

Chimeric phosphorothioate oligonucleotides having 2'-MOE wings and a deoxy gap targeted to hamster apolipoprotein C-III mRNA

| ISIS # | REGION | TARGET SEQ ID NO | TARGET SITE | SEQUENCE | SEQ ID NO |
|--------|--------|------------------|-------------|----------|-----------|
| 352944 | Coding | 352 | 90 | CTTGGTGGCCTGTTCCATGT | 407 |
| 352947 | Coding | 352 | 110 | GTTAGCGCATCCTGGACCTT | 408 |
| 352954 | Coding | 352 | 145 | TGGCCCGCACAGCCACCTCA | 409 |
| 352964 | Coding | 352 | 210 | GACCGTGTCAGTAAATGTGC | 410 |
| 356295 | Coding | 352 | 1 | AAGAGGGCAACAATAGGAGT | 411 |
| 356296 | Coding | 352 | 6 | GTGCCAAGAGGGCAACAATA | 412 |
| 356297 | Coding | 352 | 15 | ATGCCAGGAGTGCCAAGAGG | 413 |
| 356298 | Coding | 352 | 25 | CTTCGGGCAGATGCCAGGAG | 414 |
| 356299 | Coding | 352 | 31 | CATTAGCTTCGGGCAGATGC | 415 |
| 356300 | Coding | 352 | 60 | AGAGCCCAGCAGCAAGGACC | 416 |
| 356301 | Coding | 352 | 86 | GTGGCCTGTTCCATGTAGCC | 417 |
| 356302 | Coding | 352 | 91 | TCTTGGTGGCCTGTTCCATG | 418 |
| 356303 | Coding | 352 | 96 | GACCTTCTTGGTGGCCTGTT | 419 |
| 356304 | Coding | 352 | 101 | TCCTGGACCTTCTTGGTGGC | 420 |

TABLE 19 -continued

Chimeric phosphorothioate oligonucleotides having 2'-MOE wings and a deoxy gap targeted to hamster apolipoprotein C-III mRNA

| ISIS # | REGION | TARGET SEQ ID NO | TARGET SITE | SEQUENCE | SEQ ID NO |
|---|---|---|---|---|---|
| 356305 | Coding | 352 | 111 | GGTTAGCGCATCCTGGACCT | 421 |
| 356306 | Coding | 352 | 116 | ATGCTGGTTAGCGCATCCTG | 422 |
| 356307 | Coding | 352 | 121 | TTTGCATGCTGGTTAGCGCA | 423 |
| 356308 | Coding | 352 | 126 | AGACTTTTGCATGCTGGTTA | 424 |
| 356309 | Coding | 352 | 131 | ACCTCAGACTTTTGCATGCT | 425 |
| 356310 | Coding | 352 | 136 | CAGCCACCTCAGACTTTTGC | 426 |
| 356311 | Coding | 352 | 141 | CCGCACAGCCACCTCAGACT | 427 |
| 356312 | Coding | 352 | 146 | CTGGCCCGCACAGCCACCTC | 428 |
| 356313 | Coding | 352 | 151 | AGTCCCTGGCCCGCACAGCC | 429 |
| 356314 | Coding | 352 | 156 | CATCCAGTCCCTGGCCCGCA | 430 |
| 356315 | Coding | 352 | 166 | AGCCACCGTCCATCCAGTCC | 431 |
| 356316 | Coding | 352 | 171 | GGTGAAGCCACCGTCCATCC | 432 |
| 356317 | Coding | 352 | 176 | AGGGAGGTGAAGCCACCGTC | 433 |
| 356318 | Coding | 352 | 181 | TTTTCAGGGAGGTGAAGCCA | 434 |
| 356319 | Coding | 352 | 187 | AGTAGCTTTTCAGGGAGGTG | 435 |
| 356320 | Coding | 352 | 198 | AAATGTGCTCCAGTAGCTTT | 436 |
| 356321 | Coding | 352 | 203 | TCAGTAAATGTGCTCCAGTA | 437 |
| 356322 | Coding | 352 | 208 | CCGTGTCAGTAAATGTGCTC | 438 |
| 356323 | Coding | 352 | 213 | GGAGACCGTGTCAGTAAATG | 439 |
| 356324 | Coding | 352 | 218 | AGGCTGGAGACCGTGTCAGT | 440 |
| 356325 | Coding | 352 | 223 | CCCAGAGGCTGGAGACCGTG | 441 |
| 356326 | Coding | 352 | 228 | AGAATCCCAGAGGCTGGAGA | 442 |
| 356327 | Stop Codon | 352 | 274 | AGAGGTCTCAAGGCTCAGTA | 443 |
| 356328 | Stop Codon | 352 | 279 | AACGTAGAGGTCTCAAGGCT | 444 |
| 356329 | Stop Codon | 352 | 284 | TTTGGAACGTAGAGGTCTCA | 445 |
| 356330 | 3' UTR | 352 | 289 | GCACATTTGGAACGTAGAGG | 446 |
| 356331 | 3' UTR | 352 | 294 | CACAAGCACATTTGGAACGT | 447 |
| 356332 | 3' UTR | 352 | 299 | GGACACACAAGCACATTTGG | 448 |
| 356333 | 3' UTR | 352 | 304 | AGGATGGACACACAAGCACA | 449 |
| 356334 | 3' UTR | 352 | 309 | CCAGCAGGATGGACACACAA | 450 |
| 356335 | 3' UTR | 352 | 314 | AGAGGCCAGCAGGATGGACA | 451 |
| 356336 | 3' UTR | 352 | 319 | GGCCCAGAGGCCAGCAGGAT | 452 |
| 356337 | 3' UTR | 352 | 324 | ACCCAGGCCCAGAGGCCAGC | 453 |
| 356338 | 3' UTR | 352 | 329 | GGGCCACCCAGGCCCAGAGG | 454 |
| 356339 | 3' UTR | 352 | 353 | CTTTCCCTTTCAAACAACCT | 455 |
| 356340 | 3' UTR | 352 | 358 | CAATACTTTCCCTTTCAAAC | 456 |
| 356341 | 3' UTR | 352 | 363 | CATGACAATACTTTCCCTTT | 457 |

TABLE 19 -continued

Chimeric phosphorothioate oligonucleotides having 2'-MOE wings and a deoxy gap targeted to hamster apolipoprotein C-III mRNA

| ISIS # | REGION | TARGET SEQ ID NO | TARGET SITE | SEQUENCE | SEQ ID NO |
|---|---|---|---|---|---|
| 356342 | 3' UTR | 352 | 368 | GAAAACATGACAATACTTTC | 458 |
| 356343 | 3' UTR | 352 | 373 | GGGATGAAAACATGACAATA | 459 |
| 356344 | 3' UTR | 352 | 396 | CATGTTTAGGTGACTTCTGG | 460 |
| 356345 | 3' UTR | 352 | 401 | GACAGCATGTTTAGGTGACT | 461 |
| 356346 | 3' UTR | 352 | 406 | TTTAGGACAGCATGTTTAGG | 462 |
| 356347 | 3' UTR | 352 | 411 | CTTTATTTAGGACAGCATGT | 463 |
| 356348 | 3' UTR | 352 | 416 | TCCAGCTTTATTTAGGACAG | 464 |

Example 40

Antisense Inhibition of Hamster Apolipoprotein C-III by Chimeric Phosphorothioate Oligonucleotides Having 2'-MOE Wings and a Deoxy Gap: Dose Response Studies in Primary Hamster Hepatocytes In a further embodiment, six oligonucleotides targeted to hamster apolipoprotein C-III were selected for additional dose response studies. Primary hamster hepatocytes were treated with 50, 150, and 300 nM of ISIS 352939 (SEQ ID NO: 369), ISIS 352952 (SEQ ID NO: 380), ISIS 352962 (SEQ ID NO: 389), ISIS 352963 (SEQ ID NO: 390), ISIS 352971 (SEQ ID NO: 397), or ISIS 352977 (SEQ ID NO: 403) and mRNA levels were measured 24 hours after oligonucleotide treatment as described in other examples herein. Untreated cells served as the control to which the data were normalized.

Results of these studies are shown in Table 20. Data are averages from three experiments and are expressed as percent inhibition, relative to untreated controls.

TABLE 20

Inhibition of apolipoprotein C-III mRNA expression in primary hamster hepatocytes 24 hours after oligonucleotide treatment

| | | Dose of oligonucleotide | | |
|---|---|---|---|---|
| ISIS # | SEQ ID NO | 50 nM | 150 nM | 300 nM |
| | | % Inhibition | | |
| 352939 | 369 | 46 | 64 | 82 |
| 352952 | 380 | 59 | 68 | 60 |
| 352962 | 389 | 84 | 0 | 22 |
| 352963 | 390 | 0 | 0 | 42 |
| 352971 | 397 | 0 | 27 | 0 |
| 352977 | 403 | 48 | 72 | 56 |

As shown in Table 20, ISIS 352939 was effective at reducing hamster apolipoprotein C-III mRNA levels in a dose-dependent manner.

Example 41

Antisense Oligonucleotides Targeted to Mouse Apolipoprotein C-III

In a further embodiment, additional antisense oligonucleotides targeting mouse apolipoprotein C-III were designed using published sequence information (GenBank accession number L04150.1, incorporated herein as SEQ ID NO: 11). Both target nucleotide position 496 of SEQ ID NO: 11, as does ISIS 167880 (SEQ ID NO: 117), but vary in chemical composition relative to ISIS 167880. ISIS 340995 is 20 nucleotides in length, composed of a central gap region 10 nucleotides in length, wherein the gap contains both 2' deoxynucleotides and 2'-MOE (MOE)nucleotides. The nucleotide composition is shown in Table 21, where 2'-MOE nucleotides are indicated in bold type, and 2' deoxynucleotides are underscored. The gap is flanked on both sides (5' and 3' ends) by 5 nucleotide "wings" composed of 2'-MOE nucleotides. ISIS 340997 (SEQ ID NO: 117) is 20 nucleotides in length and uniformly composed of 2'-MOE nucleotides. Throughout both ISIS 340995 and ISIS 340997, internucleoside (backbone) linkages are phosphorothioate and all cytidines residues are unmodified cytidines.

TABLE 21

Antisense oligonucleotides targeted to mouse apolipoprotein C-III

| ISISNO | Region | Target SEQ ID NO | Target Site | SEQUENCE | SEQ NO ID |
|---|---|---|---|---|---|
| 340995 | 3' UTR | 11 | 496 | TCTTATCCAGCTTTATTAGG | 117 |
| 340997 | 3' UTR | 11 | 496 | TCTTATCCAGCTTTATTAGG | 117 |

What is claimed is:

1. A method for identifying a modified antisense compound having the potential for treating a subject with a disease or condition associated with the expression of apolipoprotein C-III levels, comprising:
   (a) obtaining a modified antisense compound comprising at least one modified internucleoside linkage, sugar moiety or nucleobase, wherein the modified antisense compound targets a nucleic acid region corresponding to the 5' cap site, the 5' untranslated region, the translation initiation codon region, the coding region, the translation termination codon region or the 3' untranslated region of apolipoprotein C-III;
   (b) treating an animal with the antisense compound; and
   (c) comparing the amount of reduction in apolipoprotein C-III expression levels in the treated animal to apolipoprotein C-III expression levels in an untreated animal;
   wherein, if the reduction of levels in the treated animal in (c) is at least 50%, the antisense compound is identified as having the potential for treating a subject with a disease or condition associated with the expression of apolipoprotein C-III.

2. The method of claim 1, wherein the modified antisense compound additionally is tested for its ability to reduce apolipoprotein C-III levels by a method comprising:
   (1) treating a cell, tissue or organ with the modified antisense compound; and
   (2) comparing the amount of reduction in apolipoprotein C-III levels in the treated cell, tissue or organ to apolipoprotein C-III levels in an untreated cell, tissue or organ; thereby determining whether the antisense compound has the ability to reduce apolipoprotein C-III levels in the cell, tissue or organ.

3. The method of claim 2, wherein a cell is treated in (1), and the cell is HepG2.

4. The method of claim 2, wherein a cell is treated in (1), and the cell is a monkey cell.

5. The method of claim 2, wherein a cell is treated in (1), and the cell is a hepatocyte.

6. The method of claim 2, wherein a tissue is treated in (1), and the tissue is blood.

7. The method of claim 2, wherein there is at least a 45% reduction in apolipoprotein C-III mRNA levels after (1) and (2).

8. The method of claim 2, wherein the antisense compound is administered in (1) at a concentration ranging from 50 to 300 nM.

9. The method of claim 1, wherein the animal is a mouse.

10. The method of claim 1, wherein the animal is a rat.

11. The method of claim 1, wherein the subject is a human.

12. The method of claim 1, further comprising determining whether the antisense compound reduces triglyceride, glucose and/or cholesterol levels in an animal when the antisense compound is administered to the animal, compared to the levels in the absence of the antisense compound.

13. The method of claim 1, wherein the reduction in apolipoprotein C-III expression levels comprises a reduction in mRNA levels of apolipoprotein C-III.

14. The method of claim 1, wherein the modified antisense compound targets a nucleic acid region corresponding to the coding region or the 3' untranslated region of apolipoprotein C-III.

15. The method of claim 1, further comprising determining whether the antisense compound is toxic to the animal.

16. The method of claim 1, further comprising determining whether the antisense compound increases ALT and/or AST liver enzyme levels.

\* \* \* \* \*

SEQUENCE LISTING

<160> NUMBER OF SEQ ID NOS: 468

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
tccgtcatcg ctcctcaggg                                                  20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
gtgcgcgcga gcccgaaatc                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
atgcattctg cccccaagga                                                  20

<210> SEQ ID NO 4
<211> LENGTH: 3958
<212> TYPE: DNA
<213> ORGANISM: H. sapiens
<220> FEATURE:

<400> SEQUENCE: 4
ctactccagg ctgtgttcag ggcttgggc tggtggaggg aggggcctga aattccagtg        60
tgaaaggctg agatgggccc gaggcccctg gcctatgtcc aagccatttc ccctctcacc      120
agcctctccc tggggagcca gtcagctagg aaggaatgag ggctccccag gcccacccc       180 agttcctgag ctcatctggg ctgcagggct ggcgggacag cagcgtggac tcagtctcct      240
agggatttcc caactctccc gcccgcttgc tgcatctgga cacccctgcct caggccctca    300 tctccactgg tcagcaggtg acctttgccc agcgccctgg gtcctcagtg cctgctgccc    360
tggagatgat ataaaacagg tcagaaccct cctgcctgtc tgctcagttc atccctagag    420
gcagctgctc caggtaatgc cctctgggga ggggaaagag gaggggagga ggatgaagag    480
gggcaagagg agctccctgc ccagcccagc cagcaagcct ggagaagcac ttgctagagc    540
taaggaagcc tcggagctgg acgggtgccc cccacccctc atcataacct gaagaacatg    600
gaggcccggg aggggtgtca cttgcccaaa gctacatagg gggtggggct ggaagtggct    660
ccaagtgcag gttccccccct cattcttcag gcttagggct ggaggaagcc ttagacagcc    720
cagtcctacc ccagacaggg aaactgaggc ctggagaggg ccagaaatca cccaaagaca    780
cacagcatgt tggctggact ggacggagat cagtccagac cgcaggtgcc ttgatgttca    840
gtctggtggg ttttctgctc catcccaccc acctcccttt gggcctcgat ccctcgcccc    900
tcaccagtcc cccttctgag agcccgtatt agcagggagc cggcccctac tccttctggc    960

| | | | | |
|---|---|---|---|---|
| agacccagct | aaggttctac | cttaggggcc | acgccacctc | cccagggagg ggtccagagg | 1020 |
| catgggacc | tggggtgccc | ctcacaggac | acttccttgc | aggaacagag gtgccatgca | 1080 |
| gccccgggta | ctccttgttg | ttgccctcct | ggcgctcctg | gcctctgccc gtaagcactt | 1140 |
| ggtgggactg | ggctgggggc | agggtggagg | caacttgggg | atcccagtcc caatgggtgg | 1200 |
| tcaagcagga | gcccagggct | cgtccatagg | ccgatccacc | ccactcagcc ctgctctttc | 1260 |
| ctcaggagct | tcagaggccg | aggatgcctc | ccttctcagc | ttcatgcagg gctacatgaa | 1320 |
| gcacgccacc | aagaccgcca | aggatgcact | gagcagcgtg | caggagtccc aggtggccca | 1380 |
| gcaggccagg | tacacccgct | ggcctccctc | cccatccccc | ctgccagctg cctccattcc | 1440 |
| cacccacccc | tgccctggtg | agatcccaac | aatggaatgg | aggtgctcca gcctcccctg | 1500 |
| ggcctgtgcc | tcttcagcct | cctctttcct | cacagggcct | tgtcaggct gctgcgggag | 1560 |
| agatgacaga | gttgagactg | cattcctccc | aggtccctcc | tttctcccca gagcagtcct | 1620 |
| agggcgcgcc | gttttagccc | tcatttccat | tttcctttcc | tttccctttc tttcccttc | 1680 |
| tatttctttc | tttctttctt | tctttctttc | tttctttctt | tctttctttc tttctttctt | 1740 |
| tctttctttc | ctttctttct | ttcttttctt | ctttctttct | ttcctttctt tctcttctt | 1800 |
| tctttctttc | tttcctttttt | ctttctttcc | ctctcttcct | ttctctcttt ctttcttctt | 1860 |
| cttttttttt | taatggagtc | tccctctgtc | acccaggctg | gagtgcagtg gtgccatctc | 1920 |
| ggctcactgc | aacctccgtc | tcccgggttc | aacccattct | cctgcctcag cctcccaagt | 1980 |
| agctgggatt | acaggcacgc | gccaccacac | ccagctaatt | tttgtatttt tagcagagat | 2040 |
| ggggtttcac | catgttggcc | aggttggtct | tgaattcctg | acctcagggg atcctcctgc | 2100 |
| ctcggcctcc | caaagcgctg | ggattacagg | catgagccac | tgcgcctggc cccattttcc | 2160 |
| ttttctgaag | gtctggctag | agcagtggtc | tcagccttt | ttggcaccag ggaccagttt | 2220 |
| tgtggtggac | aatttttcca | tgggccagcg | gggatggttt | tgggatgaag ctgttccacc | 2280 |
| tcagatcatc | aggcattaga | ttctcataag | gagccctcca | cctagatccc tggcatgtgc | 2340 |
| agttcacaac | agggttcaca | ctcctatgag | aatgtaaggc | cacttgatct gacaggaggc | 2400 |
| ggagctcagg | cggtattgct | cactcaccca | ccactcactt | cgtgctgtgc agcccggctc | 2460 |
| ctaacagtcc | atggaccagt | acctatctat | gacttggggg | ttggggaccc ctgggctagg | 2520 |
| ggtttgcctt | gggaggcccc | acctgaccta | attcaagccc | gtgagtgctt ctgctttgtt | 2580 |
| ctaagacctg | gggccagtgt | gagcagaagt | gtgtccttcc | tctcccatcc tgcccctgcc | 2640 |
| catcagtact | ctcctctccc | ctactcccctt | tccacctca | ccctgactgg cattagctgg | 2700 |
| catagcagag | gtgttcataa | acattcttag | tccccagaac | cggctttggg gtaggtgtta | 2760 |
| ttttctcact | ttgcagatga | gaaaattgag | gctcagagcg | attaggtgac ctgccccaga | 2820 |
| tcacacaact | aatcaatcct | ccaatgactt | tccaaatgag | aggctgcctc cctctgtcct | 2880 |
| accctgctca | gagccaccag | gttgtgcaac | tccaggcggt | gctgtttgca cagaaaacaa | 2940 |
| tgacagcctt | gacctttcac | atctccccac | cctgtcactt | tgtgcctcag gcccaggggc | 3000 |
| ataaacatct | gaggtgacct | ggagatggca | gggtttgact | tgtgctgggg ttcctgcaag | 3060 |
| gatatctctt | ctcccagggt | ggcagctgtg | ggggattcct | gcctgaggtc tcagggctgt | 3120 |
| cgtccagtga | agttgagagg | gtggtgtggt | cctgactggt | gtcgtccagt ggggacatgg | 3180 |
| gtgtgggtcc | catggttgcc | tacagaggag | ttctcatgcc | ctgctctgtt gcttccctg | 3240 |
| actgatttag | gggctgggtg | accgatggct | tcagttccct | gaaagactac tggagcaccg | 3300 |
| ttaaggacaa | gttctctgag | ttctgggatt | tggaccctga | ggtcagacca acttcagccg | 3360 |

-continued

```
tggctgcctg agacctcaat accccaagtc cacctgccta tccatcctgc cagctccttg    3420
ggtcctgcaa tctccagggc tgcccctgta ggttgcttaa aagggacagt attctcagtg    3480
ctctcctacc ccacctcatg cctggccccc ctccaggcat gctggcctcc caataaagct    3540
ggacaagaag ctgctatgag tgggccgtcg caagtgtgcc atctgtgtct gggcatggga    3600
aagggccgag gctgttctgt gggtgggcac tggacagact ccaggtcagg caggcatgga    3660
ggccagcgct ctatccacct tctggtagct gggcagtctc tgggcctcag tttcttcatc    3720
tctaaggtag gaatcaccct ccgtaccctg ccttccttga cagctttgtg cggaaggtca    3780
aacaggacaa taagtttgct gatactttga taaactgtta ggtgctgcac aacatgactt    3840
gagtgtgtgc cccatgccag ccactatgcc tggcacttaa gttgtcatca gagttgagac    3900
tgtgtgtgtt tactcaaaac tgtggagctg acctccccta tccaggccac ctagccct     3958
```

<210> SEQ ID NO 5
<211> LENGTH: 22
<212> TYPE: DNA
<213> ORGANISM: Artificial Sequence
<220> FEATURE:
<223> OTHER INFORMATION: PCR Primer

<400> SEQUENCE: 5
tcagcttcat gcagggttac at    22

<210> SEQ ID NO 6
<211> LENGTH: 19
<212> TYPE: DNA
<213> ORGANISM: Artificial Sequence
<220> FEATURE:
<223> OTHER INFORMATION: PCR Primer

<400> SEQUENCE: 6
acgctgctca gtgcatcct    19

<210> SEQ ID NO 7
<211> LENGTH: 21
<212> TYPE: DNA
<213> ORGANISM: Artificial Sequence
<220> FEATURE:
<223> OTHER INFORMATION: PCR Probe

<400> SEQUENCE: 7
aagcacgcca ccaagaccgc c    21

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc    19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9

```
gaagatggtg atgggatttc                                               20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                               20

<210> SEQ ID NO 11
<211> LENGTH: 518
<212> TYPE: DNA
<213> ORGANISM: M. musculus
<220> FEATURE:

<400> SEQUENCE: 11
cctgctcagt tttatcccta gaagcagcta gctactccag gtacgtaggt gccatgcagc    60
cccggacgct cctcactgtg gccctcttgg ctctcctggc atctgcccga gctgaagagg   120
tagagggatc cttgctgctg ggctctgtgc agggctacat ggaacaagcc tccaagacgg   180
tccaggatgc gctaagtagc gtgcaggagt ccgatatagc tgcggtggcc aggggctgga   240
tggacaatca cttcagattc ctgaaaggct actggagcaa gtttactgac aagttcaccg   300
gcttctggga ttctaaccct gaggaccaac caactccagc tattgagtcg tgagacttct   360
gtgttgcaga tgtgcctgtt cctccatcct gctgccccccc tccaggcctg ccaggtggcc   420
cctgaaggtt gctttaaggg gaaagtatgt tctcatgtct tcacccctcc ctagatctca   480
cctaaacatg ctgtccctaa taaagctgga taagaagc                           518

<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12
tgcagggcta catggaacaa                                               20

<210> SEQ ID NO 13
<211> LENGTH: 20
<212> TYPE: DNA
<213> ORGANISM: Artificial Sequence
<220> FEATURE:
<223> OTHER INFORMATION: PCR Primer

<400> SEQUENCE: 13
cggactcctg cacgctactt                                               20

<210> SEQ ID NO 14
<211> LENGTH: 23
<212> TYPE: DNA
<213> ORGANISM: Artificial Sequence
<220> FEATURE:
<223> OTHER INFORMATION: PCR Probe

<400> SEQUENCE: 14
ctccaagacg gtccaggatg cgc                                           23

<210> SEQ ID NO 15
```

```
<211> LENGTH: 20
<212> TYPE: DNA
<213> ORGANISM: Artificial Sequence
<220> FEATURE:
<223> OTHER INFORMATION: PCR Primer

<400> SEQUENCE: 15
ggcaaattca acggcacagt                                               20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gggtctcgct cctggaagat                                               20

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17
aaggccgaga atgggaagct tgtcatc                                       27

<210> SEQ ID NO 18
<211> LENGTH: 533
<212> TYPE: DNA
<213> ORGANISM: H. sapiens
<220> FEATURE:
<221> NAME/KEY: CDS
<222> LOCATION: (47)...(346)

<400> SEQUENCE: 18
tgctcagttc atccctagag gcagctgctc caggaacaga ggtgcc atg cag ccc       55
                                                 Met Gln Pro
                                                   1 cgg gta ctc ctt gtt gtt gcc ctc ctg gcg ctc ctg gcc tct gcc cga    103
Arg Val Leu Leu Val Val Ala Leu Leu Ala Leu Leu Ala Ser Ala Arg
  5                  10                  15 gct tca gag gcc gag gat gcc tcc ctt ctc agc ttc atg cag ggt tac    151
Ala Ser Glu Ala Glu Asp Ala Ser Leu Leu Ser Phe Met Gln Gly Tyr
         20                  25                  30          35 atg aag cac gcc acc aag acc gcc aag gat gca ctg agc agc gtg cag    199
Met Lys His Ala Thr Lys Thr Ala Lys Asp Ala Leu Ser Ser Val Gln
                 40                  45                  50 gag tcc cag gtg gcc cag cag gcc agg ggc tgg gtg acc gat ggc ttc    247
Glu Ser Gln Val Ala Gln Gln Ala Arg Gly Trp Val Thr Asp Gly Phe
             55                  60                  65 agt tcc ctg aaa gac tac tgg agc acc gtt aag gac aag ttc tct gag    295
Ser Ser Leu Lys Asp Tyr Trp Ser Thr Val Lys Asp Lys Phe Ser Glu
         70                  75                  80 ttc tgg gat ttg gac cct gag gtc aga cca act tca gcc gtg gct gcc    343
Phe Trp Asp Leu Asp Pro Glu Val Arg Pro Thr Ser Ala Val Ala Ala
     85                  90                  95 tga gacctcaata ccccaagtcc acctgcctat ccatcctgcg agctccttgg         396
gtcctgcaat ctccagggct gcccctgtag gttgcttaaa agggacagta ttctcagtgc  456
tctcctaccc cacctcatgc ctggcccccc tccaggcatg ctggcctccc aataaagctg  516
```

```
gacaagaagc tgctatg                                              533
```

\<210\> SEQ ID NO 19
\<211\> LENGTH: 20
\<212\> TYPE: DNA
\<213\> ORGANISM: Artificial Sequence
\<220\> FEATURE:
\<223\> OTHER INFORMATION: Synthetic Oligonucleotide

\<400\> SEQUENCE: 19

```
ctggagcagc tgcctctagg                                            20
```

\<210\> SEQ ID NO 20
\<211\> LENGTH: 20
\<212\> TYPE: DNA
\<213\> ORGANISM: Artificial Sequence
\<220\> FEATURE:
\<223\> OTHER INFORMATION: Synthetic Oligonucleotide

\<400\> SEQUENCE: 20

```
ccctgcatga agctgagaag                                            20
```

\<210\> SEQ ID NO 21
\<211\> LENGTH: 20
\<212\> TYPE: DNA
\<213\> ORGANISM: Artificial Sequence
\<220\> FEATURE:
\<223\> OTHER INFORMATION: Synthetic Oligonucleotide

\<400\> SEQUENCE: 21

```
gtgcttcatg taaccctgca                                            20
```

\<210\> SEQ ID NO 22
\<211\> LENGTH: 20
\<212\> TYPE: DNA
\<213\> ORGANISM: Artificial Sequence
\<220\> FEATURE:
\<223\> OTHER INFORMATION: Synthetic Oligonucleotide

\<400\> SEQUENCE: 22

```
tggcctgctg ggccacctgg                                            20
```

\<210\> SEQ ID NO 23
\<211\> LENGTH: 20
\<212\> TYPE: DNA
\<213\> ORGANISM: Artificial Sequence
\<220\> FEATURE:
\<223\> OTHER INFORMATION: Synthetic Oligonucleotide

\<400\> SEQUENCE: 23

```
tgctccagta gtctttcagg                                            20
```

\<210\> SEQ ID NO 24
\<211\> LENGTH: 20
\<212\> TYPE: DNA
\<213\> ORGANISM: Artificial Sequence
\<220\> FEATURE:
\<223\> OTHER INFORMATION: Synthetic Oligonucleotide

\<400\> SEQUENCE: 24

```
tgacctcagg gtccaaatcc                                            20
```

\<210\> SEQ ID NO 25
\<211\> LENGTH: 20
\<212\> TYPE: DNA
\<213\> ORGANISM: Artificial Sequence

```
<220> FEATURE:
<223> OTHER INFORMATION: Synthetic Oligonucleotide

<400> SEQUENCE: 25
ctctagggat gaactgagca                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
cagctgcctc tagggatgaa                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
ttcctggagc agctgcctct                                                    20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
acctctgttc ctggagcagc                                                    20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
atggcacctc tgttcctgga                                                    20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
gggctgcatg gcacctctgt                                                    20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
ggcaacaaca aggagtaccc                                                    20
```

```
<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
ggagggcaac aacaaggagt                                                 20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
agctcgggca gaggccagga                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
tctgaagctc gggcagaggc                                                 20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
cggcctctga agctcgggca                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
catcctcggc ctctgaagct                                                 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
gggaggcatc ctcggcctct                                                 20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 38
gagaagggag gcatcctcgg                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
gctgagaagg gaggcatcct                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
tgcatgaagc tgagaaggga                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
gcgtgcttca tgtaaccctg                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
ttggtggcgt gcttcatgta                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
gcatccttgg cggtcttggt                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 44
ctcagtgcat ccttggcggt                                              20

<210> SEQ ID NO 45
```

<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 45
tgctcagtgc atccttggcg                                                    20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
ctcctgcacg ctgctcagtg                                                    20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
gactcctgca cgctgctcag                                                    20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
gccacctggg actcctgcac                                                    20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
gcccctggcc tgctgggcca                                                    20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
agcccctggc ctgctgggcc                                                    20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
gaagccatcg gtcacccagc                                            20

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
ctgaagccat cggtcaccca                                            20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
tttcagggaa ctgaagccat                                            20

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 54
cagtagtctt tcagggaact                                            20

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
aacggtgctc cagtagtctt                                            20

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
ccttaacggt gctccagtag                                            20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 57
gaacttgtcc ttaacggtgc                                            20

<210> SEQ ID NO 58
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 58
ctcagagaac ttgtccttaa                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
agaactcaga gaacttgtcc                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
atcccagaac tcagagaact                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
cagggtccaa atcccagaac                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 62
ttggtctgac ctcagggtcc                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 63
gttggtctga cctcagggtc                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 64
gctgaagttg gtctgacctc                                              20
```

<210> SEQ ID NO 65
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 65
cagccacggc tgaagttggt                                                  20

<210> SEQ ID NO 66
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 66
caggcagcca cggctgaagt                                                  20

<210> SEQ ID NO 67
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 67
attgaggtct caggcagcca                                                  20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 68
tggataggca ggtggacttg                                                  20

<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
ctcgcaggat ggataggcag                                                  20

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 70
aggagctcgc aggatggata                                                  20

<210> SEQ ID NO 71
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 71
gacccaagga gctcgcagga                      20

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72
tgcaggaccc aaggagctcg                      20

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
tggagattgc aggacccaag                      20

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 74
agccctggag attgcaggac                      20

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 75
ggcagccctg gagattgcag                      20

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
ccttttaagc aacctacagg                      20

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 77
ctgtcccttt taagcaacct                      20

```
<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
agaatactgt cccttttaag                                               20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
cactgagaat actgtccctt                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
taggagagca ctgagaatac                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
gggtaggaga gcactgagaa                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
aggccagcat gcctggaggg                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
ttgggaggcc agcatgcctg                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 84
agctttattg ggaggccagc                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 85
tgtccagctt tattgggagg                                               20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
cttgtccagc tttattggga                                               20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
agcttcttgt ccagctttat                                               20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
catagcagct tcttgtccag                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 89
acctggagca gctgcctcta                                               20

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 90
agggcattac ctggagcagc                                               20

<210> SEQ ID NO 91
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 91
acctctgttc ctgcaaggaa                                                 20

<210> SEQ ID NO 92
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 92
aagtgcttac gggcagaggc                                                 20

<210> SEQ ID NO 93
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 93
gcgggtgtac ctggcctgct                                                 20

<210> SEQ ID NO 94
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 94
aaccctgttg tgaactgcac                                                 20

<210> SEQ ID NO 95
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 95
agtgagcaat accgcctgag                                                 20

<210> SEQ ID NO 96
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 96
cgggcttgaa ttaggtcagg                                                 20

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
```
tagggataaa actgagcagg                                                20

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 98
ctggagtagc tagctgcttc                                                20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
gctgcatggc acctacgtac                                                20

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 100
ccacagtgag gagcgtccgg                                                20

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 101
ggcagatgcc aggagagcca                                                20

<210> SEQ ID NO 102
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 102
ctacctcttc agctcgggca                                                20

<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 103
cagcagcaag gatccctcta                                                20

<210> SEQ ID NO 104
<211> LENGTH: 20
<212> TYPE: DNA
<213> ORGANISM: Artificial Sequence -continued

```
<220> FEATURE:
<223> OTHER INFORMATION: Synthetic Oligonucleotide

<400> SEQUENCE: 104
gcacagagcc cagcagcaag                                                   20

<210> SEQ ID NO 105
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 105
ccctggccac cgcagctata                                                   20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 106
atctgaagtg attgtccatc                                                   20

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 107
agtagccttt caggaatctg                                                   20

<210> SEQ ID NO 108
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 108
cttgtcagta aacttgctcc                                                   20

<210> SEQ ID NO 109
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 109
gaagccggtg aacttgtcag                                                   20

<210> SEQ ID NO 110
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 110
gaatcccaga agccggtgaa                                                   20
```

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 111
ggttagaatc ccagaagccg                                                    20

<210> SEQ ID NO 112
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 112
tggagttggt tggtcctcag                                                    20

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 113
tcacgactca atagctggag                                                    20

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
cccttaaagc aaccttcagg                                                    20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 115
agacatgaga acatactttc                                                    20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 116
catgtttagg tgagatctag                                                    20

<210> SEQ ID NO 117
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 117
tcttatccag ctttattagg                                               20

<210> SEQ ID NO 118
<211> LENGTH: 20
<212> TYPE: DNA
<213> ORGANISM: H. sapiens
<220> FEATURE:

<400> SEQUENCE: 118
ccuagaggca gcugcuccag                                               20

<210> SEQ ID NO 119
<211> LENGTH: 20
<212> TYPE: DNA
<213> ORGANISM: H. sapiens
<220> FEATURE:

<400> SEQUENCE: 119
cuucucagcu ucaugcaggg                                               20

<210> SEQ ID NO 120
<211> LENGTH: 20
<212> TYPE: DNA
<213> ORGANISM: H. sapiens
<220> FEATURE:

<400> SEQUENCE: 120
ugcaggguua caugaagcac                                               20

<210> SEQ ID NO 121
<211> LENGTH: 20
<212> TYPE: DNA
<213> ORGANISM: H. sapiens
<220> FEATURE:

<400> SEQUENCE: 121
ccagguggcc cagcaggcca                                               20

<210> SEQ ID NO 122
<211> LENGTH: 20
<212> TYPE: DNA
<213> ORGANISM: H. sapiens
<220> FEATURE:

<400> SEQUENCE: 122
ccugaaagac uacuggagca                                               20

<210> SEQ ID NO 123
<211> LENGTH: 20
<212> TYPE: DNA
<213> ORGANISM: H. sapiens
<220> FEATURE:

<400> SEQUENCE: 123
ugcucaguuc aucccuagag                                               20

<210> SEQ ID NO 124
<211> LENGTH: 20
<212> TYPE: DNA
<213> ORGANISM: H. sapiens
<220> FEATURE:

<400> SEQUENCE: 124
```
agaggcagcu gcuccaggaa                                                    20

<210> SEQ ID NO 125
<211> LENGTH: 20
<212> TYPE: DNA
<213> ORGANISM: H. sapiens
<220> FEATURE:

<400> SEQUENCE: 125
gcugcuccag gaacagaggu                                                    20

<210> SEQ ID NO 126
<211> LENGTH: 20
<212> TYPE: DNA
<213> ORGANISM: H. sapiens
<220> FEATURE:

<400> SEQUENCE: 126
uccaggaaca gaggugccau                                                    20

<210> SEQ ID NO 127
<211> LENGTH: 20
<212> TYPE: DNA
<213> ORGANISM: H. sapiens
<220> FEATURE:

<400> SEQUENCE: 127
acagaggugc caugcagccc                                                    20

<210> SEQ ID NO 128
<211> LENGTH: 20
<212> TYPE: DNA
<213> ORGANISM: H. sapiens
<220> FEATURE:

<400> SEQUENCE: 128
ggguacuccu uguuguugcc                                                    20

<210> SEQ ID NO 129
<211> LENGTH: 20
<212> TYPE: DNA
<213> ORGANISM: H. sapiens
<220> FEATURE:

<400> SEQUENCE: 129
acuccuuguu guugcccucc                                                    20

<210> SEQ ID NO 130
<211> LENGTH: 20
<212> TYPE: DNA
<213> ORGANISM: H. sapiens
<220> FEATURE:

<400> SEQUENCE: 130
uccuggccuc ugcccgagcu                                                    20

<210> SEQ ID NO 131
<211> LENGTH: 20
<212> TYPE: DNA
<213> ORGANISM: H. sapiens
<220> FEATURE:

<400> SEQUENCE: 131
gccucugccc gagcuucaga                                                    20

<210> SEQ ID NO 132
<211> LENGTH: 20
<212> TYPE: DNA
<213> ORGANISM: H. sapiens
<220> FEATURE:

<400> SEQUENCE: 132
agcuucagag gccgaggaug                                               20

<210> SEQ ID NO 133
<211> LENGTH: 20
<212> TYPE: DNA
<213> ORGANISM: H. sapiens
<220> FEATURE:

<400> SEQUENCE: 133
agaggccgag gaugccuccc                                               20

<210> SEQ ID NO 134
<211> LENGTH: 20
<212> TYPE: DNA
<213> ORGANISM: H. sapiens
<220> FEATURE:

<400> SEQUENCE: 134
ccgaggaugc cucccuucuc                                               20

<210> SEQ ID NO 135
<211> LENGTH: 20
<212> TYPE: DNA
<213> ORGANISM: H. sapiens
<220> FEATURE:

<400> SEQUENCE: 135
aggaugccuc ccuucucagc                                               20

<210> SEQ ID NO 136
<211> LENGTH: 20
<212> TYPE: DNA
<213> ORGANISM: H. sapiens
<220> FEATURE:

<400> SEQUENCE: 136
ucccuucuca gcuucaugca                                               20

<210> SEQ ID NO 137
<211> LENGTH: 20
<212> TYPE: DNA
<213> ORGANISM: H. sapiens
<220> FEATURE:

<400> SEQUENCE: 137
caggguuaca ugaagcacgc                                               20

<210> SEQ ID NO 138
<211> LENGTH: 20
<212> TYPE: DNA
<213> ORGANISM: H. sapiens
<220> FEATURE:

<400> SEQUENCE: 138
uacaugaagc acgccaccaa                                               20

```
<210> SEQ ID NO 139
<211> LENGTH: 20
<212> TYPE: DNA
<213> ORGANISM: H. sapiens
<220> FEATURE:

<400> SEQUENCE: 139
accaagaccg ccaaggaugc                                               20

<210> SEQ ID NO 140
<211> LENGTH: 20
<212> TYPE: DNA
<213> ORGANISM: H. sapiens
<220> FEATURE:

<400> SEQUENCE: 140
accgccaagg augcacugag                                               20

<210> SEQ ID NO 141
<211> LENGTH: 20
<212> TYPE: DNA
<213> ORGANISM: H. sapiens
<220> FEATURE:

<400> SEQUENCE: 141
cgccaaggau gcacugagca                                               20

<210> SEQ ID NO 142
<211> LENGTH: 20
<212> TYPE: DNA
<213> ORGANISM: H. sapiens
<220> FEATURE:

<400> SEQUENCE: 142
cacugagcag cgugcaggag                                               20

<210> SEQ ID NO 143
<211> LENGTH: 20
<212> TYPE: DNA
<213> ORGANISM: H. sapiens
<220> FEATURE:

<400> SEQUENCE: 143
cugagcagcg ugcaggaguc                                               20

<210> SEQ ID NO 144
<211> LENGTH: 20
<212> TYPE: DNA
<213> ORGANISM: H. sapiens
<220> FEATURE:

<400> SEQUENCE: 144
gugcaggagu cccagguggc                                               20

<210> SEQ ID NO 145
<211> LENGTH: 20
<212> TYPE: DNA
<213> ORGANISM: H. sapiens
<220> FEATURE:

<400> SEQUENCE: 145
uggcccagca ggccaggggc                                               20

<210> SEQ ID NO 146
<211> LENGTH: 20
```

```
<212> TYPE: DNA
<213> ORGANISM: H. sapiens
<220> FEATURE:

<400> SEQUENCE: 146
ggcccagcag gccaggggcu                                               20

<210> SEQ ID NO 147
<211> LENGTH: 20
<212> TYPE: DNA
<213> ORGANISM: H. sapiens
<220> FEATURE:

<400> SEQUENCE: 147
gcugggugac cgauggcuuc                                               20

<210> SEQ ID NO 148
<211> LENGTH: 20
<212> TYPE: DNA
<213> ORGANISM: H. sapiens
<220> FEATURE:

<400> SEQUENCE: 148
ugggugaccg auggcuucag                                               20

<210> SEQ ID NO 149
<211> LENGTH: 20
<212> TYPE: DNA
<213> ORGANISM: H. sapiens
<220> FEATURE:

<400> SEQUENCE: 149
auggcuucag uucccugaaa                                               20

<210> SEQ ID NO 150
<211> LENGTH: 20
<212> TYPE: DNA
<213> ORGANISM: H. sapiens
<220> FEATURE:

<400> SEQUENCE: 150
aagacuacug gagcaccguu                                               20

<210> SEQ ID NO 151
<211> LENGTH: 20
<212> TYPE: DNA
<213> ORGANISM: H. sapiens
<220> FEATURE:

<400> SEQUENCE: 151
cuacuggagc accguuaagg                                               20

<210> SEQ ID NO 152
<211> LENGTH: 20
<212> TYPE: DNA
<213> ORGANISM: H. sapiens
<220> FEATURE:

<400> SEQUENCE: 152
gcaccguuaa ggacaaguuc                                               20

<210> SEQ ID NO 153
<211> LENGTH: 20
<212> TYPE: DNA
<213> ORGANISM: H. sapiens
```

<220> FEATURE:

<400> SEQUENCE: 153
uuaaggacaa guucucugag                                               20

<210> SEQ ID NO 154
<211> LENGTH: 20
<212> TYPE: DNA
<213> ORGANISM: H. sapiens
<220> FEATURE:

<400> SEQUENCE: 154
ggacaaguuc ucugaguucu                                               20

<210> SEQ ID NO 155
<211> LENGTH: 20
<212> TYPE: DNA
<213> ORGANISM: H. sapiens
<220> FEATURE:

<400> SEQUENCE: 155
guucugggau uuggacccug                                               20

<210> SEQ ID NO 156
<211> LENGTH: 20
<212> TYPE: DNA
<213> ORGANISM: H. sapiens
<220> FEATURE:

<400> SEQUENCE: 156
ggacccugag gucagaccaa                                               20

<210> SEQ ID NO 157
<211> LENGTH: 20
<212> TYPE: DNA
<213> ORGANISM: H. sapiens
<220> FEATURE:

<400> SEQUENCE: 157
gacccugagg ucagaccaac                                               20

<210> SEQ ID NO 158
<211> LENGTH: 20
<212> TYPE: DNA
<213> ORGANISM: H. sapiens
<220> FEATURE:

<400> SEQUENCE: 158
gaggucagac caacuucagc                                               20

<210> SEQ ID NO 159
<211> LENGTH: 20
<212> TYPE: DNA
<213> ORGANISM: H. sapiens
<220> FEATURE:

<400> SEQUENCE: 159
accaacuuca gccguggcug                                               20

<210> SEQ ID NO 160
<211> LENGTH: 20
<212> TYPE: DNA
<213> ORGANISM: H. sapiens
<220> FEATURE:

-continued

```
<400> SEQUENCE: 160
acuucagccg uggcugccug                                                    20

<210> SEQ ID NO 161
<211> LENGTH: 20
<212> TYPE: DNA
<213> ORGANISM: H. sapiens
<220> FEATURE:

<400> SEQUENCE: 161
uggcugccug agaccucaau                                                    20

<210> SEQ ID NO 162
<211> LENGTH: 20
<212> TYPE: DNA
<213> ORGANISM: H. sapiens
<220> FEATURE:

<400> SEQUENCE: 162
caaguccacc ugccuaucca                                                    20

<210> SEQ ID NO 163
<211> LENGTH: 20
<212> TYPE: DNA
<213> ORGANISM: H. sapiens
<220> FEATURE:

<400> SEQUENCE: 163
cugccuaucc auccugcgag                                                    20

<210> SEQ ID NO 164
<211> LENGTH: 20
<212> TYPE: DNA
<213> ORGANISM: H. sapiens
<220> FEATURE:

<400> SEQUENCE: 164
uauccauccu gcgagcuccu                                                    20

<210> SEQ ID NO 165
<211> LENGTH: 20
<212> TYPE: DNA
<213> ORGANISM: H. sapiens
<220> FEATURE:

<400> SEQUENCE: 165
uccugcgagc uccuuggguc                                                    20

<210> SEQ ID NO 166
<211> LENGTH: 20
<212> TYPE: DNA
<213> ORGANISM: H. sapiens
<220> FEATURE:

<400> SEQUENCE: 166
cgagcuccuu ggguccugca                                                    20

<210> SEQ ID NO 167
<211> LENGTH: 20
<212> TYPE: DNA
<213> ORGANISM: H. sapiens
<220> FEATURE:

<400> SEQUENCE: 167
```
cuugggaccu gcaaucucca                                         20

<210> SEQ ID NO 168
<211> LENGTH: 20
<212> TYPE: DNA
<213> ORGANISM: H. sapiens
<220> FEATURE:

<400> SEQUENCE: 168
guccugcaau cuccagggcu                                         20

<210> SEQ ID NO 169
<211> LENGTH: 20
<212> TYPE: DNA
<213> ORGANISM: H. sapiens
<220> FEATURE:

<400> SEQUENCE: 169
cugcaaucuc cagggcugcc                                         20

<210> SEQ ID NO 170
<211> LENGTH: 20
<212> TYPE: DNA
<213> ORGANISM: H. sapiens
<220> FEATURE:

<400> SEQUENCE: 170
ccuguagguu gcuuaaaagg                                         20

<210> SEQ ID NO 171
<211> LENGTH: 20
<212> TYPE: DNA
<213> ORGANISM: H. sapiens
<220> FEATURE:

<400> SEQUENCE: 171
agguugcuua aaagggacag                                         20

<210> SEQ ID NO 172
<211> LENGTH: 20
<212> TYPE: DNA
<213> ORGANISM: H. sapiens
<220> FEATURE:

<400> SEQUENCE: 172
cuuaaaaggg acaguauucu                                         20

<210> SEQ ID NO 173
<211> LENGTH: 20
<212> TYPE: DNA
<213> ORGANISM: H. sapiens
<220> FEATURE:

<400> SEQUENCE: 173
aagggacagu auucucagug                                         20

<210> SEQ ID NO 174
<211> LENGTH: 20
<212> TYPE: DNA
<213> ORGANISM: H. sapiens
<220> FEATURE:

<400> SEQUENCE: 174
guauucucag ugcucuccua                                         20

```
<210> SEQ ID NO 175
<211> LENGTH: 20
<212> TYPE: DNA
<213> ORGANISM: H. sapiens
<220> FEATURE:

<400> SEQUENCE: 175
uucucagugc ucuccuaccc                                               20

<210> SEQ ID NO 176
<211> LENGTH: 20
<212> TYPE: DNA
<213> ORGANISM: H. sapiens
<220> FEATURE:

<400> SEQUENCE: 176
cccuccaggc augcuggccu                                               20

<210> SEQ ID NO 177
<211> LENGTH: 20
<212> TYPE: DNA
<213> ORGANISM: H. sapiens
<220> FEATURE:

<400> SEQUENCE: 177
caggcaugcu ggccucccaa                                               20

<210> SEQ ID NO 178
<211> LENGTH: 20
<212> TYPE: DNA
<213> ORGANISM: H. sapiens
<220> FEATURE:

<400> SEQUENCE: 178
gcuggccucc caauaaagcu                                               20

<210> SEQ ID NO 179
<211> LENGTH: 20
<212> TYPE: DNA
<213> ORGANISM: H. sapiens
<220> FEATURE:

<400> SEQUENCE: 179
ccucccaaua aagcuggaca                                               20

<210> SEQ ID NO 180
<211> LENGTH: 20
<212> TYPE: DNA
<213> ORGANISM: H. sapiens
<220> FEATURE:

<400> SEQUENCE: 180
ucccaauaaa gcuggacaag                                               20

<210> SEQ ID NO 181
<211> LENGTH: 20
<212> TYPE: DNA
<213> ORGANISM: H. sapiens
<220> FEATURE:

<400> SEQUENCE: 181
auaaagcugg acaagaagcu                                               20

<210> SEQ ID NO 182
```

-continued

```
<211> LENGTH: 20
<212> TYPE: DNA
<213> ORGANISM: H. sapiens
<220> FEATURE:

<400> SEQUENCE: 182
cuggacaaga agcugcuaug                                               20

<210> SEQ ID NO 183
<211> LENGTH: 20
<212> TYPE: DNA
<213> ORGANISM: H. sapiens
<220> FEATURE:

<400> SEQUENCE: 183
uagaggcagc ugcuccaggu                                               20

<210> SEQ ID NO 184
<211> LENGTH: 20
<212> TYPE: DNA
<213> ORGANISM: H. sapiens
<220> FEATURE:

<400> SEQUENCE: 184
gcugcuccag guaaugcccu                                               20

<210> SEQ ID NO 185
<211> LENGTH: 20
<212> TYPE: DNA
<213> ORGANISM: H. sapiens
<220> FEATURE:

<400> SEQUENCE: 185
uuccuugcag gaacagaggu                                               20

<210> SEQ ID NO 186
<211> LENGTH: 20
<212> TYPE: DNA
<213> ORGANISM: H. sapiens
<220> FEATURE:

<400> SEQUENCE: 186
gccucugccc guaagcacuu                                               20

<210> SEQ ID NO 187
<211> LENGTH: 20
<212> TYPE: DNA
<213> ORGANISM: H. sapiens
<220> FEATURE:

<400> SEQUENCE: 187
agcaggccag guacacccgc                                               20

<210> SEQ ID NO 188
<211> LENGTH: 20
<212> TYPE: DNA
<213> ORGANISM: H. sapiens
<220> FEATURE:

<400> SEQUENCE: 188
gugcaguuca caacagggua                                               20

<210> SEQ ID NO 189
<211> LENGTH: 20
<212> TYPE: DNA
```

-continued

```
<213> ORGANISM: H. sapiens
<220> FEATURE:

<400> SEQUENCE: 189
cucaggcggu auugcucacu                                                20

<210> SEQ ID NO 190
<211> LENGTH: 20
<212> TYPE: DNA
<213> ORGANISM: H. sapiens
<220> FEATURE:

<400> SEQUENCE: 190
ccugaccuaa uucaagcccg                                                20

<210> SEQ ID NO 191
<211> LENGTH: 20
<212> TYPE: DNA
<213> ORGANISM: M. musculus
<220> FEATURE:

<400> SEQUENCE: 191
ccugcucagu uuuaucccua                                                20

<210> SEQ ID NO 192
<211> LENGTH: 20
<212> TYPE: DNA
<213> ORGANISM: M. musculus
<220> FEATURE:

<400> SEQUENCE: 192
guacguaggu gccaugcagc                                                20

<210> SEQ ID NO 193
<211> LENGTH: 20
<212> TYPE: DNA
<213> ORGANISM: M. musculus
<220> FEATURE:

<400> SEQUENCE: 193
ccggacgcuc cucacugugg                                                20

<210> SEQ ID NO 194
<211> LENGTH: 20
<212> TYPE: DNA
<213> ORGANISM: M. musculus
<220> FEATURE:

<400> SEQUENCE: 194
uggcucuccu ggcaucugcc                                                20

<210> SEQ ID NO 195
<211> LENGTH: 20
<212> TYPE: DNA
<213> ORGANISM: M. musculus
<220> FEATURE:

<400> SEQUENCE: 195
ugcccgagcu gaagagguag                                                20

<210> SEQ ID NO 196
<211> LENGTH: 20
<212> TYPE: DNA
<213> ORGANISM: M. musculus
<220> FEATURE:
```

```
<400> SEQUENCE: 196
uagagggauc cuugcugcug                                              20

<210> SEQ ID NO 197
<211> LENGTH: 20
<212> TYPE: DNA
<213> ORGANISM: M. musculus
<220> FEATURE:

<400> SEQUENCE: 197
cuugcugcug ggcucugugc                                              20

<210> SEQ ID NO 198
<211> LENGTH: 20
<212> TYPE: DNA
<213> ORGANISM: M. musculus
<220> FEATURE:

<400> SEQUENCE: 198
uauagcugcg guggccaggg                                              20

<210> SEQ ID NO 199
<211> LENGTH: 20
<212> TYPE: DNA
<213> ORGANISM: M. musculus
<220> FEATURE:

<400> SEQUENCE: 199
cagauuccug aaaggcuacu                                              20

<210> SEQ ID NO 200
<211> LENGTH: 20
<212> TYPE: DNA
<213> ORGANISM: M. musculus
<220> FEATURE:

<400> SEQUENCE: 200
ggagcaaguu uacugacaag                                              20

<210> SEQ ID NO 201
<211> LENGTH: 20
<212> TYPE: DNA
<213> ORGANISM: M. musculus
<220> FEATURE:

<400> SEQUENCE: 201
cugacaaguu caccggcuuc                                              20

<210> SEQ ID NO 202
<211> LENGTH: 20
<212> TYPE: DNA
<213> ORGANISM: M. musculus
<220> FEATURE:

<400> SEQUENCE: 202
cggcuucugg gauucuaacc                                              20

<210> SEQ ID NO 203
<211> LENGTH: 20
<212> TYPE: DNA
<213> ORGANISM: M. musculus
<220> FEATURE:

<400> SEQUENCE: 203
```
cugaggacca accaacucca                                             20

<210> SEQ ID NO 204
<211> LENGTH: 20
<212> TYPE: DNA
<213> ORGANISM: M. musculus
<220> FEATURE:

<400> SEQUENCE: 204
cuccagcuau ugagucguga                                             20

<210> SEQ ID NO 205
<211> LENGTH: 20
<212> TYPE: DNA
<213> ORGANISM: M. musculus
<220> FEATURE:

<400> SEQUENCE: 205
ccugaagguu gcuuuaaggg                                             20

<210> SEQ ID NO 206
<211> LENGTH: 20
<212> TYPE: DNA
<213> ORGANISM: M. musculus
<220> FEATURE:

<400> SEQUENCE: 206
gaaaguaugu ucucaugucu                                             20

<210> SEQ ID NO 207
<211> LENGTH: 20
<212> TYPE: DNA
<213> ORGANISM: M. musculus
<220> FEATURE:

<400> SEQUENCE: 207
cuagaucuca ccuaaacaug                                             20

<210> SEQ ID NO 208
<211> LENGTH: 20
<212> TYPE: DNA
<213> ORGANISM: M. musculus
<220> FEATURE:

<400> SEQUENCE: 208
ccuaauaaag cuggauaaga                                             20

<210> SEQ ID NO 209
<211> LENGTH: 20
<212> TYPE: DNA
<213> ORGANISM: H. sapiens
<220> FEATURE:

<400> SEQUENCE: 209
gcugcauggc accucuguuc                                             20

<210> SEQ ID NO 210
<211> LENGTH: 20
<212> TYPE: DNA
<213> ORGANISM: H. sapiens
<220> FEATURE:

<400> SEQUENCE: 210 ggcagaggc caggagcgcca                                             20

```
<210> SEQ ID NO 211
<211> LENGTH: 20
<212> TYPE: DNA
<213> ORGANISM: H. sapiens
<220> FEATURE:

<400> SEQUENCE: 211
cugaagcucg ggcagaggcc                                          20

<210> SEQ ID NO 212
<211> LENGTH: 20
<212> TYPE: DNA
<213> ORGANISM: H. sapiens
<220> FEATURE:

<400> SEQUENCE: 212
uccucggccu cugaagcucg                                          20

<210> SEQ ID NO 213
<211> LENGTH: 20
<212> TYPE: DNA
<213> ORGANISM: H. sapiens
<220> FEATURE:

<400> SEQUENCE: 213
ucuugguggc gugcuucaug                                          20

<210> SEQ ID NO 214
<211> LENGTH: 20
<212> TYPE: DNA
<213> ORGANISM: H. sapiens
<220> FEATURE:

<400> SEQUENCE: 214
gcucagugca uccuuggcgg                                          20

<210> SEQ ID NO 215
<211> LENGTH: 20
<212> TYPE: DNA
<213> ORGANISM: H. sapiens
<220> FEATURE:

<400> SEQUENCE: 215
ccugcacgcu gcucagugca                                          20

<210> SEQ ID NO 216
<211> LENGTH: 20
<212> TYPE: DNA
<213> ORGANISM: H. sapiens
<220> FEATURE:

<400> SEQUENCE: 216
acugaagcca ucggucaccc                                          20

<210> SEQ ID NO 217
<211> LENGTH: 20
<212> TYPE: DNA
<213> ORGANISM: H. sapiens
<220> FEATURE:

<400> SEQUENCE: 217
cagaacucag agaacuuguc                                          20
```

```
<210> SEQ ID NO 218
<211> LENGTH: 20
<212> TYPE: DNA
<213> ORGANISM: H. sapiens
<220> FEATURE:

<400> SEQUENCE: 218
gaaguugguc ugaccucagg                                                    20

<210> SEQ ID NO 219
<211> LENGTH: 20
<212> TYPE: DNA
<213> ORGANISM: H. sapiens
<220> FEATURE:

<400> SEQUENCE: 219
cccuggagau ugcaggaccc                                                    20

<210> SEQ ID NO 220
<211> LENGTH: 20
<212> TYPE: DNA
<213> ORGANISM: H. sapiens
<220> FEATURE:

<400> SEQUENCE: 220
gggcagcccu ggagauugca                                                    20

<210> SEQ ID NO 221
<211> LENGTH: 20
<212> TYPE: DNA
<213> ORGANISM: H. sapiens
<220> FEATURE:

<400> SEQUENCE: 221 cccuuuuaa gcaaccuacag                                                    20

<210> SEQ ID NO 222
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 222
ctcttactgt gctgtggaca                                                    20

<210> SEQ ID NO 223
<211> LENGTH: 479
<212> TYPE: DNA
<213> ORGANISM: M. fascicularis
<220> FEATURE:
<221> NAME/KEY: misc_feature
<222> LOCATION: 53, 63
<223> OTHER INFORMATION: n = A,T,C or G

<400> SEQUENCE: 223
ttcatcccta gaggcagctg ctccaggaac agaggcgcca tgcagccccg ggntactcct        60
tgnttgctgc cctgctgtca ctcctggcct ctgccagtag cttcagaggc cgaggacacc       120
tcccttcttg gcattcatgc agggctacat gcagcatgcc accaagaccg ccaaggatgc       180
actgaccagc gtccaggagt cccaggtggc ccagcaggcc agaggctggg tgaccgatgg       240
cttcagttcc ctgaaaagact actggagcac cgttaaggac aagttatctg ggttctggga       300 tttgaacccct gaggccaaac ccactctggc tgaggctgcc tgagacctca ataccccaag       360
```

```
tccacctgcc tgtccatcct gccagctcct tgggtcctgc agcctccagg gctgcccctg    420
taggttgctt aaaagggaca gtattctcag tgccctccta ccgcacctca tgctggcct     479
```

<210> SEQ ID NO 224
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 224

```
ggcagccctg gaggctgcag                                                20
```

<210> SEQ ID NO 225
<211> LENGTH: 427
<212> TYPE: DNA
<213> ORGANISM: R. norvegicus

<400> SEQUENCE: 225

```
aagctcctca tcgtggccct cgtggctctc ctggcctctg cccgagctga tgagggagag    60
ggatccttgc tgctgggctc tatgcagggc tacatggaac aagcctccaa gacggtccag    120
gatgcactaa gcagcatgca ggagtctgat atagctgtgg tggccagggg ctggatggac    180
aatcgcttca atccctgaa aggctactgg agcaagttca ctgataagtt cactggcctc     240
tgggagtctg gccctgagga ccaactaaca acaccaactc ttgagccgtg agacctccat    300
gttccagatg tgtctggcca tctatcctgc tgcctccgaa ggttgctcta aggggaaagt    360
atattctcat gcctttatcc ctccccagac ctcacctaaa catgctgtcc caaataaaag    420
ctgggaa                                                             427
```

<210> SEQ ID NO 226
<211> LENGTH: 306
<212> TYPE: DNA
<213> ORGANISM: R. norvegicus

<400> SEQUENCE: 226

```
atgcagcccc gaatgctcct catcgtggcc ctcgtggctc tcctggcctc tgcccgagct    60
gatgagggag agggatcctt gctgctgggc tctatgcagg gctacatgga acaagcctcc    120
aagacggtcc aggatgcact aagcagcatg caggagtctg atatagctgt ggtggccagc    180
aggggctgga tggacaatcg cttcaaatcc ctgaaaggct actggagcaa gttcactgat    240
aagttcactg gcctctggga gtctggccct gaggaccaac taacaacacc aactcttgag    300
ccgtga                                                              306
```

<210> SEQ ID NO 227
<211> LENGTH: 20
<212> TYPE: DNA
<213> ORGANISM: Artificial Sequence
<220> FEATURE:
<223> OTHER INFORMATION: PCR primer

<400> SEQUENCE: 227

```
gagggagagg gatccttgct                                                20
```

<210> SEQ ID NO 228
<211> LENGTH: 19
<212> TYPE: DNA
<213> ORGANISM: Artificial Sequence
<220> FEATURE:
<223> OTHER INFORMATION: PCR primer

```
<400> SEQUENCE: 228
ggaccgtctt ggaggcttg                                                   19

<210> SEQ ID NO 229
<211> LENGTH: 26
<212> TYPE: DNA
<213> ORGANISM: Artificial Sequence
<220> FEATURE:
<223> OTHER INFORMATION: PCR probe

<400> SEQUENCE: 229
ctgggctcta tgcagggcta catgga                                           26

<210> SEQ ID NO 230
<211> LENGTH: 23
<212> TYPE: DNA
<213> ORGANISM: Artificial Sequence
<220> FEATURE:
<223> OTHER INFORMATION: PCR primer

<400> SEQUENCE: 230
tgttctagag acagccgcat ctt                                              23

<210> SEQ ID NO 231
<211> LENGTH: 21
<212> TYPE: DNA
<213> ORGANISM: Artificial Sequence
<220> FEATURE:
<223> OTHER INFORMATION: PCR primer

<400> SEQUENCE: 231
caccgacctt caccatcttg t                                                21

<210> SEQ ID NO 232
<211> LENGTH: 24
<212> TYPE: DNA
<213> ORGANISM: Artificial Sequence
<220> FEATURE:
<223> OTHER INFORMATION: PCR probe

<400> SEQUENCE: 232
ttgtgcagtg ccagcctcgt ctca                                             24

<210> SEQ ID NO 233
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 233
tgaacttatc agtgaacttg                                                  20

<210> SEQ ID NO 234
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 234
tcagggccag actcccagag                                                  20

<210> SEQ ID NO 235
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 235
ttggtgttgt tagttggtcc                                              20

<210> SEQ ID NO 236
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 236
ttggtgttgt tagttggtcc                                              20

<210> SEQ ID NO 237
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 237
agagccacga gggccacgat                                              20

<210> SEQ ID NO 238
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 238
agaggccagg agagccacga                                              20

<210> SEQ ID NO 239
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 239
cagctcgggc agaggccagg                                              20

<210> SEQ ID NO 240
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 240
tctccctcat cagctcgggc                                              20

<210> SEQ ID NO 241
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 241
```
gcccagcagc aaggatccct                                        20

<210> SEQ ID NO 242
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 242
cctgcataga gcccagcagc                                        20

<210> SEQ ID NO 243
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 243
tccatgtagc cctgcataga                                        20

<210> SEQ ID NO 244
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 244
ggaccgtctt ggaggcttgt                                        20

<210> SEQ ID NO 245
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 245
agtgcatcct ggaccgtctt                                        20

<210> SEQ ID NO 246
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 246
catgctgctt agtgcatcct                                        20

<210> SEQ ID NO 247
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 247
cagactcctg catgctgctt                                        20

<210> SEQ ID NO 248
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 248
acagctatat cagactcctg                                               20

<210> SEQ ID NO 249
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 249
ctggccacca cagctatatc                                               20

<210> SEQ ID NO 250
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 250
aagcgattgt ccatccagcc                                               20

<210> SEQ ID NO 251
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 251
tgctccagta gcctttcagg                                               20

<210> SEQ ID NO 252
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 252
gaacttgctc cagtagcctt                                               20

<210> SEQ ID NO 253
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 253
cagtgaactt gctccagtag                                               20

<210> SEQ ID NO 254
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 254
cttatcagtg aacttgctcc                                               20
```

<210> SEQ ID NO 255
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 255
ccagtgaact tatcagtgaa                                              20

<210> SEQ ID NO 256
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 256
gaggccagtg aacttatcag                                              20

<210> SEQ ID NO 257
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 257
ccagaggcca gtgaacttat                                              20

<210> SEQ ID NO 258
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 258
gactcccaga ggccagtgaa                                              20

<210> SEQ ID NO 259
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 259
ggccagactc ccagaggcca                                              20

<210> SEQ ID NO 260
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 260
agttggtcct cagggccaga                                              20

<210> SEQ ID NO 261
<211> LENGTH: 20
<212> TYPE: DNA
<213> ORGANISM: Artificial Sequence
<220> FEATURE:

```
<223> OTHER INFORMATION: Synthetic Oligonucleotide

<400> SEQUENCE: 261
gttagttggt cctcagggcc                                               20

<210> SEQ ID NO 262
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 262
tgttgttagt tggtcctcag                                               20

<210> SEQ ID NO 263
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 263
agagttggtg ttgttagttg                                               20

<210> SEQ ID NO 264
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 264
gctcaagagt tggtgttgtt                                               20

<210> SEQ ID NO 265
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 265
cacggctcaa gagttggtgt                                               20

<210> SEQ ID NO 266
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 266
gtctcacggc tcaagagttg                                               20

<210> SEQ ID NO 267
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 267
gaacatggag gtctcacggc                                               20
```

```
<210> SEQ ID NO 268
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 268
tctggaacat ggaggtctca                                                 20

<210> SEQ ID NO 269
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 269
cacatctgga acatggaggt                                                 20

<210> SEQ ID NO 270
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 270
cagacacatc tggaacatgg                                                 20

<210> SEQ ID NO 271
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 271
tggccagaca catctggaac                                                 20

<210> SEQ ID NO 272
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 272
aggatagatg gccagacaca                                                 20

<210> SEQ ID NO 273
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 273
cagcaggata gatggccaga                                                 20

<210> SEQ ID NO 274
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 274
gaggcagcag gatagatggc                                             20

<210> SEQ ID NO 275
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 275
ttcggaggca gcaggataga                                             20

<210> SEQ ID NO 276
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 276
aaccttcgga ggcagcagga                                             20

<210> SEQ ID NO 277
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 277
gagcaacctt cggaggcagc                                             20

<210> SEQ ID NO 278
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 278
cttagagcaa ccttcggagg                                             20

<210> SEQ ID NO 279
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 279 tcccccttaga gcaaccttcg                                            20

<210> SEQ ID NO 280
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 280
actttcccct tagagcaacc                                             20

<210> SEQ ID NO 281
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 281
atatactttc cccttagagc                                               20

<210> SEQ ID NO 282
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 282
gagaatatac tttcccctta                                               20

<210> SEQ ID NO 283
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 283
gcatgagaat atactttccc                                               20

<210> SEQ ID NO 284
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 284
aaaggcatga gaatatactt                                               20

<210> SEQ ID NO 285
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 285
ggataaaggc atgagaatat                                               20

<210> SEQ ID NO 286
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 286
ggagggataa aggcatgaga                                               20

<210> SEQ ID NO 287
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 287
```
gcatgtttag gtgaggtctg                                                                20

<210> SEQ ID NO 288
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 288
gacagcatgt ttaggtgagg                                                                20

<210> SEQ ID NO 289
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 289
ttatttggga cagcatgttt                                                                20

<210> SEQ ID NO 290
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 290
gcttttattt gggacagcat                                                                20

<210> SEQ ID NO 291
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 291
tcccagcttt tatttgggac                                                                20

<210> SEQ ID NO 292
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 292
cacgatgagg agcattcggg                                                                20

<210> SEQ ID NO 293
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 293
agggccacga tgaggagcat                                                                20

<210> SEQ ID NO 294
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 294
ccacgagggc cacgatgagg                                                   20

<210> SEQ ID NO 295
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 295
gagagccacg agggccacga                                                   20

<210> SEQ ID NO 296
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 296
gccaggagag ccacgagggc                                                   20

<210> SEQ ID NO 297
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 297
cagaggccag gagagccacg                                                   20

<210> SEQ ID NO 298
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 298
tcgggcagag gccaggagag                                                   20

<210> SEQ ID NO 299
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 299
tcagctcggg cagaggccag                                                   20

<210> SEQ ID NO 300
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 300
cctcatcagc tcgggcagag                                                   20
```

<210> SEQ ID NO 301
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 301
ctctccctca tcagctcggg　　　　　　　　　　　　　　　　　　　　　　　　　　　20

<210> SEQ ID NO 302
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 302
gatccctctc cctcatcagc　　　　　　　　　　　　　　　　　　　　　　　　　　　20

<210> SEQ ID NO 303
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 303
gcaaggatcc ctctccctca　　　　　　　　　　　　　　　　　　　　　　　　　　　20

<210> SEQ ID NO 304
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 304
cagcagcaag gatccctctc　　　　　　　　　　　　　　　　　　　　　　　　　　　20

<210> SEQ ID NO 305
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 305
gagcccagca gcaaggatcc　　　　　　　　　　　　　　　　　　　　　　　　　　　20

<210> SEQ ID NO 306
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 306
gcatagagcc cagcagcaag　　　　　　　　　　　　　　　　　　　　　　　　　　　20

<210> SEQ ID NO 307
<211> LENGTH: 20
<212> TYPE: DNA
<213> ORGANISM: Artificial Sequence
<220> FEATURE:
<223> OTHER INFORMATION: Synthetic Oligonucleotide

```
-continued

<400> SEQUENCE: 307
gccctgcata gagcccagca                                              20

<210> SEQ ID NO 308
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 308
atgtagccct gcatagagcc                                              20

<210> SEQ ID NO 309
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 309
gttccatgta gccctgcata                                              20

<210> SEQ ID NO 310
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 310
ggcttgttcc atgtagccct                                              20

<210> SEQ ID NO 311
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 311
ttggaggctt gttccatgta                                              20

<210> SEQ ID NO 312
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 312
ccgtcttgga ggcttgttcc                                              20

<210> SEQ ID NO 313
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 313
ctggaccgtc ttggaggctt                                              20

<210> SEQ ID NO 314
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 314
gcatcctgga ccgtcttgga                                           20

<210> SEQ ID NO 315
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 315
ttagtgcatc ctggaccgtc                                           20

<210> SEQ ID NO 316
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 316
gctgcttagt gcatcctgga                                           20

<210> SEQ ID NO 317
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 317
tgcatgctgc ttagtgcatc                                           20

<210> SEQ ID NO 318
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 318
actcctgcat gctgcttagt                                           20

<210> SEQ ID NO 319
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 319
atcagactcc tgcatgctgc                                           20

<210> SEQ ID NO 320
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 320
```
gctatatcag actcctgcat                                              20

<210> SEQ ID NO 321
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 321
ccacagctat atcagactcc                                              20

<210> SEQ ID NO 322
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 322
ggccaccaca gctatatcag                                              20

<210> SEQ ID NO 323
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 323
ctgctggcca ccacagctat                                              20

<210> SEQ ID NO 324
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 324
agcccctgct ggccaccaca                                              20

<210> SEQ ID NO 325
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 325
catccagccc ctgctggcca                                              20

<210> SEQ ID NO 326
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 326
ttgtccatcc agcccctgct                                              20

<210> SEQ ID NO 327
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 327
attgtccatc cagcccctgc                                               20

<210> SEQ ID NO 328
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 328
agcgattgtc catccagccc                                               20

<210> SEQ ID NO 329
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 329
tttgaagcga ttgtccatcc                                               20

<210> SEQ ID NO 330
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 330
agggatttga agcgattgtc                                               20

<210> SEQ ID NO 331
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 331
ctttcaggga tttgaagcga                                               20

<210> SEQ ID NO 332
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 332
gtagcctttc agggatttga                                               20

<210> SEQ ID NO 333
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 333
ctccagtagc ctttcaggga                                               20
```

<210> SEQ ID NO 334
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 334
acttgctcca gtagcctttc                                               20

<210> SEQ ID NO 335
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 335
agtgaacttg ctccagtagc                                               20

<210> SEQ ID NO 336
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 336
ttatcagtga acttgctcca                                               20

<210> SEQ ID NO 337
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 337
gccagtgaac ttatcagtga                                               20

<210> SEQ ID NO 338
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 338
cagaggccag tgaacttatc                                               20

<210> SEQ ID NO 339
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 339
actcccagag gccagtgaac                                               20

<210> SEQ ID NO 340
<211> LENGTH: 20
<212> TYPE: DNA
<213> ORGANISM: Artificial Sequence
<220> FEATURE:

```
<223> OTHER INFORMATION: Synthetic Oligonucleotide

<400> SEQUENCE: 340
gccagactcc cagaggccag                                               20

<210> SEQ ID NO 341
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 341
tagttggtcc tcagggccag                                               20

<210> SEQ ID NO 342
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 342
gttgttagtt ggtcctcagg                                               20

<210> SEQ ID NO 343
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 343
aagagttggt gttgttagtt                                               20

<210> SEQ ID NO 344
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 344
ggctcaagag ttggtgttgt                                               20

<210> SEQ ID NO 345
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 345
tcacggctca agagttggtg                                               20

<210> SEQ ID NO 346
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 346
ggaggcttgt tccatgtagc                                               20
```

```
<210> SEQ ID NO 347
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 347
tcagggattt gaagcgattg                                               20

<210> SEQ ID NO 348
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 348
cagtagcctt tcagggattt                                               20

<210> SEQ ID NO 349
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 349
atggaggtct cacggctcaa                                               20

<210> SEQ ID NO 350
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 350
tagatggcca gacacatctg                                               20

<210> SEQ ID NO 351
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 351
ttgggacagc atgtttaggt                                               20

<210> SEQ ID NO 352
<211> LENGTH: 435
<212> TYPE: DNA
<213> ORGANISM: M. auratus

<400> SEQUENCE: 352
actcctattg ttgccctctt ggcactcctg gcatctgccc gaagctaatg aggtagaggg    60
gtccttgctg ctgggctctg tgcagggcta catggaacag gccaccaaga aggtccagga   120
tgcgctaacc agcatgcaaa agtctgaggt ggctgtgcgg gccagggact ggatggacgg   180
tggcttcacc tccctgaaaa gctactggag cacatttact gacacggtct ccagcctctg   240
ggattcttcc cccaaggccc taccagcccc agctactgag ccttgagacc tctacgttcc   300
aaatgtgctt gtgtgtccat cctgctggcc tctgggcctg ggtggcccct gaaggttgtt   360
```

```
tgaaagggaa agtattgtca tgttttcatc cctccccaga agtcacctaa acatgctgtc    420
ctaaataaag ctgga                                                    435
```

<210> SEQ ID NO 353
<211> LENGTH: 20
<212> TYPE: DNA
<213> ORGANISM: Artificial Sequence
<220> FEATURE:
<223> OTHER INFORMATION: PCR primer

<400> SEQUENCE: 353

```
cgctaaccag catgcaaaag                                                20
```

<210> SEQ ID NO 354
<211> LENGTH: 18
<212> TYPE: DNA
<213> ORGANISM: Artificial Sequence
<220> FEATURE:
<223> OTHER INFORMATION: PCR primer

<400> SEQUENCE: 354

```
caccgtccat ccagtccc                                                  18
```

<210> SEQ ID NO 355
<211> LENGTH: 20
<212> TYPE: DNA
<213> ORGANISM: Artificial Sequence
<220> FEATURE:
<223> OTHER INFORMATION: PCR probe

<400> SEQUENCE: 355

```
ctgaggtggc tgtgcgggcc                                                20
```

<210> SEQ ID NO 356
<211> LENGTH: 15
<212> TYPE: DNA
<213> ORGANISM: Artificial Sequence
<220> FEATURE:
<223> OTHER INFORMATION: PCR primer

<400> SEQUENCE: 356

```
ccagcctcgc tccgg                                                     15
```

<210> SEQ ID NO 357
<211> LENGTH: 18
<212> TYPE: DNA
<213> ORGANISM: Artificial Sequence
<220> FEATURE:
<223> OTHER INFORMATION: PCR primer

<400> SEQUENCE: 357

```
ccaatacggc caaatccg                                                  18
```

<210> SEQ ID NO 358
<211> LENGTH: 21
<212> TYPE: DNA
<213> ORGANISM: Artificial Sequence
<220> FEATURE:
<223> OTHER INFORMATION: PCR probe

<400> SEQUENCE: 358

```
acgcaatggt gaaggtcggc g                                              21
```

<210> SEQ ID NO 359
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 359
tgccaagagg gcaacaatag                                               20

<210> SEQ ID NO 360
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 360
aggagtgcca agagggcaac                                               20

<210> SEQ ID NO 361
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 361
gatgccagga gtgccaagag                                               20

<210> SEQ ID NO 362
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 362
ggcagatgcc aggagtgcca                                               20

<210> SEQ ID NO 363
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 363
ctctacctca ttagcttcgg                                               20

<210> SEQ ID NO 364
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 364
ccctctacct cattagcttc                                               20

<210> SEQ ID NO 365
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 365
```

```
gacccctcta cctcattagc                                              20

<210> SEQ ID NO 366
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 366
gcaaggaccc ctctacctca                                              20

<210> SEQ ID NO 367
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 367
cagcagcaag gacccctcta                                              20

<210> SEQ ID NO 368
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 368
gagcccagca gcaaggaccc                                              20

<210> SEQ ID NO 369
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 369
tgcacagagc ccagcagcaa                                              20

<210> SEQ ID NO 370
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 370
agccctgcac agagcccagc                                              20

<210> SEQ ID NO 371
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 371
catgtagccc tgcacagagc                                              20

<210> SEQ ID NO 372
<211> LENGTH: 20
<212> TYPE: DNA
<213> ORGANISM: Artificial Sequence
```

```
<220> FEATURE:
<223> OTHER INFORMATION: Synthetic Oligonucleotide

<400> SEQUENCE: 372
tgttccatgt agccctgcac                                               20

<210> SEQ ID NO 373
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 373
tggcctgttc catgtagccc                                               20

<210> SEQ ID NO 374
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 374
accttcttgg tggcctgttc                                               20

<210> SEQ ID NO 375
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 375
gcgcatcctg gaccttcttg                                               20

<210> SEQ ID NO 376
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 376
tgctggttag cgcatcctgg                                               20

<210> SEQ ID NO 377
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 377
ttgcatgctg gttagcgcat                                               20

<210> SEQ ID NO 378
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 378
gacttttgca tgctggttag                                               20
```

<210> SEQ ID NO 379
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 379
cctcagactt ttgcatgctg					20

<210> SEQ ID NO 380
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 380
agccacctca gacttttgca					20

<210> SEQ ID NO 381
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 381
cgcacagcca cctcagactt					20

<210> SEQ ID NO 382
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 382
ccagtccctg gcccgcacag					20

<210> SEQ ID NO 383
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 383
gtccatccag tccctggccc					20

<210> SEQ ID NO 384
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 384
ccgtccatcc agtccctggc					20

<210> SEQ ID NO 385
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 385
gccaccgtcc atccagtccc                                               20

<210> SEQ ID NO 386
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 386
gtgaagccac cgtccatcca                                               20

<210> SEQ ID NO 387
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 387
ggaggtgaag ccaccgtcca                                               20

<210> SEQ ID NO 388
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 388
tgctccagta gcttttcagg                                               20

<210> SEQ ID NO 389
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 389
gtaaatgtgc tccagtagct                                               20

<210> SEQ ID NO 390
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 390
tgtcagtaaa tgtgctccag                                               20

<210> SEQ ID NO 391
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 391
tggagaccgt gtcagtaaat                                               20

<210> SEQ ID NO 392
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 392
ggctggagac cgtgtcagta                                              20

<210> SEQ ID NO 393
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 393
cagaggctgg agaccgtgtc                                              20

<210> SEQ ID NO 394
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 394
atcccagagg ctggagaccg                                              20

<210> SEQ ID NO 395
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 395
gaagaatccc agaggctgga                                              20

<210> SEQ ID NO 396
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 396
tctcaaggct cagtagctgg                                              20

<210> SEQ ID NO 397
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 397
tagaggtctc aaggctcagt                                              20

<210> SEQ ID NO 398
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 398
```
gaacgtagag gtctcaaggc                                              20

<210> SEQ ID NO 399
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 399
catttggaac gtagaggtct                                              20

<210> SEQ ID NO 400
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 400
caagcacatt tggaacgtag                                              20

<210> SEQ ID NO 401
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 401
tggacacaca agcacatttg                                              20

<210> SEQ ID NO 402
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 402
caggatggac acacaagcac                                              20

<210> SEQ ID NO 403
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 403
ggccagcagg atggacacac                                              20

<210> SEQ ID NO 404
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 404
gcccagaggc cagcaggatg                                              20

<210> SEQ ID NO 405
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 405
cctttcaaac aaccttcagg                                                 20

<210> SEQ ID NO 406
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 406
ggacagcatg tttaggtgac                                                 20

<210> SEQ ID NO 407
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 407
cttggtggcc tgttccatgt                                                 20

<210> SEQ ID NO 408
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 408
gttagcgcat cctggacctt                                                 20

<210> SEQ ID NO 409
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 409
tggcccgcac agccacctca                                                 20

<210> SEQ ID NO 410
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 410
gaccgtgtca gtaaatgtgc                                                 20

<210> SEQ ID NO 411
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 411
aagagggcaa caataggagt                                                 20
```

<210> SEQ ID NO 412
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 412
gtgccaagag ggcaacaata                                          20

<210> SEQ ID NO 413
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 413
atgccaggag tgccaagagg                                          20

<210> SEQ ID NO 414
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 414
cttcgggcag atgccaggag                                          20

<210> SEQ ID NO 415
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 415
cattagcttc gggcagatgc                                          20

<210> SEQ ID NO 416
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 416
agagcccagc agcaaggacc                                          20

<210> SEQ ID NO 417
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 417
gtggcctgtt ccatgtagcc                                          20

<210> SEQ ID NO 418
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 418
tcttggtggc ctgttccatg                                               20

<210> SEQ ID NO 419
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 419
gaccttcttg gtggcctgtt                                               20

<210> SEQ ID NO 420
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 420
tcctggacct tcttggtggc                                               20

<210> SEQ ID NO 421
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 421
ggttagcgca tcctggacct                                               20

<210> SEQ ID NO 422
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 422
atgctggtta gcgcatcctg                                               20

<210> SEQ ID NO 423
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 423
tttgcatgct ggttagcgca                                               20

<210> SEQ ID NO 424
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 424
agacttttgc atgctggtta                                               20

-continued

```
<210> SEQ ID NO 425
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 425
acctcagact tttgcatgct                                                   20

<210> SEQ ID NO 426
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 426
cagccacctc agactttttgc                                                  20

<210> SEQ ID NO 427
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 427
ccgcacagcc acctcagact                                                   20

<210> SEQ ID NO 428
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 428
ctggcccgca cagccacctc                                                   20

<210> SEQ ID NO 429
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 429
agtccctggc ccgcacagcc                                                   20

<210> SEQ ID NO 430
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 430
catccagtcc ctggcccgca                                                   20

<210> SEQ ID NO 431
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 431
agccaccgtc catccagtcc								20

<210> SEQ ID NO 432
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 432
ggtgaagcca ccgtccatcc								20

<210> SEQ ID NO 433
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 433
agggaggtga agccaccgtc								20

<210> SEQ ID NO 434
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 434
ttttcaggga ggtgaagcca								20

<210> SEQ ID NO 435
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 435
agtagctttt cagggaggtg								20

<210> SEQ ID NO 436
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 436
aaatgtgctc cagtagcttt								20

<210> SEQ ID NO 437
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 437
tcagtaaatg tgctccagta								20

<210> SEQ ID NO 438
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 438
ccgtgtcagt aaatgtgctc                                              20

<210> SEQ ID NO 439
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 439
ggagaccgtg tcagtaaatg                                              20

<210> SEQ ID NO 440
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 440
aggctggaga ccgtgtcagt                                              20

<210> SEQ ID NO 441
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 441
cccagaggct ggagaccgtg                                              20

<210> SEQ ID NO 442
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 442
agaatcccag aggctggaga                                              20

<210> SEQ ID NO 443
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 443
agaggtctca aggctcagta                                              20

<210> SEQ ID NO 444
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 444
```
aacgtagagg tctcaaggct                                          20

<210> SEQ ID NO 445
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 445
tttggaacgt agaggtctca                                          20

<210> SEQ ID NO 446
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 446
gcacatttgg aacgtagagg                                          20

<210> SEQ ID NO 447
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 447
cacaagcaca tttggaacgt                                          20

<210> SEQ ID NO 448
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 448
ggacacacaa gcacatttgg                                          20

<210> SEQ ID NO 449
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 449
aggatggaca cacaagcaca                                          20

<210> SEQ ID NO 450
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 450
ccagcaggat ggacacacaa                                          20

<210> SEQ ID NO 451
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 451
agaggccagc aggatggaca                                              20

<210> SEQ ID NO 452
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 452
ggcccagagg ccagcaggat                                              20

<210> SEQ ID NO 453
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 453
acccaggccc agaggccagc                                              20

<210> SEQ ID NO 454
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 454
gggccaccca ggcccagagg                                              20

<210> SEQ ID NO 455
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 455
ctttcccttt caaacaacct                                              20

<210> SEQ ID NO 456
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 456
caatactttc cctttcaaac                                              20

<210> SEQ ID NO 457
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 457
catgacaata ctttcccttt                                              20
```

```
<210> SEQ ID NO 458
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 458
gaaaacatga caatactttc                                                   20

<210> SEQ ID NO 459
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 459
gggatgaaaa catgacaata                                                   20

<210> SEQ ID NO 460
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 460
catgtttagg tgacttctgg                                                   20

<210> SEQ ID NO 461
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 461
gacagcatgt ttaggtgact                                                   20

<210> SEQ ID NO 462
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 462
tttaggacag catgtttagg                                                   20

<210> SEQ ID NO 463
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 463
ctttatttag gacagcatgt                                                   20

<210> SEQ ID NO 464
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 464
tccagcttta tttaggacag                                                      20

<210> SEQ ID NO 465
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 465
cgagaggcgg acgggaccg                                                       19

<210> SEQ ID NO 466
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 466
cgagaggcgg acgggaccgt t                                                    21

<210> SEQ ID NO 467
<211> LENGTH: 21
<212> TYPE: DNA
<213> ORGANISM: Artificial Sequence
<220> FEATURE:
<223> OTHER INFORMATION: complement Oligonucleotide

<400> SEQUENCE: 467
ttgctctccg cctgccctgg c                                                    21

<210> SEQ ID NO 468
<211> LENGTH: 19
<212> TYPE: DNA
<213> ORGANISM: Artificial Sequence
<220> FEATURE:
<223> OTHER INFORMATION: complement Oligonucleotide

<400> SEQUENCE: 468
gctctccgcc tgccctggc                                                       19
```